(12) United States Patent
Kuracina et al.

(10) Patent No.: US 9,238,104 B2
(45) Date of Patent: Jan. 19, 2016

(54) NEEDLE GUARD

(75) Inventors: Thomas C. Kuracina, Carson City, NV (US); Tim L. Kitchen, Barcelona (ES)

(73) Assignee: INJECTIMED, INC., Minden, NV (US)

( * ) Notice: Subject to any disclaimer, the term of this patent is extended or adjusted under 35 U.S.C. 154(b) by 516 days.

(21) Appl. No.: 13/596,023

(22) Filed: Aug. 27, 2012

(65) Prior Publication Data

US 2013/0023835 A1    Jan. 24, 2013

Related U.S. Application Data

(63) Continuation-in-part of application No. 13/037,164, filed on Feb. 28, 2011, now Pat. No. 8,764,711.

(51) Int. Cl.
| | |
|---|---|
| *A61M 5/00* | (2006.01) |
| *A61M 5/162* | (2006.01) |
| *A61B 5/15* | (2006.01) |
| *A61M 5/32* | (2006.01) |
| *A61M 25/06* | (2006.01) |
| *A61M 5/158* | (2006.01) |

(52) U.S. Cl.
CPC ........ *A61M 5/1626* (2013.01); *A61B 5/150633* (2013.01); *A61M 5/158* (2013.01); *A61M 5/3205* (2013.01); *A61M 5/3245* (2013.01); *A61M 25/0618* (2013.01); *A61M 25/0625* (2013.01); *A61M 2005/1587* (2013.01); *A61M 2005/325* (2013.01)

(58) Field of Classification Search
CPC .......... A61M 25/0625; A61M 5/3245; A61M 25/0618; A61M 5/3205; A61M 2005/325; A61M 5/1626; A61M 5/158; A61B 5/150633
See application file for complete search history.

(56) References Cited

U.S. PATENT DOCUMENTS

| | | |
|---|---|---|
| 1,703,296 A | 6/1902 | Nuesch |
| 2,950,822 A | 3/1910 | McElroy |
| 1,899,492 A | 2/1933 | Beebe |
| 2,409,979 A | 10/1946 | Huber |
| 2,717,599 A | 9/1955 | Huber |
| 2,748,769 A | 6/1956 | Huber |

(Continued)

FOREIGN PATENT DOCUMENTS

| | | |
|---|---|---|
| EP | 0352928 A1 | 1/1990 |
| EP | 0475375 A1 | 3/1992 |

(Continued)

OTHER PUBLICATIONS

International Search Report and Written Opinion of the International Searching Authority Search Report Application No. PCT/US2012/026659 issued by USPTO, Alexandria, Virginia dated Jul. 2, 2012.

(Continued)

*Primary Examiner* — Bhisma Mehta
*Assistant Examiner* — Bradley Osinski
(74) *Attorney, Agent, or Firm* — Edell, Shapiro & Finnan, LLC

(57) ABSTRACT

A needle guard assembly having a resilient arm extending from a base situated to slide along the shaft of a needle. In one implementation the needle guard has an elongate containment member that rides with the resilient arm and is co-operable with the resilient arm to effectuate a covering of the entire distal tip of the needle upon the needle being retracted into the needle guard.

26 Claims, 32 Drawing Sheets

(56) References Cited

U.S. PATENT DOCUMENTS

| | | |
|---|---|---|
| 2,828,744 A | 4/1958 | Hirsch et al. |
| 2,840,075 A | 6/1958 | Morris et al. |
| 2,922,420 A | 1/1960 | Hirsch et al. |
| 3,093,134 A | 6/1963 | Roehr |
| 3,386,438 A | 6/1968 | Stevens |
| 3,492,992 A | 2/1970 | Kutz |
| 3,662,754 A | 5/1972 | Halloran |
| 3,727,613 A | 4/1973 | Sorenson et al. |
| 4,091,811 A | 5/1978 | Bates et al. |
| 4,139,009 A | 2/1979 | Alvarez |
| 4,431,426 A | 2/1984 | Groshong et al. |
| 4,534,763 A | 8/1985 | Gettig et al. |
| 4,551,138 A | 11/1985 | Shinohara |
| 4,693,708 A | 9/1987 | Wanderer et al. |
| 4,731,059 A | 3/1988 | Wanderer et al. |
| 4,735,612 A | 4/1988 | Chevalier |
| 4,755,170 A | 7/1988 | Golden |
| 4,781,692 A | 11/1988 | Jagger et al. |
| 4,790,828 A | 12/1988 | Dombrowski et al. |
| 4,795,432 A | 1/1989 | Karczmer |
| 4,834,718 A | 5/1989 | McDonald |
| 4,838,853 A | 6/1989 | Parisi |
| 4,850,977 A | 7/1989 | Bayless |
| 4,863,434 A | 9/1989 | Bayless |
| 4,863,435 A | 9/1989 | Shurman et al. |
| 4,887,998 A | 12/1989 | Martin et al. |
| 4,917,673 A | 4/1990 | Coplin |
| 4,921,490 A | 5/1990 | Spier et al. |
| 4,929,241 A | 5/1990 | Kulli |
| 4,944,728 A | 7/1990 | Carrell et al. |
| 4,944,731 A | 7/1990 | Cole |
| 4,952,207 A | 8/1990 | Lemieux |
| 4,955,866 A | 9/1990 | Corey |
| 4,964,854 A | 10/1990 | Luther |
| 4,978,344 A | 12/1990 | Dombrowski et al. |
| 4,994,041 A | 2/1991 | Dombrowski et al. |
| 4,998,922 A | 3/1991 | Kuracina et al. |
| 5,000,740 A | 3/1991 | Ducharme et al. |
| 5,013,304 A | 5/1991 | Russell et al. |
| 5,015,242 A | 5/1991 | Heifetz |
| 5,032,117 A | 7/1991 | Motta |
| 5,040,691 A | 8/1991 | Hayes et al. |
| 5,049,136 A | 9/1991 | Johnson |
| 5,051,109 A | 9/1991 | Simon |
| 5,053,014 A | 10/1991 | Van Heugten |
| 5,053,017 A | 10/1991 | Chamuel |
| 5,057,079 A | 10/1991 | Tiemann et al. |
| 5,059,180 A | 10/1991 | McLees |
| 5,061,249 A | 10/1991 | Campbell |
| 5,085,648 A | 2/1992 | Purdy et al. |
| 5,090,564 A | 2/1992 | Chimienti |
| 5,092,845 A | 3/1992 | Chang |
| 5,092,851 A | 3/1992 | Ragner |
| 5,104,385 A | 4/1992 | Huband |
| 5,120,321 A | 6/1992 | Oksman et al. |
| 5,120,324 A | 6/1992 | Sancoff |
| 5,135,504 A | 8/1992 | McLees |
| 5,147,327 A | 9/1992 | Johnson |
| 5,176,650 A | 1/1993 | Haining |
| 5,176,655 A | 1/1993 | McCormick et al. |
| 5,176,656 A | 1/1993 | Bayless |
| 5,183,468 A | 2/1993 | McLees |
| 5,188,617 A | 2/1993 | Linder |
| 5,195,982 A | 3/1993 | Hoenig |
| 5,195,992 A | 3/1993 | Dudar et al. |
| 5,197,956 A | 3/1993 | Brizuela |
| 5,201,713 A | 4/1993 | Rossetti |
| 5,215,528 A | 6/1993 | Purdy et al. |
| 5,217,437 A | 6/1993 | Talonn et al. |
| 5,221,266 A | 6/1993 | Kastan |
| 5,242,414 A | 9/1993 | Fischell et al. |
| RE34,416 E | 10/1993 | Lemieux |
| 5,254,099 A | 10/1993 | Kuracina et al. |
| 5,254,100 A | 10/1993 | Huband |
| 5,256,153 A | 10/1993 | Hake |
| 5,261,894 A | 11/1993 | Smith et al. |
| 5,263,934 A | 11/1993 | Haak |
| 5,269,765 A | 12/1993 | Kuracina |
| 5,273,540 A | 12/1993 | Luther et al. |
| 5,279,588 A | 1/1994 | Nicoletti et al. |
| 5,279,591 A | 1/1994 | Simon |
| 5,281,391 A | 1/1994 | Hanson et al. |
| 5,290,233 A | 3/1994 | Campbell |
| 5,295,963 A | 3/1994 | Deeks |
| 5,300,045 A | 4/1994 | Plassche, Jr. |
| 5,304,151 A | 4/1994 | Kuracina |
| 5,312,345 A | 5/1994 | Cole |
| 5,312,366 A | 5/1994 | Vailancourt |
| 5,312,422 A | 5/1994 | Trott |
| 5,314,414 A | 5/1994 | Hake et al. |
| 5,314,503 A | 5/1994 | Bobrove et al. |
| 5,322,517 A | 6/1994 | Sircom et al. |
| 5,324,265 A | 6/1994 | Murray et al. |
| 5,334,149 A | 8/1994 | Nortman et al. |
| 5,334,158 A | 8/1994 | McLees |
| 5,336,185 A | 8/1994 | Lynch et al. |
| 5,336,197 A | 8/1994 | Kuracina et al. |
| 5,348,544 A | 9/1994 | Sweeney et al. |
| 5,356,383 A | 10/1994 | Daly et al. |
| 5,360,211 A | 11/1994 | Smith et al. |
| 5,360,404 A | 11/1994 | Novacek et al. |
| 5,360,408 A | 11/1994 | Vaillancourt |
| 5,360,416 A | 11/1994 | Ausherman et al. |
| 5,364,360 A | 11/1994 | Flumene et al. |
| 5,364,370 A | 11/1994 | Szerlip et al. |
| 5,364,373 A | 11/1994 | Waskonig et al. |
| 5,374,250 A | 12/1994 | Dixon |
| 5,380,296 A | 1/1995 | Smedley et al. |
| 5,395,347 A | 3/1995 | Blecher et al. |
| 5,401,250 A | 3/1995 | Shields |
| 5,407,431 A | 4/1995 | Botich et al. |
| 5,409,461 A | 4/1995 | Steinman |
| 5,411,486 A | 5/1995 | Zadini et al. |
| 5,419,766 A | 5/1995 | Chang et al. |
| 5,423,766 A | 6/1995 | Di Cesare |
| 5,425,720 A | 6/1995 | Rogalsky et al. |
| 5,425,721 A | 6/1995 | Malenchek |
| 5,445,618 A | 8/1995 | Adobbati |
| 5,447,501 A | 9/1995 | Karlsson et al. |
| 5,449,349 A | 9/1995 | Sallee et al. |
| 5,458,658 A | 10/1995 | Sircom |
| 5,462,062 A | 10/1995 | Rubinstein et al. |
| 5,462,533 A | 10/1995 | Daugherty |
| 5,466,223 A | 11/1995 | Bressler et al. |
| 5,478,313 A | 12/1995 | White |
| 5,486,164 A | 1/1996 | Streck |
| 5,487,733 A | 1/1996 | Caizza et al. |
| 5,495,855 A | 3/1996 | Dudar et al. |
| 5,498,241 A | 3/1996 | Fabozzi |
| 5,498,243 A | 3/1996 | Vallelunga et al. |
| 5,509,907 A | 4/1996 | Bevilacqua |
| 5,514,099 A | 5/1996 | McCarthy |
| 5,514,113 A | 5/1996 | Anderson et al. |
| 5,540,667 A | 7/1996 | Tanner, II |
| 5,549,570 A | 8/1996 | Rogalsky |
| 5,554,126 A | 9/1996 | Filley |
| 5,554,135 A | 9/1996 | Menyhay |
| 5,558,651 A | 9/1996 | Crawford et al. |
| 5,562,631 A | 10/1996 | Bogert |
| 5,562,633 A | 10/1996 | Wozencroft |
| 5,562,634 A | 10/1996 | Flumene et al. |
| 5,573,510 A | 11/1996 | Isaacson |
| 5,582,597 A | 12/1996 | Brimhall et al. |
| 5,584,809 A | 12/1996 | Gaba |
| 5,584,810 A | 12/1996 | Brimhall |
| 5,584,818 A | 12/1996 | Morrison |
| 5,595,566 A | 1/1997 | Vallelunga et al. |
| 5,599,310 A | 2/1997 | Bogert |
| 5,601,536 A | 2/1997 | Crawford et al. |
| 5,611,781 A | 3/1997 | Sircom et al. |
| 5,662,610 A | 9/1997 | Sircom |
| 5,662,619 A | 9/1997 | Zarata |
| 5,669,890 A | 9/1997 | Grimm |
| 5,683,365 A | 11/1997 | Brown et al. |

(56) References Cited

U.S. PATENT DOCUMENTS

| | | | |
|---|---|---|---|
| 5,697,907 A | 12/1997 | Gaba | |
| 5,716,348 A | 2/1998 | Marinacci et al. | |
| 5,718,688 A | 2/1998 | Wozencraft | |
| 5,755,699 A | 5/1998 | Blecher et al. | |
| 5,797,880 A | 8/1998 | Erskine et al. | |
| 5,810,780 A | 9/1998 | Brimhall et al. | |
| 5,827,305 A | 10/1998 | Gordon | |
| 5,853,393 A | 12/1998 | Bogert | |
| 5,858,006 A | 1/1999 | Van der AA et al. | |
| 5,868,721 A | 2/1999 | Marinacci et al. | |
| 5,879,337 A | 3/1999 | Kuracina et al. | |
| 5,938,635 A | 8/1999 | Kuhle | |
| 5,941,850 A | 8/1999 | Shah et al. | |
| 6,001,080 A | 12/1999 | Kuracina et al. | |
| 6,004,294 A | 12/1999 | Brimhall et al. | |
| 6,004,302 A | 12/1999 | Bierley | |
| 6,024,727 A | 2/2000 | Thorne et al. | |
| 6,039,715 A | 3/2000 | Mackool | |
| 6,063,040 A | 5/2000 | Ownen et al. | |
| 6,117,108 A | 9/2000 | Woehr et al. | |
| 6,165,157 A | 12/2000 | Dillon et al. | |
| 6,193,694 B1 | 2/2001 | Bell et al. | |
| 6,193,695 B1 | 2/2001 | Rippstein et al. | |
| 6,224,569 B1 | 5/2001 | Brimhall | |
| 6,287,278 B1 | 9/2001 | Woehr et al. | |
| 6,379,333 B1 | 4/2002 | Brimhall et al. | |
| 6,406,459 B1 | 6/2002 | Allmon | |
| 6,443,929 B1 | 9/2002 | Kuracina et al. | |
| 6,585,704 B2 | 7/2003 | Luther et al. | |
| 6,588,432 B1 | 7/2003 | Rehder et al. | |
| 6,595,954 B1 | 7/2003 | Luther et al. | |
| 6,595,955 B2 | 7/2003 | Furgeson et al. | |
| 6,616,630 B1 | 9/2003 | Woehr et al. | |
| 6,623,458 B2 | 9/2003 | Woehr et al. | |
| 6,629,959 B2 | 10/2003 | Kuracina et al. | |
| 6,632,201 B1 | 10/2003 | Mathias et al. | |
| 6,652,486 B2 | 11/2003 | Bialecki et al. | |
| 6,795,962 B1 | 9/2004 | Furgeson et al. | |
| 6,814,725 B2 | 11/2004 | Gutierrez | |
| 6,827,692 B2 | 12/2004 | Castellacci | |
| 6,860,871 B2 | 3/2005 | Kuracina et al. | |
| 6,902,546 B2 | 6/2005 | Furgeson | |
| 6,972,002 B2 | 12/2005 | Thorne | |
| 6,984,213 B2 | 1/2006 | Horner et al. | |
| RE38,996 E | 2/2006 | Crawford | |
| 7,004,927 B2 | 2/2006 | Furgeson et al. | |
| 7,008,402 B2 | 3/2006 | Furgeson et al. | |
| 7,125,397 B2 | 10/2006 | Woehr et al. | |
| 7,160,269 B2 | 1/2007 | Woehr | |
| 7,179,244 B2 | 2/2007 | Smith et al. | |
| 7,186,239 B2 | 3/2007 | Woehr | |
| 7,214,211 B2 | 5/2007 | Woehr et al. | |
| 7,226,434 B2 | 6/2007 | Carlyon et al. | |
| 7,247,148 B2 | 7/2007 | Murashita | |
| 7,264,613 B2 | 9/2007 | Woehr et al. | |
| 7,291,130 B2 | 11/2007 | McGurk | |
| 7,303,548 B2 | 12/2007 | Rhad | |
| 7,341,573 B2 | 3/2008 | Furgeson et al. | |
| 7,347,838 B2 | 3/2008 | Kulli | |
| 7,357,784 B2 | 4/2008 | Furgeson et al. | |
| 7,374,554 B2 | 5/2008 | Menzi et al. | |
| 7,413,562 B2 | 8/2008 | Furgeson et al. | |
| 7,422,572 B2 | 9/2008 | Popov et al. | |
| 7,422,573 B2 | 9/2008 | Wilinson et al. | |
| 7,458,954 B2 | 12/2008 | Furgeson et al. | |
| 7,500,965 B2 | 3/2009 | Menzi et al. | |
| 7,507,222 B2 | 3/2009 | Cindrich et al. | |
| 7,534,231 B2 | 5/2009 | Kuracina et al. | |
| 7,566,323 B2 | 7/2009 | Chang | |
| 7,566,327 B2 | 7/2009 | Mathias | |
| 7,578,805 B2 | 8/2009 | Hwang | |
| 7,597,681 B2 | 10/2009 | Sutton et al. | |
| 7,611,485 B2 | 11/2009 | Furgeson | |
| 7,611,487 B2 | 11/2009 | Woehr et al. | |
| 7,611,499 B2 | 11/2009 | Woehr et al. | |
| 7,618,395 B2 | 11/2009 | Furgeson | |
| 7,625,360 B2 | 12/2009 | Woehr et al. | |
| 7,637,887 B2 | 12/2009 | Woehr | |
| 7,651,476 B2 | 1/2010 | Kohler | |
| 7,670,317 B2 | 3/2010 | Cindrich et al. | |
| 7,713,243 B2 | 5/2010 | Hillman | |
| 7,731,687 B2 | 6/2010 | Menzi et al. | |
| 7,731,692 B2 | 6/2010 | Moos et al. | |
| 7,736,332 B2 | 6/2010 | Carlyon et al. | |
| 7,736,339 B2 | 6/2010 | Woehr et al. | |
| 7,744,567 B2 | 6/2010 | Glowacki et al. | |
| 7,753,877 B2 | 7/2010 | Bialecki et al. | |
| 7,798,994 B2 | 9/2010 | Brimhall | |
| 7,806,849 B2 | 10/2010 | Woehr et al. | |
| 7,828,773 B2 | 11/2010 | Swisher et al. | |
| 7,828,774 B2 | 11/2010 | Harding et al. | |
| 7,850,650 B2 | 12/2010 | Breitweiser | |
| 7,871,397 B2 | 1/2011 | Schraga | |
| 7,905,857 B2 | 3/2011 | Swisher | |
| 7,927,314 B2 | 4/2011 | Kuracina et al. | |
| 7,931,622 B2 | 4/2011 | Beling et al. | |
| 7,935,080 B2 | 5/2011 | Howell et al. | |
| 7,963,943 B2 | 6/2011 | Fiser | |
| 7,972,313 B2 | 7/2011 | Woehr et al. | |
| 7,976,498 B2 | 7/2011 | Swisher et al. | |
| 7,988,664 B2 | 8/2011 | Fiser et al. | |
| 8,038,647 B2 | 10/2011 | Harding et al. | |
| 8,048,036 B2 | 11/2011 | Woehr et al. | |
| 8,057,431 B2 | 11/2011 | Woehr et al. | |
| 8,066,675 B2 | 11/2011 | Cindrich et al. | |
| 8,096,977 B2 | 1/2012 | Ayiyama et al. | |
| 8,162,904 B2 | 4/2012 | Takano et al. | |
| 8,273,056 B2 | 9/2012 | Kuracina et al. | |
| 8,298,180 B2 | 10/2012 | Meehan et al. | |
| 8,672,895 B2 | 3/2014 | Kuracina et al. | |
| 8,764,711 B2 | 7/2014 | Kuracina et al. | |
| 8,821,439 B2 | 9/2014 | Kuracina et al. | |
| 2002/0151850 A1 | 10/2002 | Ferguson et al. | |
| 2003/0144627 A1 | 7/2003 | Woehr et al. | |
| 2003/0199827 A1 | 10/2003 | Thorne | |
| 2003/0220612 A1 | 11/2003 | Hiejima | |
| 2004/0049155 A1 | 3/2004 | Schramm | |
| 2004/0049163 A1* | 3/2004 | Murashita | 604/263 |
| 2007/0027429 A1 | 2/2007 | Kuracina et al. | |
| 2007/0100297 A1 | 5/2007 | Woehr et al. | |
| 2007/0112305 A1 | 5/2007 | Brimhall | |
| 2008/0119795 A1 | 5/2008 | Erskine | |
| 2009/0054852 A1 | 2/2009 | Takano et al. | |
| 2009/0216201 A1 | 8/2009 | Meehan et al. | |
| 2009/0312711 A1 | 12/2009 | Brimhall | |
| 2010/0106092 A1 | 4/2010 | Tanabe et al. | |
| 2010/0137803 A1 | 6/2010 | Funamura et al. | |
| 2010/0191188 A1 | 7/2010 | Harding et al. | |
| 2010/0191189 A1 | 7/2010 | Harding et al. | |
| 2010/0204654 A1 | 8/2010 | Mulholland et al. | |
| 2010/0222745 A1 | 9/2010 | Burkolz | |
| 2010/0222746 A1* | 9/2010 | Burkholz | 604/164.08 |
| 2010/0228197 A1 | 9/2010 | Murashita et al. | |
| 2010/0249707 A1 | 9/2010 | Woehr et al. | |
| 2010/0331781 A1 | 12/2010 | Millerd et al. | |
| 2011/0046555 A1 | 2/2011 | Abe et al. | |
| 2011/0060286 A1 | 3/2011 | Tanabe et al. | |
| 2011/0125096 A1 | 5/2011 | Baid | |
| 2011/0166526 A1 | 7/2011 | Kuracina et al. | |
| 2011/0208124 A1 | 8/2011 | Rhad et al. | |
| 2011/0213307 A1 | 9/2011 | Kawai et al. | |
| 2011/0282285 A1 | 11/2011 | Blanchard et al. | |
| 2012/0220956 A1 | 8/2012 | Kuracina et al. | |
| 2012/0220957 A1 | 8/2012 | Kuracina et al. | |
| 2013/0138015 A1 | 5/2013 | Kuracina et al. | |
| 2013/0204207 A1 | 8/2013 | Kuracina et al. | |
| 2014/0012210 A1 | 1/2014 | Kuracina et al. | |
| 2014/0025009 A1 | 1/2014 | Erskine | |
| 2014/0221931 A1 | 8/2014 | Kuracina et al. | |

(56) References Cited

U.S. PATENT DOCUMENTS

| | | | |
|---|---|---|---|
| 2014/0371677 A1 | 12/2014 | Kuracina et al. | |
| 2015/0126943 A1 | 5/2015 | Kuracina et al. | |

FOREIGN PATENT DOCUMENTS

| | | | |
|---|---|---|---|
| EP | 0554841 | A1 | 8/1993 |
| EP | 0743073 | A2 | 11/1996 |
| EP | 1344544 | | 12/2001 |
| EP | 1604700 | A1 | 12/2005 |
| EP | 2075029 | A1 | 7/2009 |
| EP | 2127692 | A1 | 12/2009 |
| GB | 2252046 | A | 7/1992 |
| GB | 2292525 | A | 2/1996 |
| JP | 4252799 | | 12/2001 |
| JP | 4252799 | | 4/2009 |
| SE | 920131168 | | 10/1993 |
| WO | WO8910767 | A1 | 11/1989 |
| WO | WO9400172 | A1 | 1/1994 |
| WO | WO9742989 | | 11/1997 |
| WO | 9908742 | A1 | 2/1999 |
| WO | WO2005087296 | A1 | 9/2005 |
| WO | 2006096633 | A1 | 9/2006 |
| WO | WO2008021132 | A1 | 2/2008 |
| WO | WO2009116080 | A2 | 9/2009 |
| WO | WO2010127846 | A1 | 11/2010 |
| WO | WO2011000570 | A1 | 1/2011 |
| WO | 2012075402 | A1 | 6/2012 |
| WO | 2012075421 | A1 | 6/2012 |
| WO | WO2012118718 | A1 | 9/2012 |
| WO | 2012139034 | A1 | 10/2012 |

OTHER PUBLICATIONS

International Search Report and Written Opinion of the International Searching Authority Search Report Application No. PCT/US2013/056801 issued by USPTO, Alexandria, Virginia dated Feb. 7, 2014.
Extended European Search Report for EP 12752683.8 issued by the European Patent Office, Berlin, Germany dated Mar. 6, 2014.
International Preliminary Report on Patentability International Application No. PCT/US2012/026659 issued by the International Bureau of WIPO, Geneva, Switzerland dated Sep. 3, 2013; which includes the Written Opinion of the International Searching Authority originally issued on Jul. 2, 2012, by USPTO, Alexandria, Virginia.
Notification Concerning Transmittal of International Preliminary Report on Patentability dated Mar. 12, 2015 issued by the International Bureau of WIPO, Geneva, Switzerland with the International Preliminary Report on Patentability International Application No. PCT/US2013/056801 issued by the International Bureau of WIPO, Geneva, Switzerland dated Mar. 3, 2015; which includes the Written Opinion of the International Searching Authority originally issued on Feb. 7, 2014 by USPTO, Alexandria, Virginia.

* cited by examiner

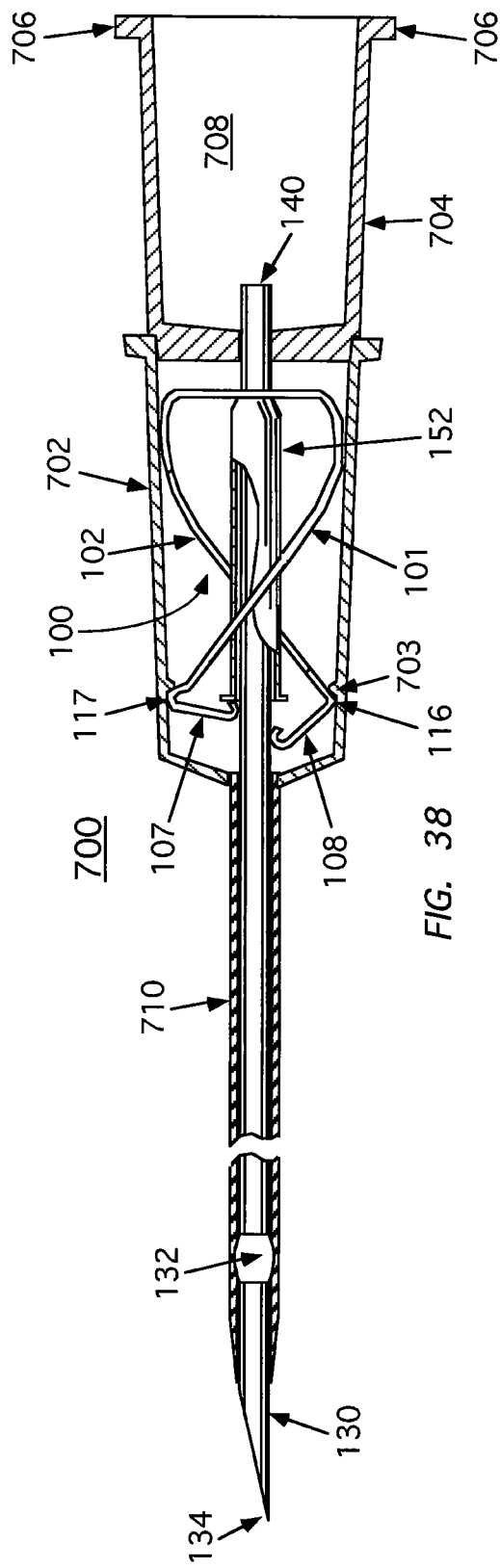
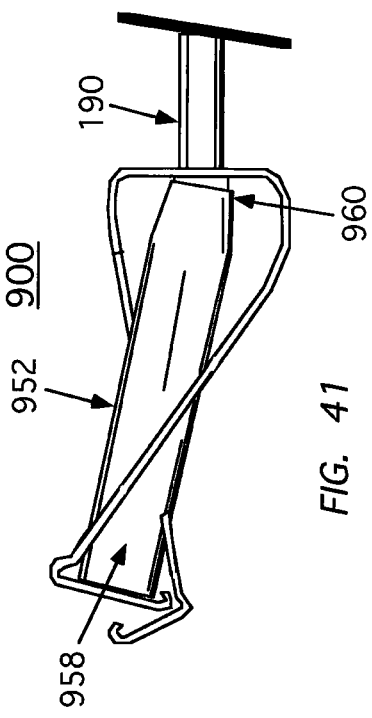

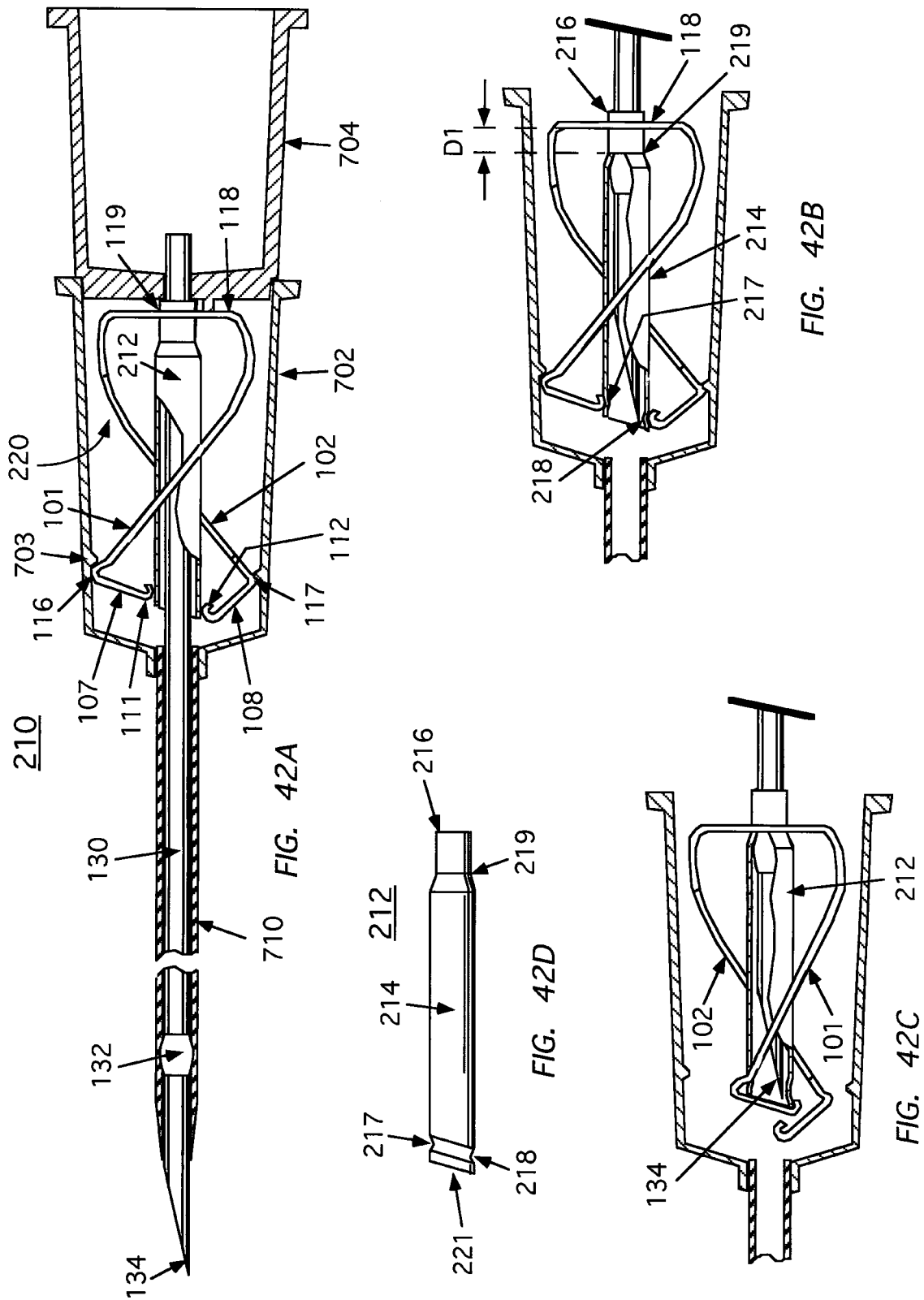

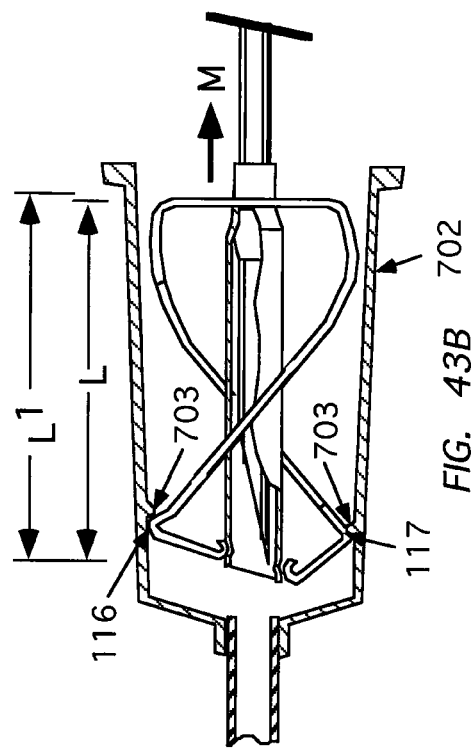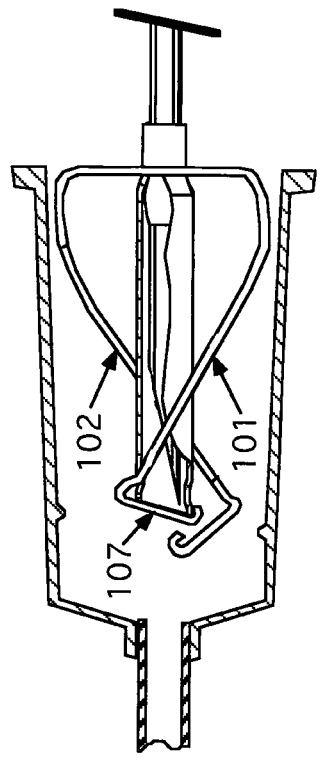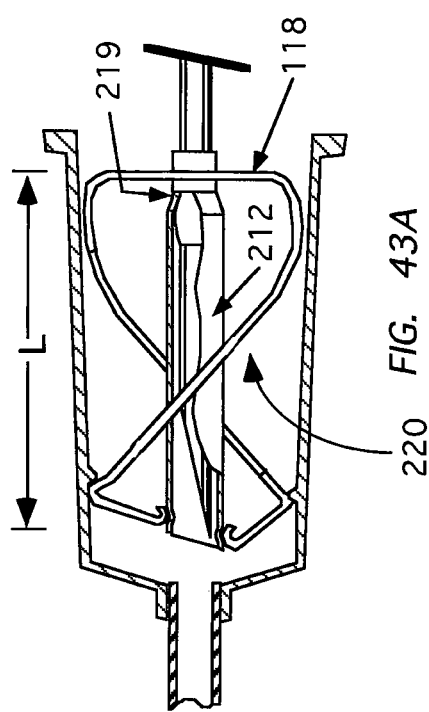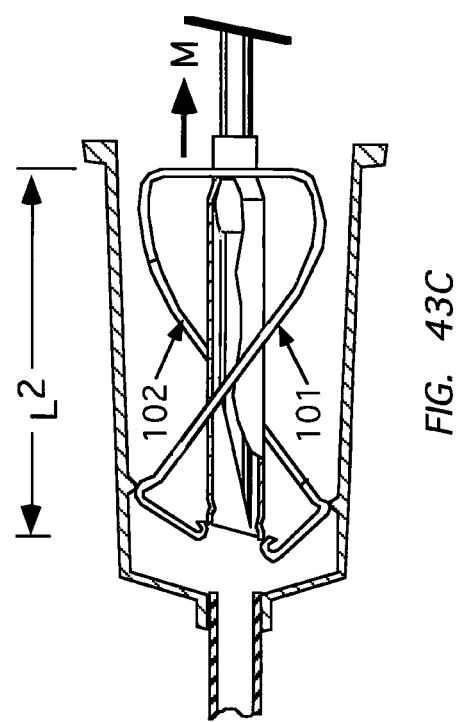

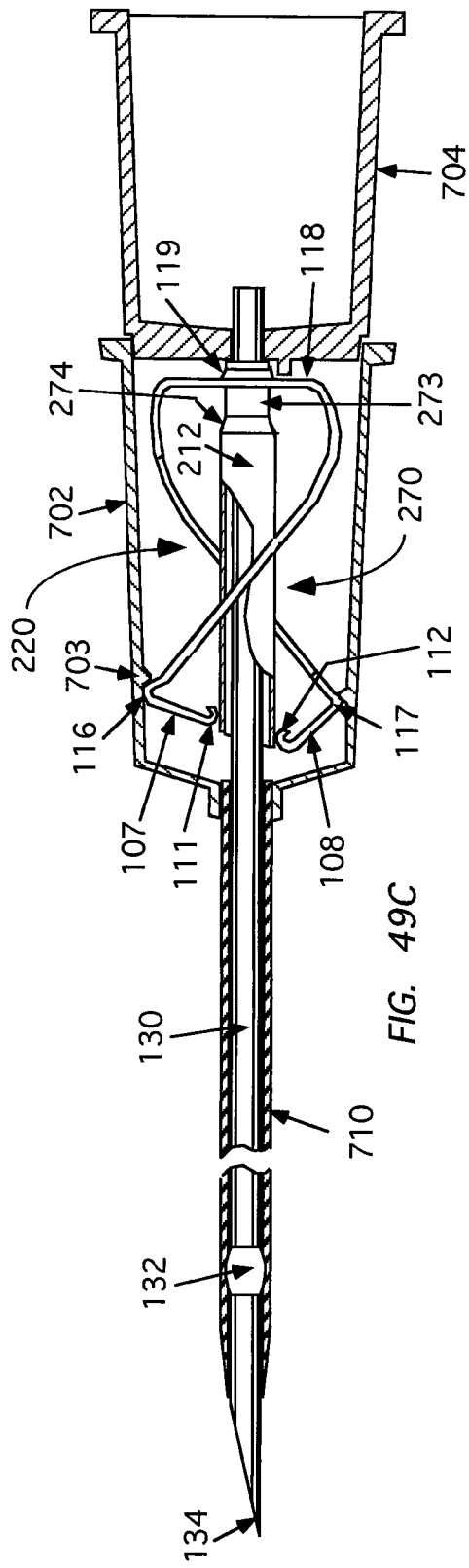
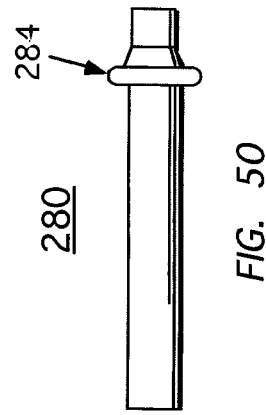
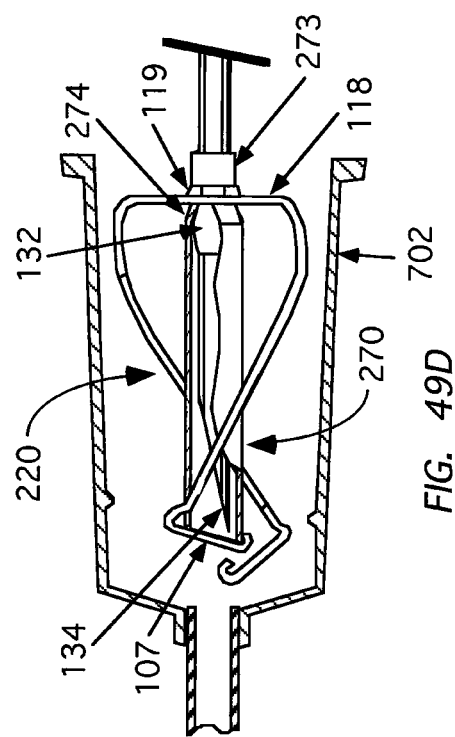
FIG. 49C
FIG. 49D
FIG. 50

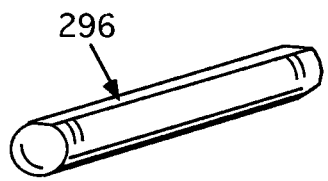
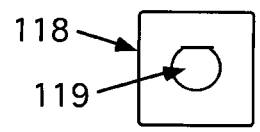
FIG. 56A             FIG. 56B
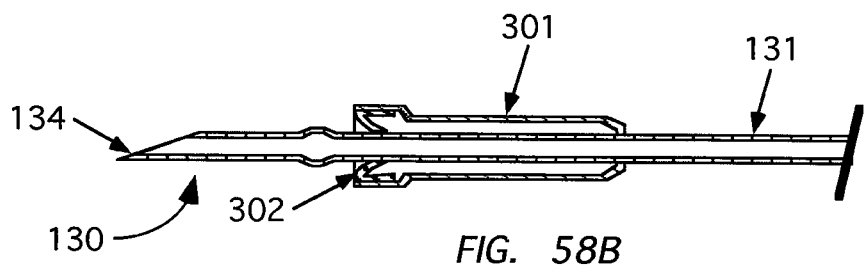
FIG. 58B
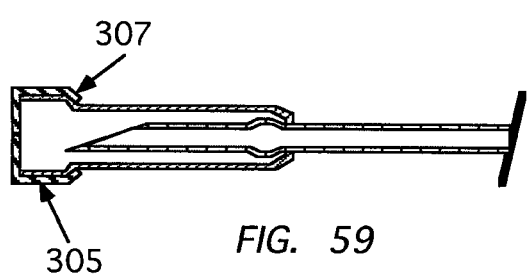
FIG. 59
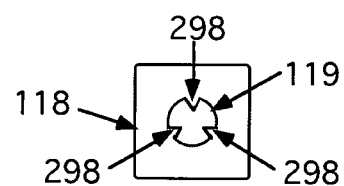
FIG. 57A
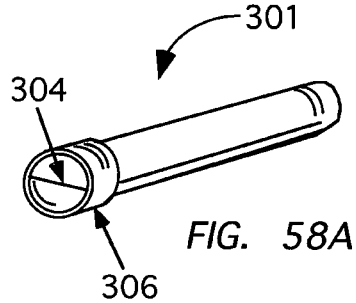
FIG. 58A
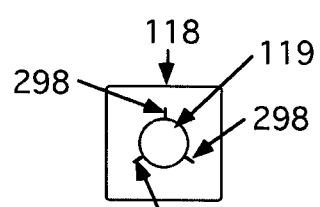
FIG. 57B
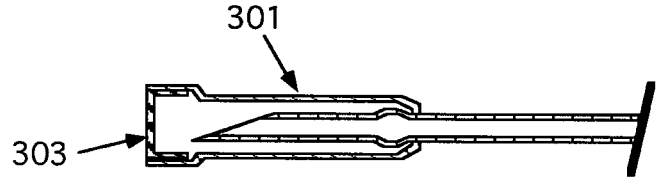
FIG. 58C

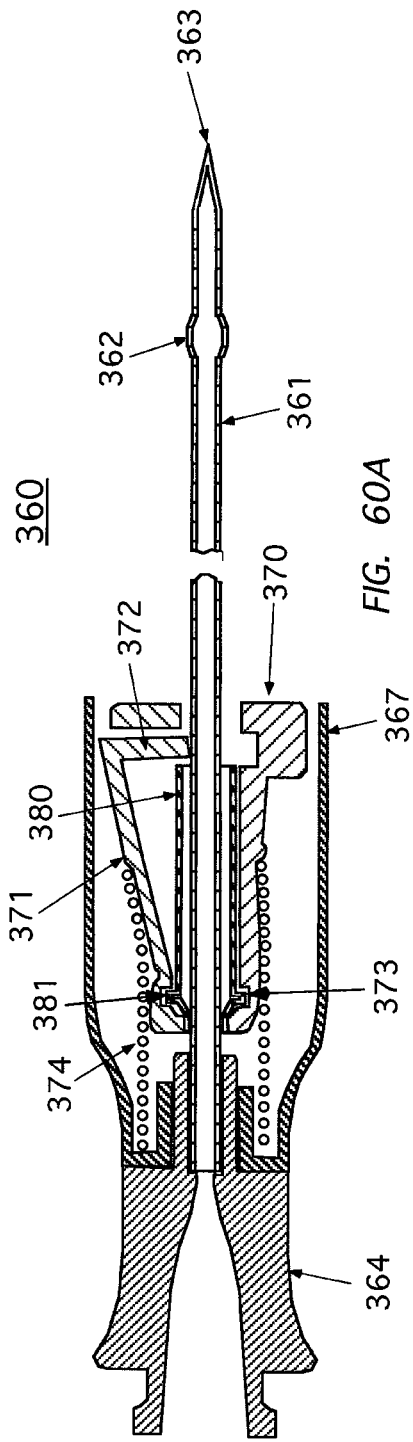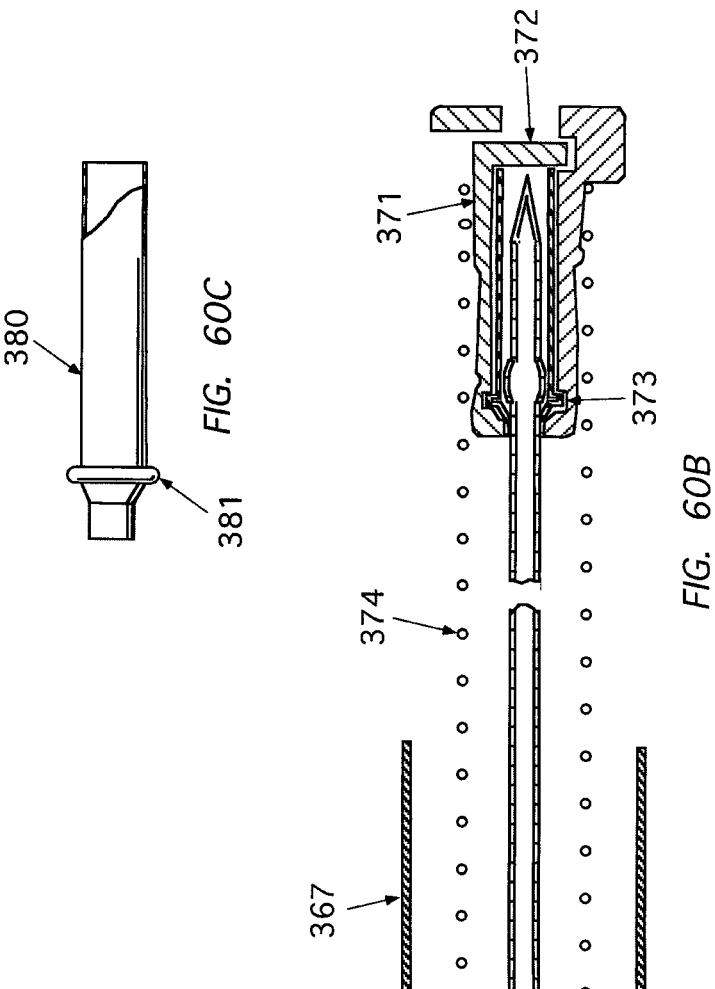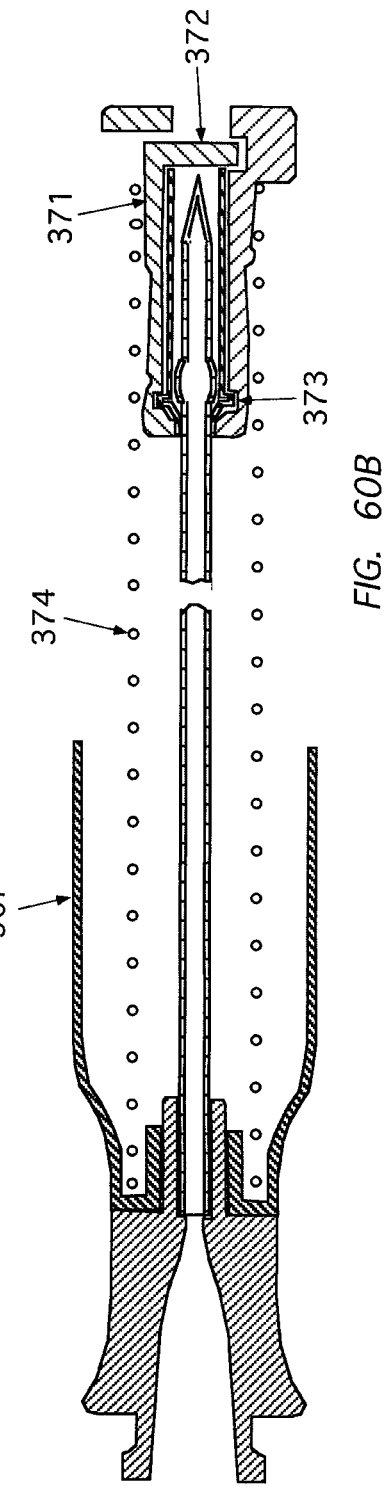
FIG. 60A
FIG. 60C
FIG. 60B

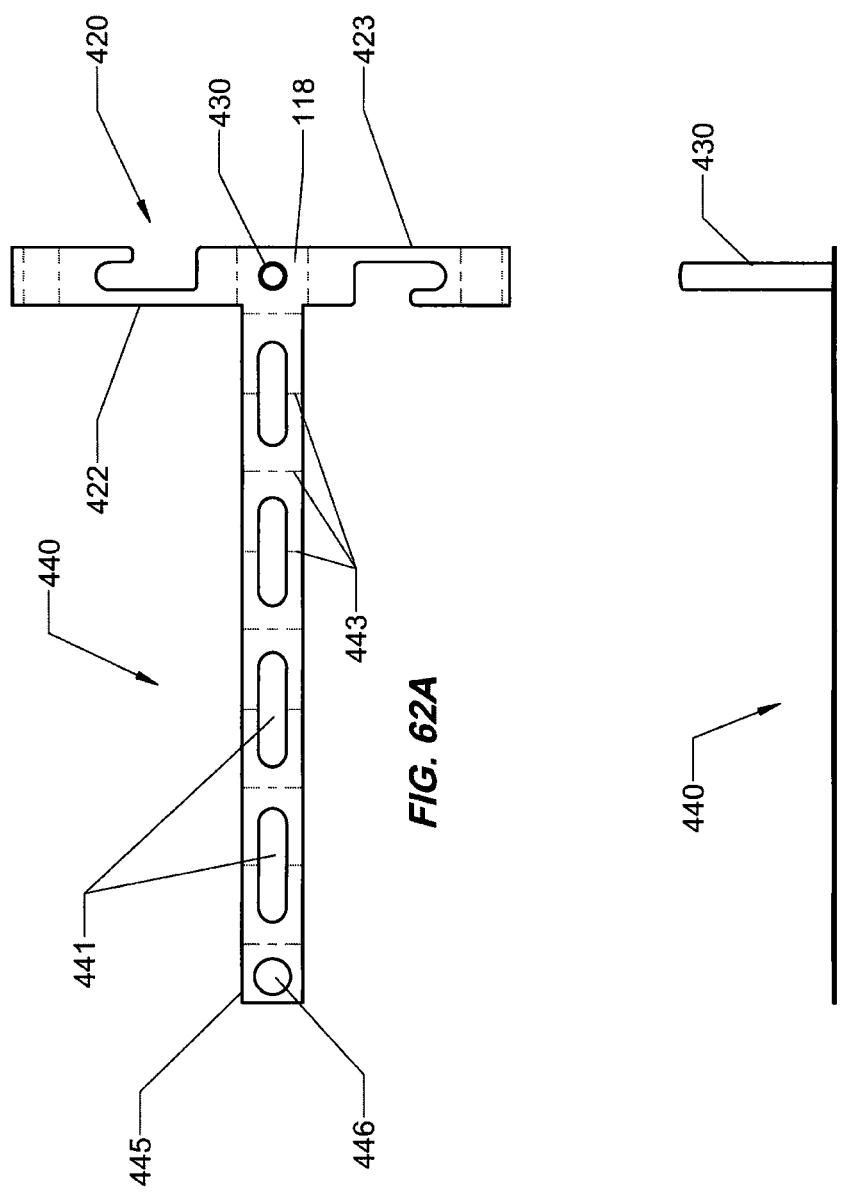

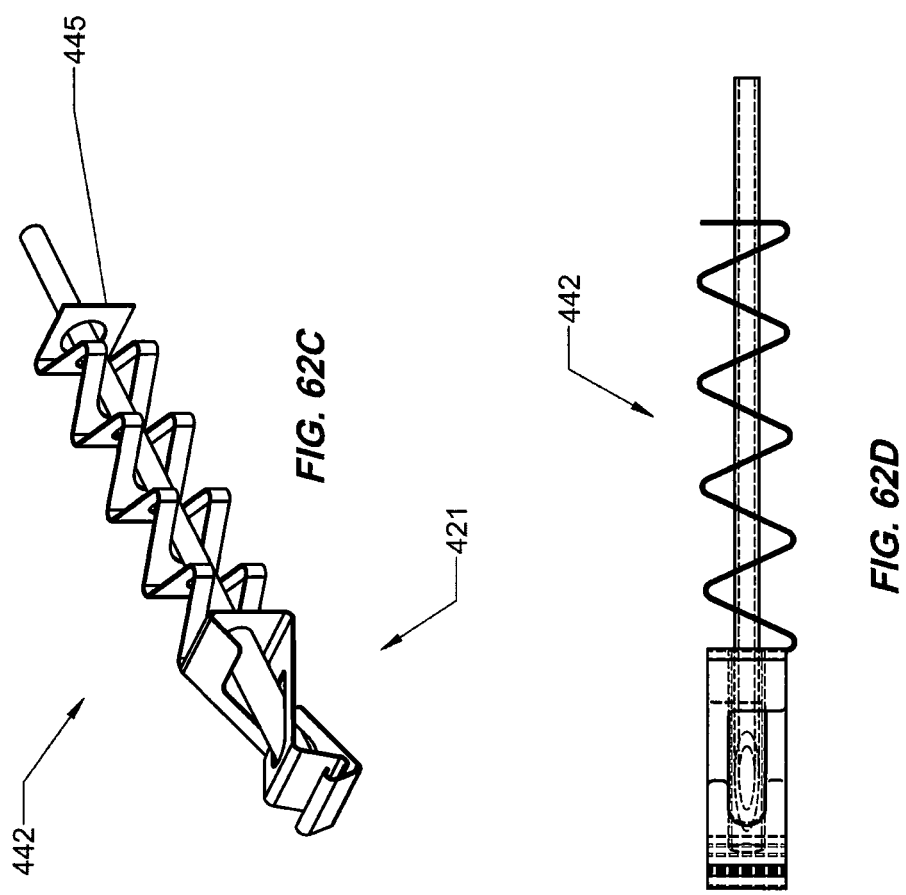

NEEDLE GUARD

CROSS-REFERENCE TO RELATED APPLICATIONS

This application is a continuation-in-part of U.S. application Ser. No. 13/037,164, filed Feb. 28, 2011.

FIELD

The inventions disclosed herein relate to safety needle devices.

BACKGROUND

A number of U.S. Patents describe safety IV catheters where the distal tip of the needle is provided with a degree of protection after use, including but not limited to: McLees, U.S. Pat. No. 5,135,504; Erskine, U.S. Pat. No. 5,797,880; Woehr, et al., U.S. Pat. No. 6,287,278; Bialecki, et al., U.S. Pat. No. 6,652,486; McGurk, U.S. Pat. No. 7,291,130; Rhad, et al., U.S. Pat. No. 7,303,548; Menzi, et al., U.S. Pat. No. 7,731,687; and Harding, et al., U.S. Pat. No. 7,828,774.

These prior art safety catheters all exhibit one or more drawbacks that could potentially place healthcare workers, or others at risk for a percutaneous or non-percutaneous blood or bodily fluids exposure after the needle tip is covered by the safety mechanism. Although the needle tip itself is covered after use on a number of available safety IV catheters, the entirety of the needle tip is not fully contained after use which could result in blood or fluid residing in the distal end of the needle lumen leaking, or otherwise escaping, into the workplace and contacting a healthcare provider. For example, splattered blood could enter a mucous membrane region of the eyes, nose or mouth of any healthcare personnel within close proximity to the splatter. The exposure should then be reported and post exposure treatment, prophylaxis and follow up would occur, incurring costs to the institution and worry to the individual exposed to the blood. Additionally, some commercially available needle guards can be easily defeated by an inadvertent incident where the components no longer protect or shield the contaminated tip.

FIGS. 1-5 illustrate a safety needle guard 10 similar to the one disclosed in U.S. Pat. No. 6,287,278. The needle guard 10 is constructed from a single piece of material as shown in FIG. 1 and formed to assume the configurations depicted in FIGS. 2-5 during use. FIGS. 2 and 3 show different side views of the needle guard 10 in a ready position where the distal tip 18 of the needle 15 is unprotected. FIGS. 4 and 5 show the different side views of the needle guard 10 after the needle guard has been activated to cover the distal tip 18. As shown in FIGS. 4 and 5, although the extreme distal tip 18 of needle 15 is protected, the open lumen 17 in the bevel region 16 of the needle remains exposed. Another problem associated with the needle guard 10 is that forces may be applied to the needle guard arms 11 and 12 at locations to cause the distal arm segments 13 and 14 to be urged outward. This creates a risk of having the distal arm segments 13 and/or 14 being moved away from protecting the distal tip 18.

SUMMARY

According to some implementations an intravenous (IV) catheter assembly is provided comprising: a catheter hub comprising a hollow body having a proximal end and a distal end, the hollow body defining an interior space; a catheter having a proximal end and a distal end, the proximal end of the catheter coupled to the proximal end of the catheter hub; a needle having a needle shaft and a distal tip, the needle moveable between a ready position and a retracted position, in the ready position the distal tip of the needle extending distally from the distal end of the catheter, in the retracted position the distal tip of the needle residing in a position proximal to the proximal end of the catheter, the needle shaft having a change in profile; and a needle guard comprising an arm that extends distally from a base having an aperture formed therein, the needle guard slideably mounted on the needle shaft with the needle shaft passing through the aperture formed in the base, the aperture sized to engage with the change in profile of the needle shaft to limit the proximal movement of the needle with respect to the needle guard, the arm comprising a resilient material and having a proximal section, a mid-section and a distal section, the distal section of the arm resides and is urged against a side of the needle shaft when the needle is in the ready position, the needle guard further comprising an elongate member having a through passage extending between a proximal end and a distal end of the elongate member, the elongate member extending distally from a position at or near the base and slideable along the needle shaft as the needle is moved between the ready position and the retracted position, the elongate member having a length such that substantially coincident with the change in profile engaging the aperture in the base the entirety of the distal tip of the needle is positioned to reside within the through passage of the elongate member and the distal section of the arm disengage with the needle shaft to move radially inward to at least partially cover the distal end of the elongate member, the elongate member being sufficiently rigid to restrict longitudinal movement of the needle with respect to the needle guard when the distal section of the arm at least partially covers the distal end of the elongate member.

According to other implementations an IV catheter assembly is provided comprising: a catheter hub comprising a hollow body having a proximal end and a distal end, the hollow body defining an interior space; a catheter having a proximal end and a distal end, the proximal end of the catheter coupled to the proximal end of the catheter hub; a needle having a needle shaft and a distal tip, the needle moveable between a ready position and a retracted position, in the ready position the distal tip of the needle extending distally from the distal end of the catheter, in the retracted position the distal tip of the needle residing in a position proximal to the proximal end of the catheter, the needle shaft having a change in profile; and a needle guard comprising first and second arms that extend distally from a base having an aperture formed therein, the needle guard slideably mounted on the needle shaft with the needle shaft passing through the aperture formed in the base, the aperture sized to engage with the change in profile of the needle shaft to limit the proximal movement of the needle with respect to the needle guard, each of the first and second arms comprising a resilient material and having a proximal section, a mid-section and a distal section, the first and second arms extending from different positions of the base and intersecting one another along their mid-sections so that the distal sections of the first and second arms reside and are urged against opposite sides of the needle shaft when the needle is in the ready position, the needle guard further comprising an elongate member having a through passage extending between a proximal end and a distal end of the elongate member, the elongate member extending distally from a position at or near the base and slideable along the needle shaft as the needle is moved between the ready position and the retracted position, the elongate member having a length such that substantially coincident with the change in profile engaging the aperture in the base the entirety of the distal tip of the needle is positioned to reside within the through passage of the elongate member and the distal section of at least one of the first and second arms disengages with the needle shaft and moves radially inward to at least partially cover the distal end of the elongate member, the elongate member being sufficiently rigid to restrict longitudinal movement of the needle with respect to the needle guard when the distal section of at least one of the first and second arms at least partially covers the distal end of the elongate member.

According to some implementations the needle guard comprises a unitary structure with the elongate member being integrally formed with the base of the needle guard.

According to some implementations the needle is stopped in the retracted position by component or feature incorporated with, or otherwise situated, at or near the distal end of the elongate member.

According to some implementations a proximal section of the elongate member comprises a reduced diameter portion and/or a frustoconical portion useable to assist in self-centering the needle on the needle guard.

According to another implementation a safety needle device is provided comprising: a needle having a needle shaft and a distal tip, the needle shaft having a change in profile near the distal tip; a needle guard transitional between a ready state where the distal tip of the needle is in an unprotected state and an activated state where the distal tip of the needle is in a protected state, the needle guard comprising an arm that extends distally from a base having an aperture formed therein, the needle guard slideably mounted on the needle shaft with the needle shaft passing through the aperture formed in the base, the arm comprising a resilient material and having a proximal section, the needle guard further comprising an elongate member extending distally from a position at or near the base and slideable along the needle shaft as the needle guard is moved between the ready position and the activated position, the elongate member having a proximal end, a distal end and a through passage extending therebetween, a first portion of the through passage located at or near the proximal end of the elongate member is sized to engage with the change in profile of the needle shaft to limit proximal movement of the needle with respect to the needle guard, the elongate member having a length such that when the change in profile engages the first portion of the through passage the entirety of the distal tip of the needle is positioned to reside within the through passage of the elongate member, the elongate member comprising a proximal section and a distal section, the proximal section of the elongate member disposed within the aperture of the base with the base being slideable on the proximal section of the elongate member between a first position when the needle guard is in the ready state and a second position distal to the first position when the needle guard is in the activated state, when the needle guard is in the ready state the distal section of the arm resides on the distal section of the elongate member near the distal end of the elongate member where at least a portion of the distal section of the arm is urged against an outer side of the elongate member, the needle guard is configured such that as it transitions from the ready state to the activated state, upon a movement of the base from the first position to the second position, the distal section of the arm moves distally along the outer side of the distal section to the distal end of the elongate member where it moves radially inward to at least partially cover the distal end of the elongate member, the elongate member being sufficiently rigid to restrict longitudinal movement of the needle with respect to the needle guard when the distal section of the arm at least partially covers the distal end of the elongate member.

In other implementations needle guards are provided wherein biasing members act on the one or more arms of the needle guards to assist in urging the arms against the needle shaft or elongate member, as the case may be, when the needle guards are in the ready state.

Many other implementations are disclosed and contemplated herein. Moreover, it is important to note that the inventions are not limited to safety IV catheters, but are applicable to any of a variety of needle products including but not limited to syringes, guidewire introducers, blood collection devices, etc.

BRIEF DESCRIPTION OF THE DRAWINGS

FIG. 38 illustrates a safety intravenous catheter assembly according to one implementation;

FIG. 41 illustrates a needle guard assembly according to another implementation;

FIGS. 42A-42D illustrate a safety intravenous catheter assembly according to another implementation;

FIGS. 43A-43D illustrate a manner in which the needle guard of FIG. 42 may activate;

FIGS. 49A-49D illustrate a safety intravenous catheter assembly according to another implementation;

FIG. 50 shows an elongate member according to one implementation;

FIG. 56A illustrates an elongate member according to one implementation;

FIG. 56B illustrated a base of a spring clip according to implementation with a key hole provided for receiving the proximal end of the elongate member of FIG. 56A;

FIGS. 57A and 57B illustrate the base of a spring clip according to other implementation;

FIGS. 58A-58C illustrate an elongate member having a seal member situated at its distal end;

FIG. 59 illustrates a seal member according to another implementation;

FIGS. 60A-60C illustrate a needle guard assembly according to another implementation incorporated within a guidewire introducer;

FIGS. 62A-62D illustrate a needle guard assembly according to another implementation wherein spring means is integrally formed with the spring clip;

DETAILED DESCRIPTION

Figure 1:
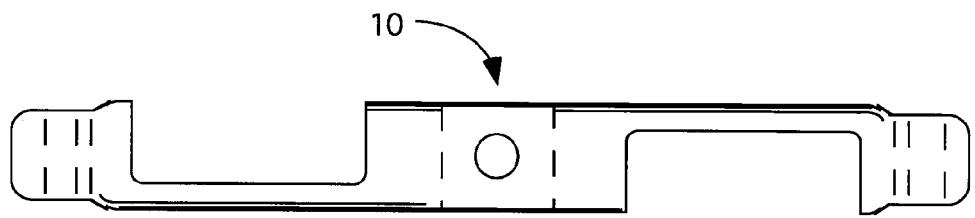
FIGS. 1 through 5 illustrate a prior art needle guard.
Figure 2:
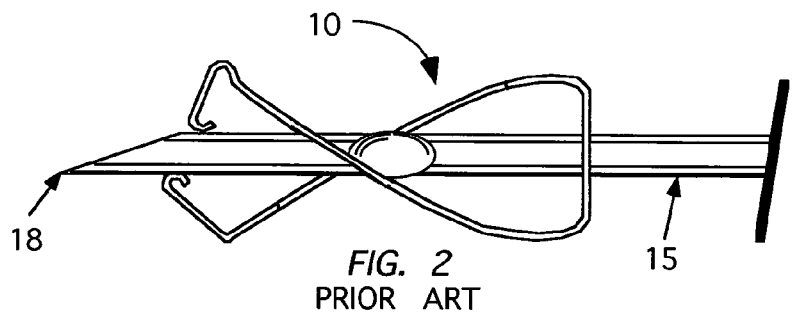
Figure 3:
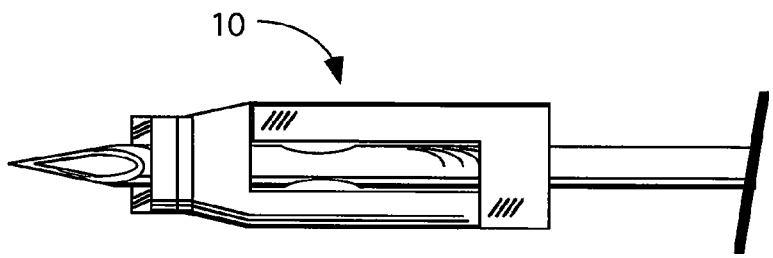
Figure 4:
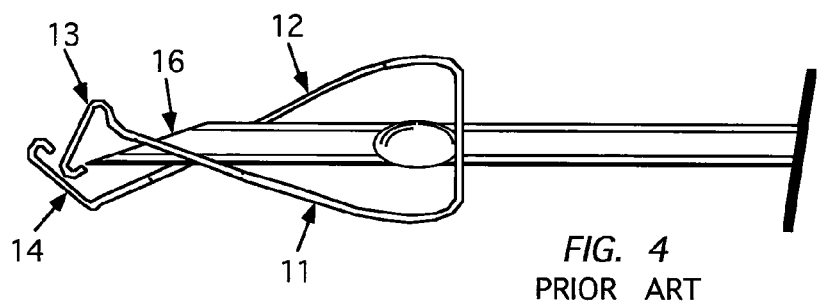
Figure 5:
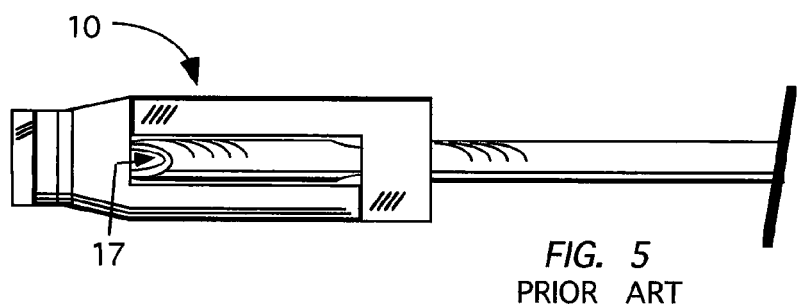
Figure 6A:
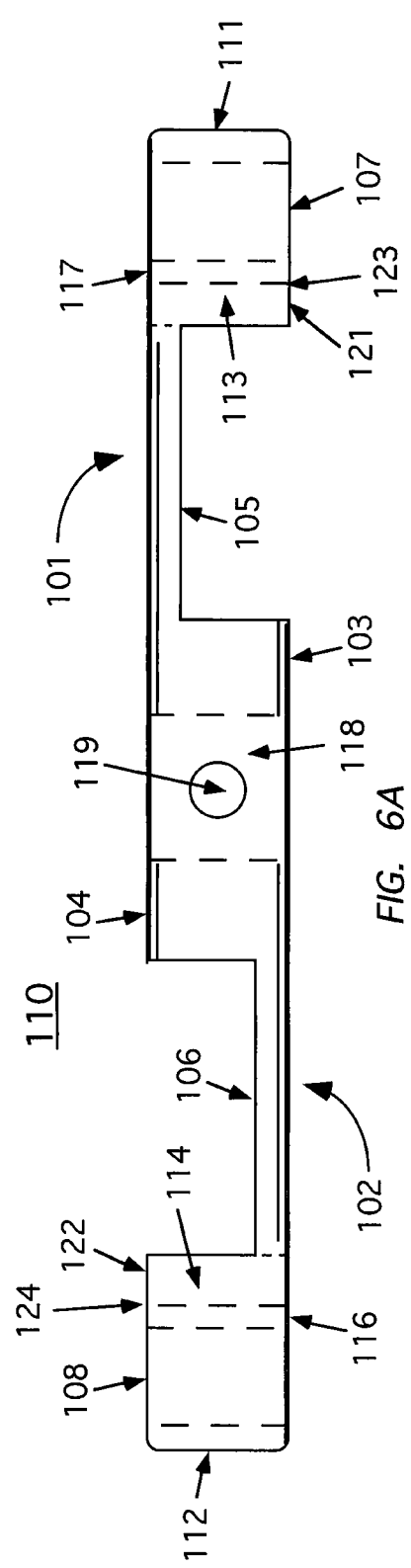
FIGS. 6A through 6C illustrate implementations of a flat stock usable to form needle guards disclosed and contemplated herein.
Figure 6B:
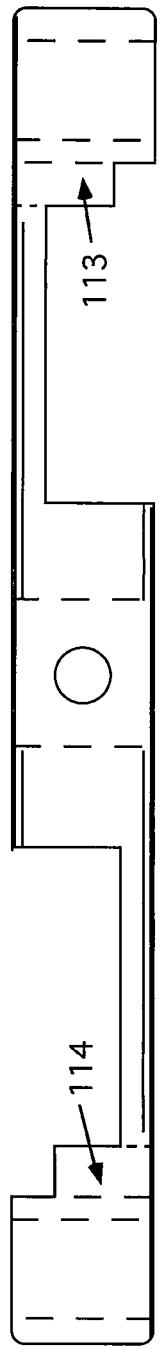
Figure 6C:
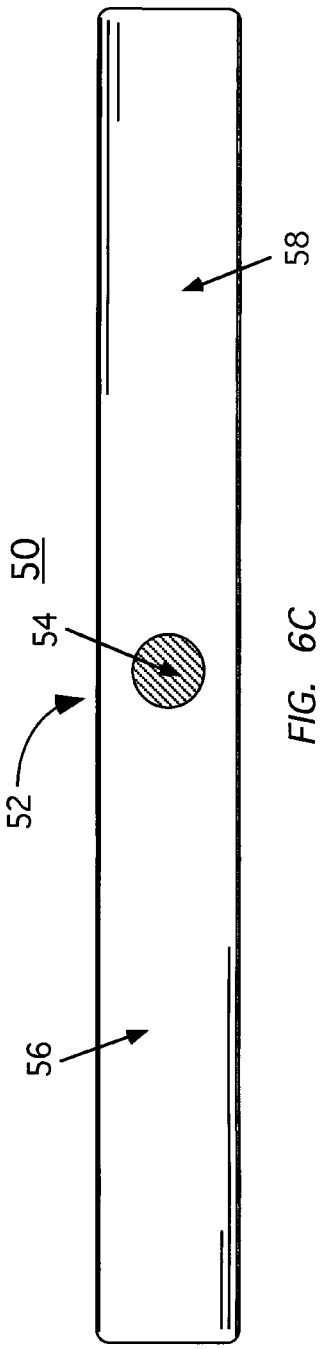
Figure 7:
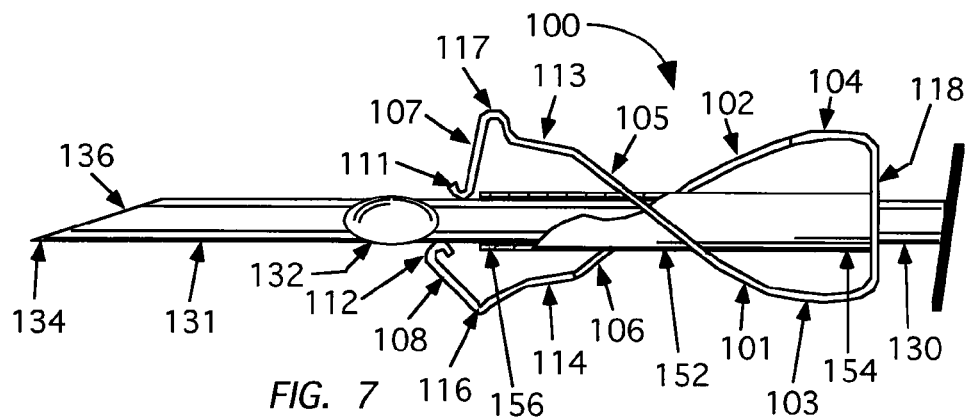
FIGS. 7 through 10 illustrate a needle guard assembly according to one implementation.
Figure 8:
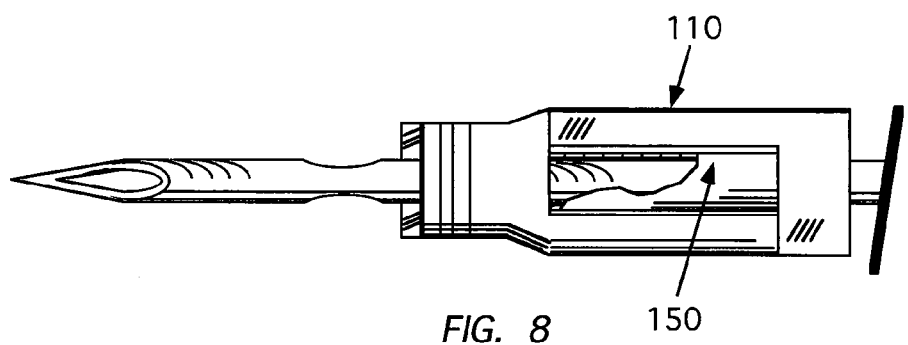
Figure 9:
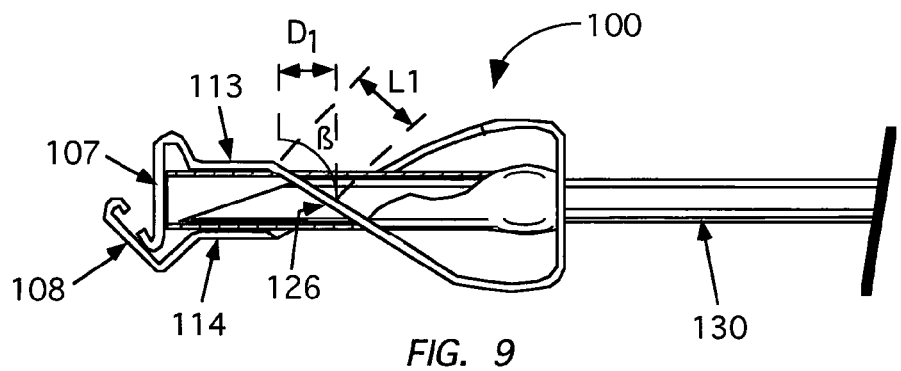
Figure 10:
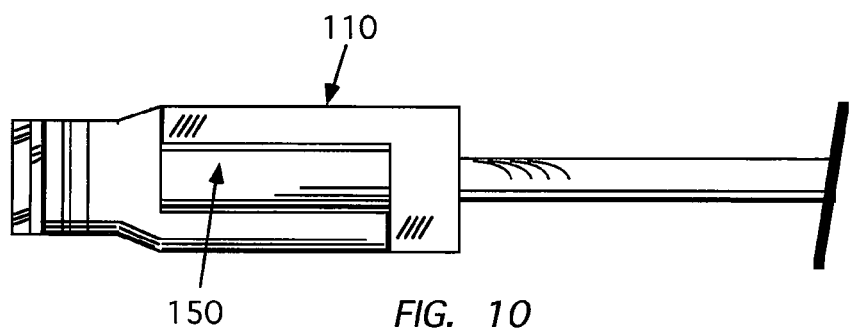
Figure 11:
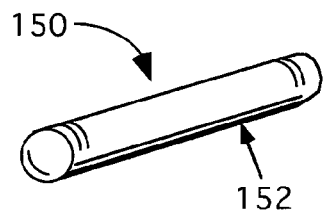
FIGS. 11 through 17 illustrate protective elongate members according to various implementations.
Figure 12:
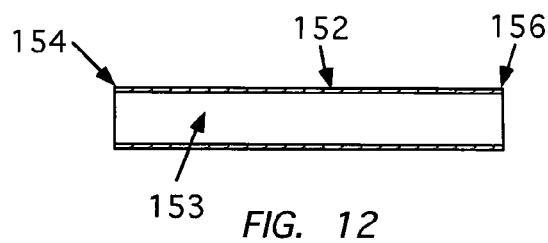

FIGS. 6 through 11 illustrate needle guards 100 according to some implementation. According to one implementation, a first portion 110 of the needle guard 100 is manufactured from a flat material having resilient characteristics, as shown in FIG. 6A or 6B, and shaped to assume the in-use configurations shown in FIGS. 7-10, whereas a second portion 150 (see FIGS. 11 and 12) of the needle guard 100 defines an elongate member 152 having a through passage 153 extending between a proximal end 154 and an distal end 156. FIGS. 7 and 8 show different side views of the needle guard 100 situated in a first axial position on a needle 130 with the distal end 134 of the needle being unprotected. FIGS. 9 and 10 show the different side views with the needle guard 100 situated in a second axial position on the needle 130 with the distal end 134, including the entirety of the bevel 136, being protected.

In one implementation, the first portion 110 of the needle guard 100 has first and second resilient arms 101 and 102, respectively, with each of the arms comprising a proximal section 103, 104, a mid-section 105, 106 and a distal section 107, 108. The first and second arms 101, 102 extend distally from different positions of a base 118 and intersect one another along their mid-sections 105, 106 so that lip segments 111, 112 of the distal sections 107, 108 reside at and are urged against opposite sides of the needle shaft 131 when the needle guard is situated in the first axial position. The first portion 110 of the needle guard 100 is slideably mounted on the needle shaft 131 with the needle shaft passing through an aperture 119 formed in the base 118. In one implementation the aperture 119 is sized to engage with a change in profile 132 on the needle to limit movement between the needle 130 and the needle guard 100 in a first direction when the needle guard 100 is situated in the second axial position. The change in profile 132 may comprises a crimp on the needle shaft 131 or any other form of enlargement such as those depicted in FIGS. 33 and 35.

As shown in FIG. 7, the elongate member 152 is situated in the needle guard 100 with its proximal end 154 positioned at or near the base 118, and with its distal end 156 positioned at or near lip segment 111 of arm 101 when the needle guard is in the ready position. In some implementations the elongate member 152 is substantially coaxial with the needle 130 with the diameter or cross-sectional area of the through passage 153 being sufficiently large to permit the elongate member to slide over the change in profile 132. In other implementations the elongate member 152 is substantially coaxial with the needle 130 with the diameter or cross-sectional area of all or a proximal portion of the through passage 153 being smaller than a cross-sectional area of the change in profile 132. In implementations where all or a portion of the through passage 153 has a cross-sectional area smaller than a cross-sectional area of the change in profile 132, the through passage 153 is made to be expandable over the change in profile 132, like, for example that shown in FIG. 9. In some implementations the sections of the elongate member 152 where the through passage 153 has a smaller cross-sectional area than the change in profile 132 are resilient to cause the cross-sectional area of the through passage 153 to contract inwardly after that portion of the through passage has crossed the change in profile. In some implementations, as discussed in more detail below, only a proximal portion of the expandable member 152 has a reduced cross-sectional area that is resiliently expandable over the change in profile 132. In use, the elongate member 152 travels axially along the shaft of the needle in conjunction with the first portion 110 of the needle guard 100. In some implementations the elongate member 152 rides with the first portion 110 of the needle guard with the proximal end 154 abutting the base 118. In other implementations the proximal end 154 of the elongate member 152 is attached to base 118. In other implementations, a proximal portion or the entire elongate member 152 is integral with the base 118.

FIGS. 9 and 10 show the needle guard 100 positioned on the needle 130 in the second axial position with the needle tip 134, including the entirety of the bevel 136, being covered. In one implementation, as the needle guard is advanced over the needle 130 and the lip segments 111 and 112 are moved distal to the needle tip 134, the needle guard 100 is stopped in the second axial position by the engagement of the change in profile 132 on the needle with the aperture 119 of base 118. Other stop implementations are disclosed below. The length of the elongate member 152 is selected so that substantially coincident with the change in profile 132 engaging, for example, the aperture 119 in base 118 the entirety of the distal tip 134 and bevel region 136 of needle 130 is positioned to reside within the through passage 153 and so that at least one of the distal sections 107, 108 of arms 101, 102 disengage with the needle to and advances to fully or at least partially cover the distal end 156 of the elongate member 152.

In one implementation, as shown in FIG. 7, the distal section 107 of arm 101 is configured to assume a first angle with respect to the needle axis when the needle guard 100 is positioned in a ready position and the distal section 108 of arm 102 is configured to assume a second angle with respect to the needle axis when the needle guard 100 is positioned in the ready position, the second angle being greater than the first angle. Further, as shown in FIG. 9, when the needle guard 100 is in the second axial position the distal section 107 of arm 101 is oriented and biased to assume a substantially perpendicular relationship with respect to the longitudinal axis of the elongate member 152. In some implementations the cross-sectional area of the distal section 107 is sufficient to cover the entirety of the distal end 156 of the elongate member 152. In other implementations, less than the entirety of the distal end 156 of the elongate member 152 is covered by distal section 107.

As mentioned above, the distal end 107 of arm 101 may be biased so that it applies a downward/proximally acting force on the distal end 156 of elongate member 152 when the needle guard 100 assumes the second axial position. In one implementation the bias is created by a resilient hinge in the region 117. The application of a downward/proximally acting force assists in the formation of a full or partial seal that may impede or prevent contaminants within the needle 130 and elongate member 152 lumens from leaking out of the needle guard 100 after it has assumed the second axial position. In some implementations, the distal end 108 of arm 102 is oriented and biased to assume an oblique angle with respect to the distal end 107 and to exert a force on the distal end 107 in a direction toward the distal end 156 of elongate member 152.

In implementations where the needle guard 100 forms a part of an intravenous catheter 700, as shown in FIG. 38, protrusions 117 and 116 may be formed on arms 101 and 102, respectively, to engage with one or more features 703 in the interior of the catheter hub 702 to releasably secure the needle guard 100 in the catheter hub when the catheter assembly 700 is in a ready position.

As mentioned above, a problem associated with prior art spring clip needle guard devices is that forces may be applied to parts of the spring clip arms to cause the distal arm sections to be urged outward. This creates a risk of the distal arm sections being moved away from protecting the needle tip after the needle guard has assumed a protected position. To address the problem, in some implementations the first portion 110 of the needle guard 100 comprises straight, or substantially straight, arm segments 113 and 114 that are disposed proximal to distal arm sections 107 and 108, respectively. As shown in FIG. 9, the arm segments 113 and 114 are arranged so that when the needle guard 100 assumes the second axial position on the needle 130, the arms segments 113 and 114 abut and are laterally disposed on opposite sides of the outer surface of the elongate member 152. Arm segments 113 and 114 are disposed to occupy positions between the distal sections 107, 108 and the intersection point 126 of the arms 101 and 102 when the needle guard is in the second axial position. In one implementation arm segments 113 and 114 are located adjacent to distal sections 107 and 108, respectively, and disposed a distance distal to the intersection point 126 of the arms 101 and 102. In one implementation the distance ($D_1$) segment 113 is distally spaced from the intersection point 126 is greater than or equal to $L_1 \sin \beta$, with L1 being the approximate distance between the intersection point 126 and the location arm 101 intersects the outer circumference of the elongate member 152 and β being the angle between arm 101 and a line running perpendicular to the longitudinal axis of elongate member 152 at the intersection point 126. Although not required, segment 114 is preferably distally spaced from the intersection point 126 so to be substantially longitudinally aligned with segment 113.

In some implementations segments 113 and 114 have substantially the same width as distal sections 107 and 108, respectively. In other implementations segments 113 and 114 have widths that are less than those of distal sections 107 and 108, respectively, as shown in FIG. 6B. In other implementations, one or both of segments 113 and 114 may comprise arcuate portions that at least partially conform to portions of the outer curvature of the elongate member 152. An advantage of such a configuration is that the at least partial conformability of segments 113, 114 with the outer surface of elongate member 152 acts to stabilize the segments about the elongate member in the event improper forces are applied to either or both of arms 101 and 102. In other words, the at least partial conformability reduces the likelihood of arms 101 and/or 102 slipping sideways on the outer surface of elongate member 152 when improper forces are applied to arms 101 and/or 102. As an example, and with reference to FIG. 6A, the outer edges 121 and 122 of segments 113 and 114 may be curved inward along cut-lines 123 and 124, respectively, to assume a partially curved configuration.

The first portion 110 and second portion 150 of the needle guard 100 may assume any of a variety of configurations. Turning again to FIGS. 6A and 6B, in one implementation the arm mid-sections 105 and 106 are narrowed sufficiently to accommodate the elongate member 152 with a clearance existing between the mid-sections 105 and 106 and the outer surface of the elongate member when the first portion 110 is formed into a spring clip as exemplified in FIGS. 7-10. The dotted lines in FIGS. 6A and 6B depict folding locations for producing bends and/or hinges during the spring clip fabrication process.

In some implementations the elongate member 152 comprises one or more materials having sufficient rigidity to resist buckling during use. The one or more materials may comprise any of a variety or composition of materials, such as for example, a metal, an elastomer/plastic, a braided structure, a random stranded structure, combinations thereof, etc. Elongate member 152 may comprise a plurality of portions or sections joined together to form the elongate member.

Elongate member 152 may be fabricated, for example, utilizing a deep-draw fabrication process where a metal is work hardened during the drawing process, thus eliminating the need for secondary heat-treating on the finished part. Elongate member 152 may also comprise, for example, an extruded portion of elastomer/plastic tubing.

According to some implementations, the through passage 153 in a proximal portion of the elongate member 152 adjacent or near the base 118 has a reduced cross-sectional area/diameter that causes the proximal portion of the through passage 153 to engage with the change in profile 132 on the needle shaft 131. In one implementation the reduced diameter portion of the through passage 153 acts as stop, in lieu of aperture 119 in base 118, to limit movement of the needle guard 100 on the needle 130 to the second axial position. In other implementations a reduced diameter bushing or sleeve may be positioned at or coupled with the proximal end 154 of the elongate member 152 to act as a stop.

According to other implementations, the proximal portion of the elongate member 152 comprises a material that is capable of expanding or flexing over the change in profile 132 in a manner depicted in FIG. 9. In one implementation the proximal portion of the elongate member comprises a resilient material that permits it to expand over the change in profile 132 while at the same time exerting a constraining/radial force on the change in profile 132. An advantage of such implementations is that the radial constraining force applied to the change in profile 132 acts to limit lateral movement of the elongate member 152 after the needle guard 100 has been positioned to cover the distal end of the needle. This is particularly advantageous when a full or partial seal between the distal section 107 or arm 101 and the distal end 156 of elongate member 152 is desired. According to other implementations the entirety of elongate member 152 comprises a flexible material that allows the elongate member to expand or flex over change in profile 132 of the needle 130 as the elongate member is slid or moved to the distal end of the needle.

Figure 13:
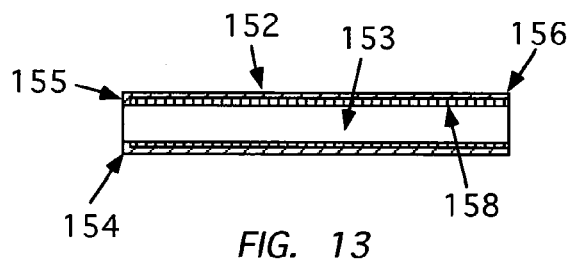

FIG. 13 is a cross sectional side view of an implementation of elongate member 152 having a reduced inner diameter proximal portion 155. The elongate member 152 may also have an absorbent or porous inner coating/membrane/liner or the like 158 sized to contact the outer diameter of needle 130 and absorb or wipe blood or bodily fluids from the exterior surface of the needle as the needle slides or moves through the elongate member. The absorbent or porous member 158 may also absorb blood or bodily fluids that reside in the needle lumen. In some implementations the absorbent or porous member 158 includes a medication, such as, for example, an antimicrobial or antibiotic agent.

Figure 14:
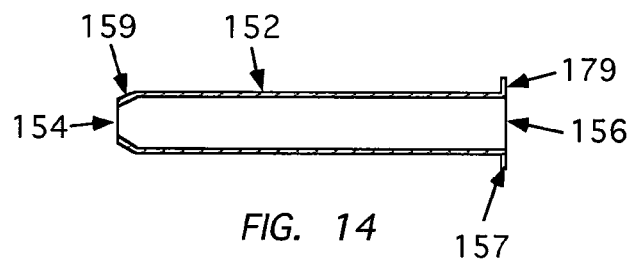

FIG. 14 is a cross sectional side view of an implementation of elongate member 152 comprising a reduced diameter or frustoconical portion 159 at its proximal end 154 and a distal flange 157 at its distal end 156. According to one implementation the distal flange 157 provides a larger contacting surface 179 to facilitate the formation of a seal between the distal section 107 of arm 101 and the distal end 156 of the elongate member when the needle guard is positioned in the second axial position on the needle 130. In other implementations the distal flange 157 and the lip 111 of arm 101 are constructed so that upon the needle guard 100 assuming the second axial position on the needle 130 the lip 111 engages with the flange 157 to help secure the distal section 107 of arm 101 to the distal end 156 of elongate member 152. In such implementations, the distal flange 157 may be annular, continuous or segmented.

Figure 15:
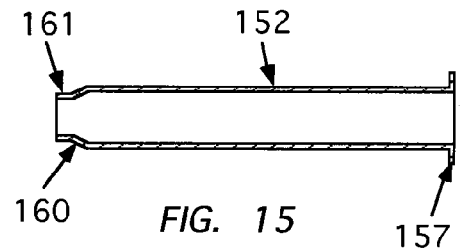

FIG. 15 is a cross sectional view of an implementation of elongate member 152 comprising a proximal section having a reduced diameter or frustoconical portion 160 transitioning to a reduced diameter end section or sleeve 161. The elongate member 152 may also comprise a distal flange 157. In one implementation the proximal end section 161 is used for attaching the proximal end of the elongate member 152 to the base 118. Attachment may be accomplished via stamping, pressing or other mechanical fastening processes. For example, the proximal section 161 may be segmented to form tabs, or the like) that are fixed into aperture 119 or other openings provided in the base 118. In other implementations the shape and size of the proximal section 161 permits it to be press fitted into aperture 119. It is important to note that any of a variety of other attachment methods, or combination of methods, may be used to attach the elongate members 152 disclosed and contemplated herein to the base 118 of the needle guard. These methods may include the use of adhesives, soldering, welding, mechanical attachment, etc. As will be discussed in more detail below, in some implementations the elongate member 152 is unitarily formed with the first portion 110 of the needle guard 100.

An advantage of providing areas/sections of reduced diameter along a length of the elongate member 152 is that these areas/sections assist in maintaining the elongate member coaxially disposed on the needle 130 which reduces friction or drag forces that may otherwise exist as the elongate member 152 is moved along the needle shaft 131. They also assist in urging or maintaining the elongate member 152 in a coaxial relationship with the needle shaft 131.

Figure 16:
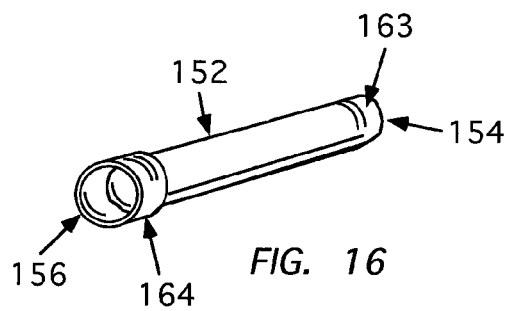
Figure 17:

FIG. 16 is an isometric view of an implementation of an elongate member 152 having an enlarged diameter distal portion 164 and a small diameter proximal portion 163. FIG. 17 is a cross sectional view of one implementation of an elongate member according to FIG. 16 comprising an inner ring or bushing 165 retained within the cavity of the enlarged diameter portion 164 that is situated to concentrically locate the needle 130 within the elongate member 152 and to wipe blood or bodily fluids from the exterior surface of the needle 130 as the needle slides or axially moves through the elongate member 152. One advantage of the enlarged diameter distal portion 164 is that it provides a reservoir for collecting blood or bodily fluids wiped from the exterior surface of the needle and/or that emanate from the lumen of the needle. In one implementation the reservoir contains a coating or material for absorbing the blood or bodily fluids. In one implementation the absorbent material occupies all or a substantial portion of the reservoir and is deformable or pierceable to accommodate an introduction of the distal end of the needle into the reservoir region of the elongate member. In implementations where a seal is provided between the distal end of the elongate member and the distal arm section 107, one or more apertures may be provided in the wall of the reservoir to inhibit the formation of a hydraulic lock. In one implementation the one or more apertures in the wall of the reservoir are sufficiently small to prevent or inhibit blood or bodily floods from passing there through.

In some implementations an internal or external sealing member is provided at or near the proximal end 154 of the elongate member.

In other implementations the elongate member 152 comprises one or more encapsulated annular rings, ribs or segments that deform or flex over the change in profile 132 as the needle guard 100 is advanced over the needle 130. In some implementations the elongate member 152 comprises elongate encapsulated portions that extend along all or a portion of the length of the elongate member. In such implementations the encapsulation structures may be formed by use of an extrusion process. The encapsulated members may comprise chemical substances that are caused to interact with one another as the one or more encapsulated members expand over the change in profile 132 and to solidify to lock the proximal end 154 of the elongate member 152 onto the change in profile 132 of the needle 130.

As discussed above, it may be desirable to form a partial or full seal at the intersection of the distal section 107 of arm 101 and the distal end 156 of the elongate member 152 when the needle guard 100 is positioned in the second axial position. According to some implementations, the inner surface of distal section 107 is coated or laminated with a material, compound or agent conducive to forming a seal with the distal end 156 of the elongate member 152 when the distal section 107 comes into contact with distal end 156. Conversely, or in conjunction with coating or laminating the inner surface of distal arm section 107, the distal end 156 of elongate member 152 may also be coated or laminated with a material, compound or agent conducive to forming a seal. For example, in some implementations one or both of distal section 107 and distal end 156 comprise a formable material, such as an elastomer, for effectuating a full or partial seal between the members. Other examples include coating, laminating, or otherwise treating one or both of the contact surfaces with a tacky substance or adhesive. Other examples may include the fixation of an elastomer O-ring on the distal end 156 of the elongate member 152 so that at least a portion of the O-ring extends distal to the end 156 so that it may mate with a contact surface of distal arm section 107. Other sealing methods are also contemplated.

Figure 18:
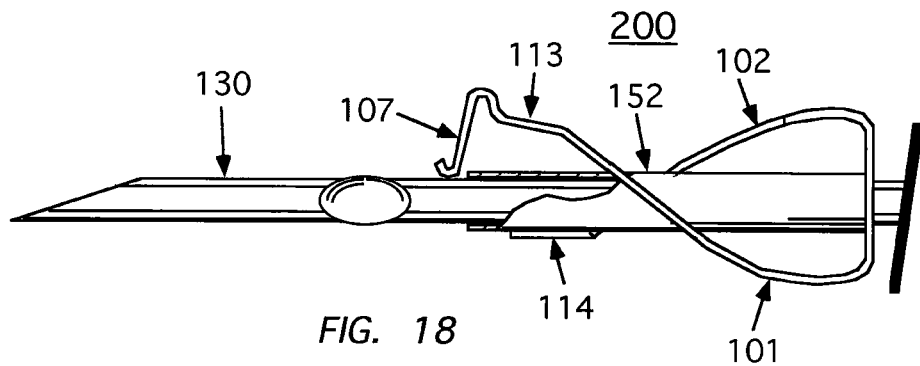
FIGS. 18 and 19 illustrate a needle guard assembly according to another implementation.
Figure 19:
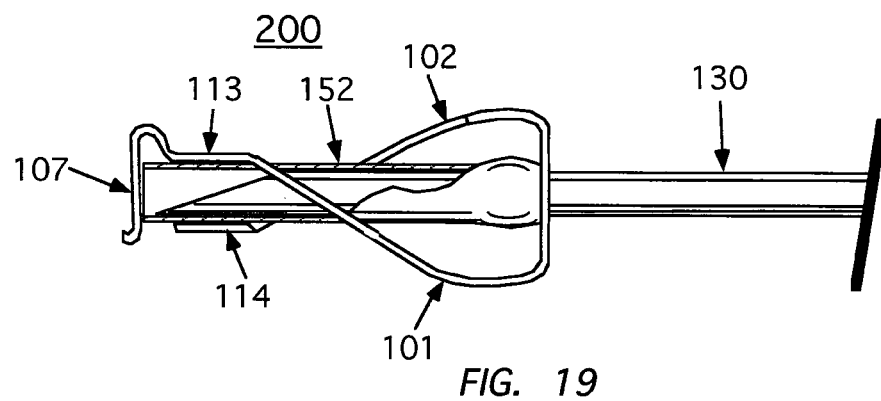

FIGS. 18 and 19 show a needle guard 200 according to another implementation. The needle guard 200 is similar to that of needle guard 100 described above except that arm 102 terminates at segment 114 where it is attached to the outer surface of the elongate member 152. In one implementation, segment 114 is curved to produce an attachment surface that is the same as or approximates the curvature of the outer surface of the elongate member 152. In substantially all other respects the implementations of the first portion 110 and the second portion 150 of the needle guard 200 function in the same way to effectuate a covering of the distal end of the needle 130 as described above. It is important to note that arm 102 may be fixed to the outer surface of the elongate member 152 at more proximally located sites. For example, arm 102 may comprise a shorter length with an end portion of the arm 102 being attached anywhere along the length of the elongate member 152. In other implementations arm 102 is eliminated altogether with the distal end 154 of the elongate member 152 being firmly coupled to the base 118.

According to other implementations the first portion 110 and the elongate member 152 of the needle guard 100 are unitarily constructed. In one implementation this accomplished by subjecting the base 118 of the needle guard to a deep drawing process to form the elongate member 152. In this manner, the elongate member 152 may be described as being co-extensive to the aperture 119 in the base 118. According to one implementation the unitary construction process begins with the formation of a metal strip 50 as shown in FIG. 6C having an area 52 designated to form the base 118 of the needle guard 100. In some implementations the metal strip 50 has a uniform thickness, while in others the strip 50 is provided with an enhanced thickness dimension at least in the region 54 where the deep drawing process is to be applied to form the elongate member 152. In some implementation the arm sections 101 and/or 102, as shown, for example in FIG. 6A, are formed prior to deep drawing the elongate member 152, while in other implementations the arm sections 101 and/or 102 are formed after the formation of the elongate member 152. In some implementations the fabrication process begins with a metal sheet having a uniformed and enhanced thickness dimension which is followed by a process that results in the flattening of the metal sheet in the areas 56 and 58 where the arms 101 and/or 102 are designated to reside. The flattening process may occur before or after the formation of the elongate member 152 by use of the deep drawing process. In conjunction with or after the flattening process to produce one or more areas of a reduced thickness, at least a portion of the reduced thickness areas are cut to produce at least a portion of arms 101 and/or 102.

With reference to FIGS. 13 through 17, one or more of the features 155, 159, 160, 161, 163 and 164 may be formed into the elongate member 152 during the deep drawing process by the use of one or multiple dies dimensioned and shaped to form the one or more features. For example, in one implementation the frustoconical portion 160 and reduced diameter end section 161 of the elongate member 152 is formed during the drawing process. An advantage of incorporating one or both of the features 160 and 161 into the elongate member 152 is that they cause the proximal section of elongate member 152 to be self-centered onto the needle 130 during the assembly process.

According to another manufacturing process, a plurality of elongate members 152 are initially deep drawn, or at least partially deep drawn, from a single metal sheet prior to the metal sheet being segmented for the purpose of forming the first portions 110 of the needle guard 100.

FIGS. 20 through 23 illustrate a needle guard assembly 300 according to another implementation. The needle guard 300 is similar to that of needle guard 100 described above except that arm segments 113 and 114 have been modified to include arcuate recesses 313 and 314 that are configured to at least partially coincide with the curvature of the outer surface of elongate member 152. In one implementation one or both of the recesses 313 and 314 are configured as half-circles that are shaped to coincide with the outer profile of the elongate member 152 when the needle guard 300 is in the second axial position to protect the distal end of needle 130. The circumferential edges of recesses 313 and 314 rest against the outer surface of the elongate member 152 when the needle guard 300 is in the second axial position (FIG. 23) to inhibit the distal sections 107 and 108 of arms 101 and 102 from being urged outward away from covering the distal end of the needle 130 in the event an improper force is applied to one or both of the arms.

Figure 20:
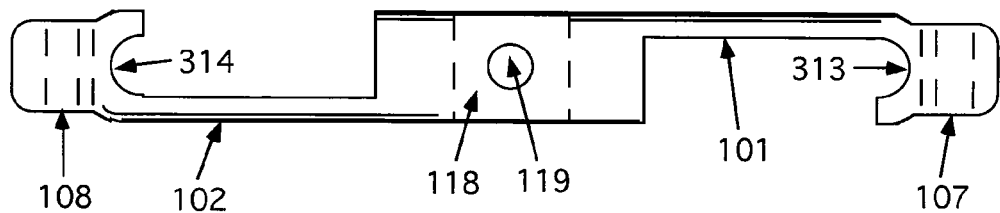
FIGS. 20 through 23 illustrate a needle guard assembly according to another implementation.
Figure 21:
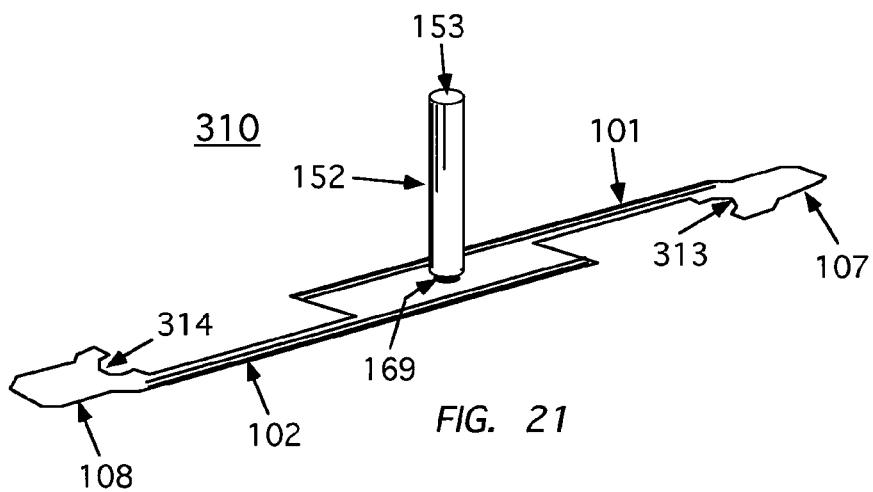
Figure 22:
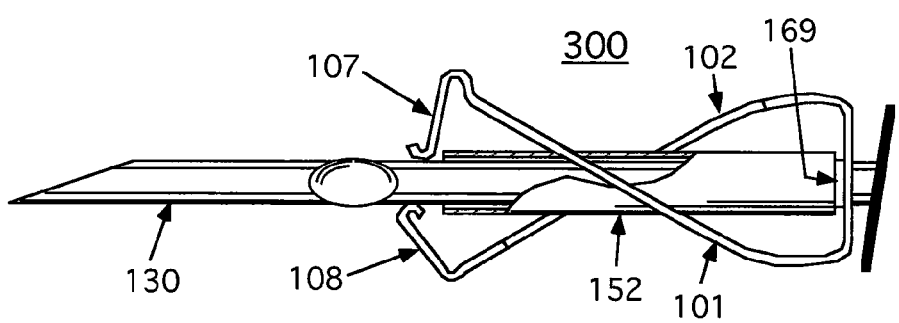
Figure 23:
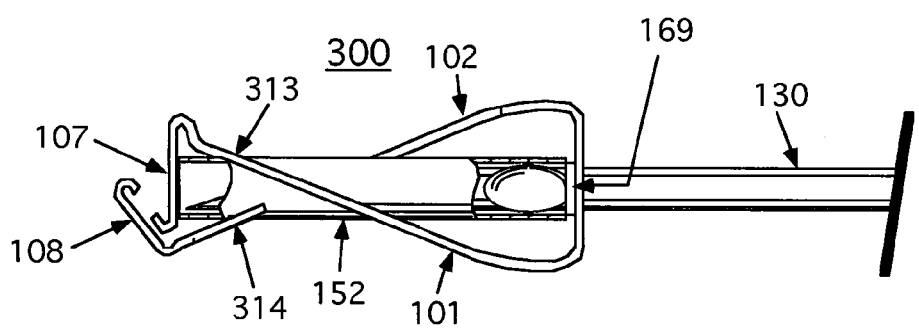

As shown in FIG. 21, a method of fabricating a needle guard according to the implementations disclosed and contemplated herein is to first stamp, cut or otherwise form the first portion 310 of the needle guard from a flat piece of resilient material as exemplified in FIG. 20. After the first portion 310 is formed the elongate member 152 may be positioned so that the through passage 153 is axially aligned with the aperture 119 in base 118. A fixture extending through the aperture 119 and through at least a portion of the through passage 153 may be used to support the elongate member 152. According to other methods, the proximal end 154 of the elongate member 152 is provided with an outer reduced diameter segment 169 that extends through or is otherwise fitted to aperture 119 to fully or partially support the elongate member 152 in a perpendicular relationship with the first portion 310 as shown in FIG. 21. In one implementation, a reduced diameter annular ring located near the proximal end 154 of the elongate member 152 provides a means to snap fit the proximal end of the elongate member into the base aperture 119 to secure the elongate member 152 to the base 118. In other implementations, a slit or slot is provided in the base 118 that extends from a side edge of the base to the aperture 119. In this manner the elongate member 152 may be provided with a reduced diameter annular ring portion near its proximal end 154 that permits the elongate member to be side loaded and fixed within the aperture 119 to effectuate an attachment of the elongate member 152 to the base 118. Upon the elongate member 152 being properly supported on or attached to the first portion 310, the first portion may be bent or partially bent to produce or partially produce the requisite arm portions and hinges. At this stage the first portion 310 and elongate member 152 may be loaded onto the needle 130 with the first portion 310 being further bent (if required) and arranged on the needle 130 in a manner depicted in FIG. 22.

According to some implementations the first portion 310 and elongate member 152 of needle guard 300 are unitarily constructed.

Figure 24:
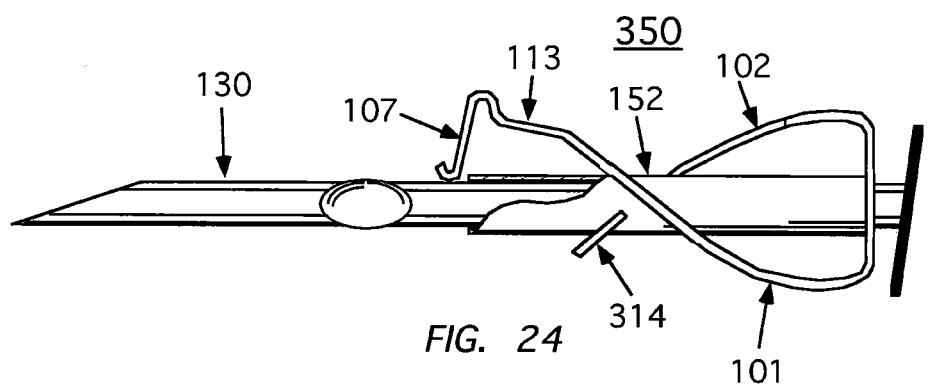
FIG. 24 illustrates a needle guard assembly according to another implementation.

FIG. 24 shows a needle guard 350 according to another implementation. The needle guard 350 is similar to that of needle guard 300 described above except that arm 102 terminates just distal to recess 314 along dotted line 320. In such an implementation the recess portion 314 is continually urged into contact with the outer surface of the elongate member 152 with the distal section 107 of arm 101 situated to singularly cover the distal end 156 of the elongate member when the needle guard 350 is situated in the second axial position on the needle 130. The arms 101 and 102 of needle guards disclosed and contemplated herein may comprise different types of features as exemplified in FIG. 24 where arm 102 is comprises a recess 314 for abutting the outer surface of elongate member 152 and where arm 101 comprises an elongate surface 113 for abutting the outer surface of the elongate member 152.

According to some implementations the first portion and elongate member of the needle guard of FIG. 24 is unitarily constructed.

Figure 25A:
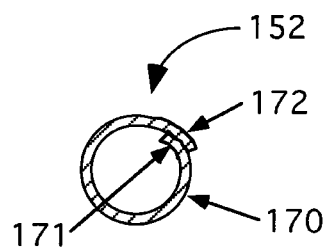
FIGS. 25A-D illustrate needle guard elongate members according various implementations.

According to some implementations, as shown in FIG. 25A, the elongate member 152 comprises a resilient structure 170 having over-lapping longitudinal portions 171 and 172 that are separable to form a temporary longitudinal slit or slot along the length of the elongate member to permit it to be side-loaded onto the needle 130. FIG. 25A represents a top view of the elongate member 152. Upon the elongate member 152 being side-loaded onto the needle shaft, the resilient structure 170 resumes, or substantially resumes, its initial configuration to completely surround the circumference of the needle shaft 131. In one implementation the resilient structure 170 comprises an elastomer material having surface characteristics that facilitate the formation of a seal along the over-lapping longitudinal portions 171 and 172 when their contact surfaces are brought into contact with one another. In other implementations the resilient structure 170 comprises a metal. In some implementations one or both of the over-lapping contact surfaces of portions 171 and 172 is treated or otherwise coated with a substance to induce the formation of a seal along the length of the elongate member 152. In other implementations a seal is formed between the overlapping portions 171 and 172 by use of a sonic welding process or the like.

Figure 25B:
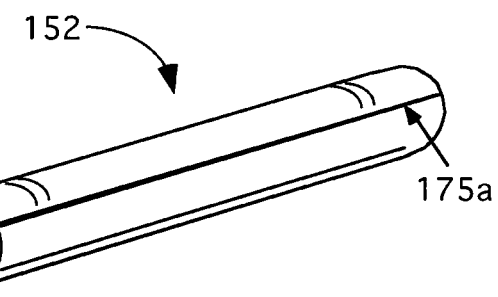
Figure 25C:
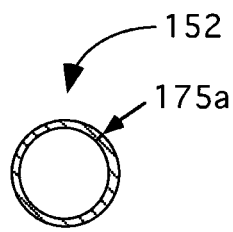
Figure 25D:
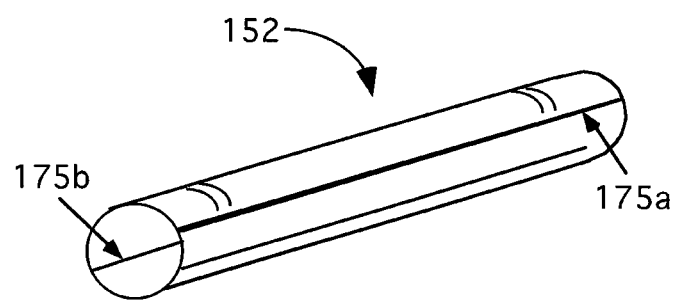
Figure 26:
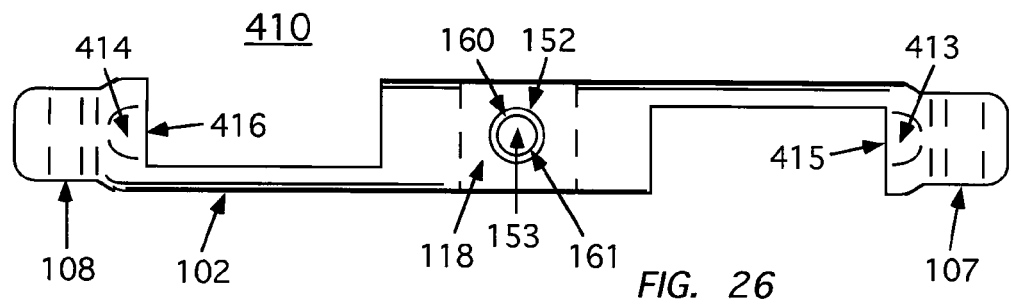
FIGS. 26 through 31 illustrate a needle guard assembly according to another implementation.
Figure 27:
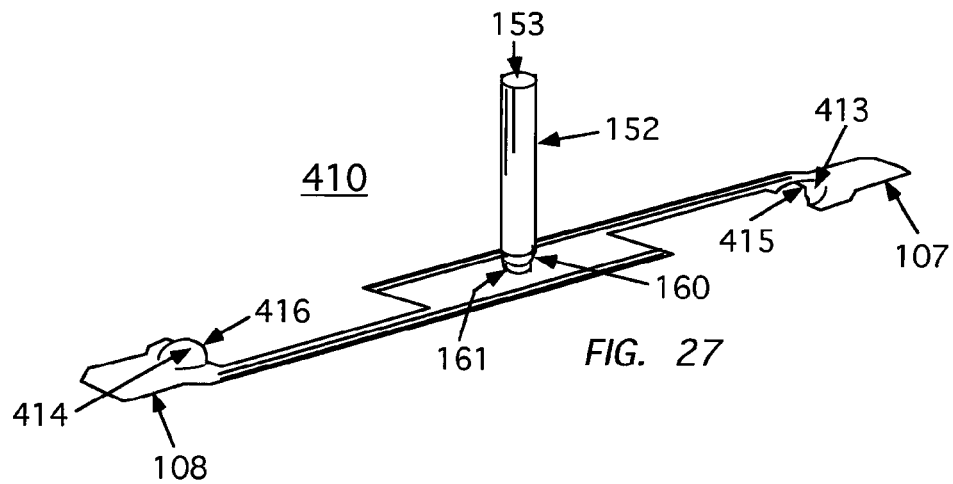
Figure 28:
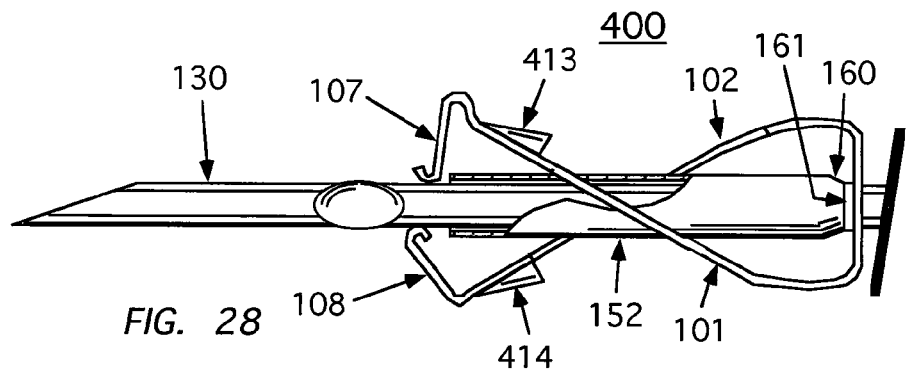

In other implementations, as illustrated in FIGS. 25B-D, the elongate member 152 comprises one or more slits 175*a*, 175*b* that are separable to facilitate a side loading of the elongate member onto the shaft of a needle. As with some of the implementations of FIG. 25A, the elongate member 152 may comprise an elastomer material having characteristics that facilitate the formation of a seal between the mating surfaces of the slits when their contact surfaces are brought into contact with one another. In other implementations one or both of the contact surfaces of slits is treated or otherwise coated with a substance to induce the formation of a seal along the length of the elongate member 152. In other implementations a seal is formed between mating surfaces of the slits by use of a sonic welding process or the like.

Figure 29:
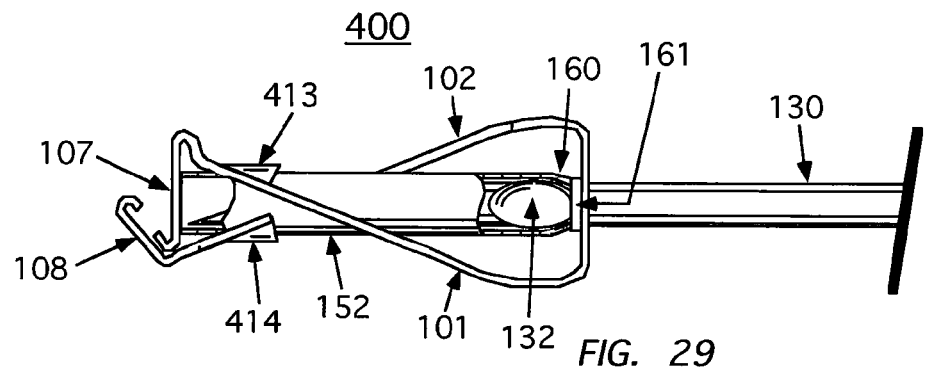
Figure 30:
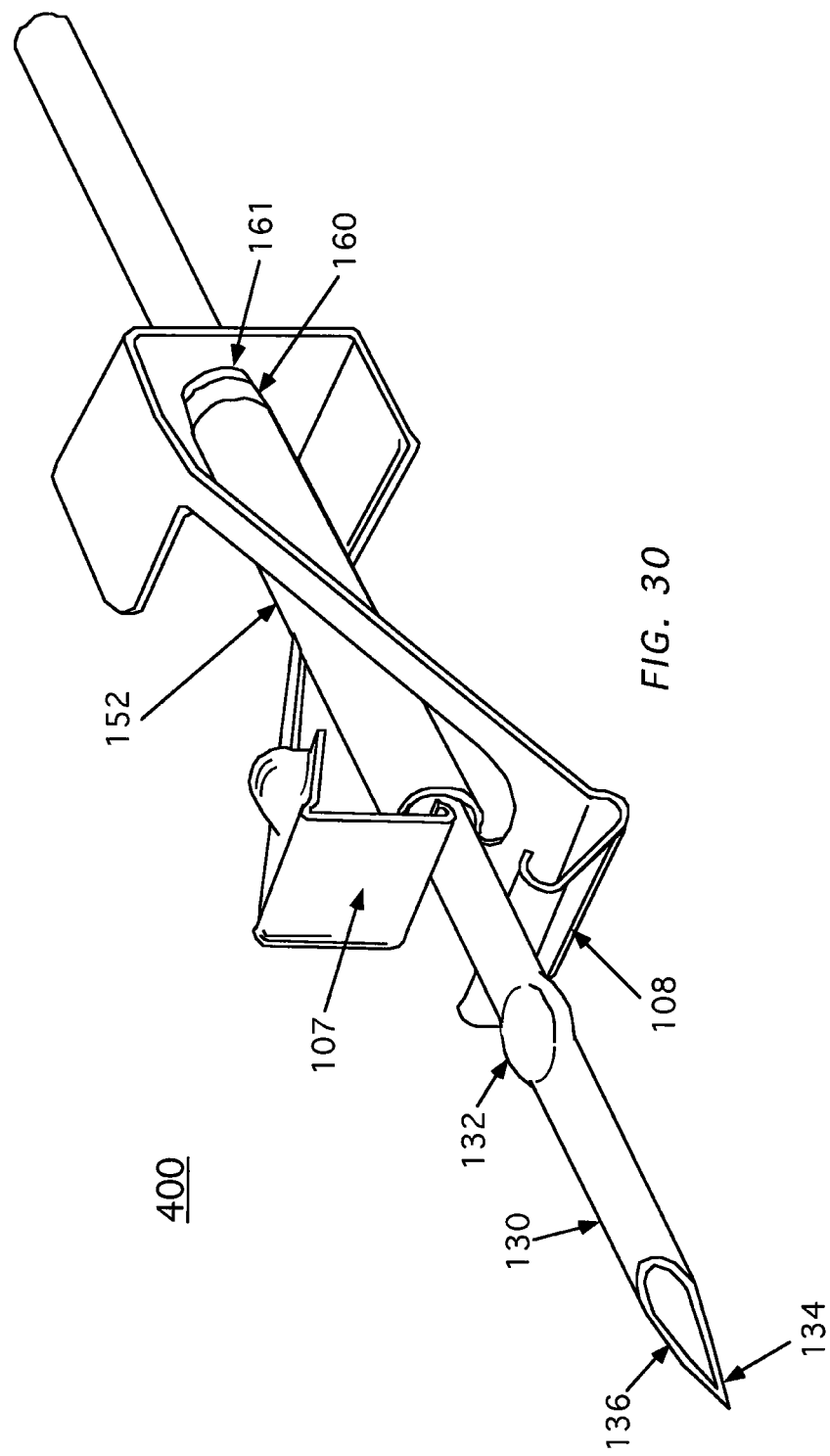
Figure 31:
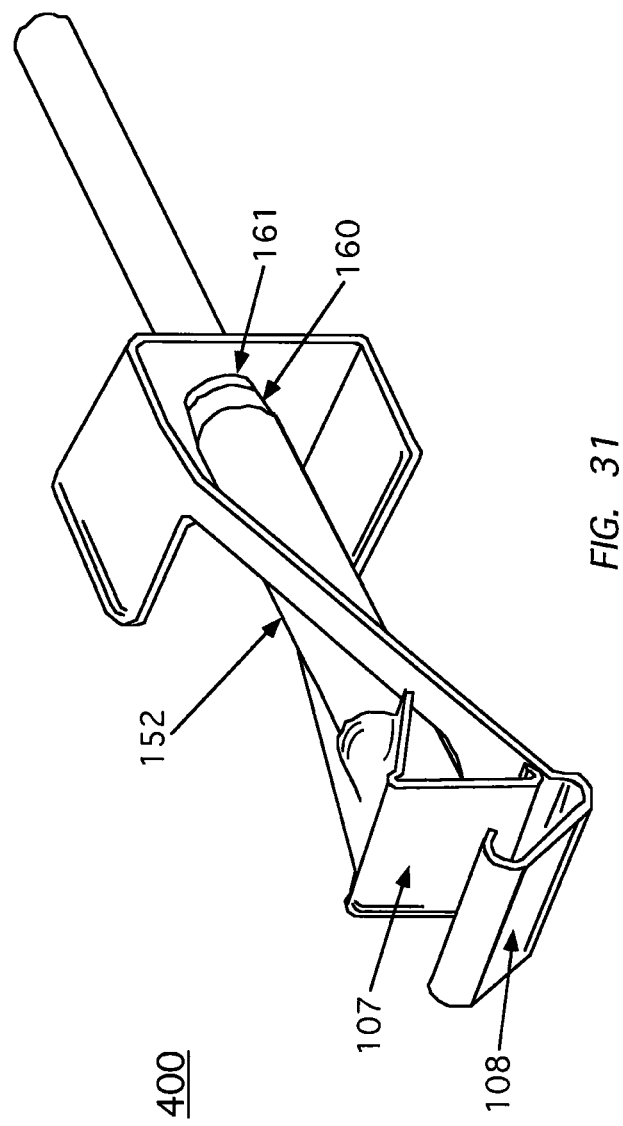

FIGS. 26 through 31 illustrate a needle guard assembly 400 according to another implementation. The needle guard 400 is similar to that of needle guard 100 described above except that arm segments 113 and 114 have been modified to include formed portions 413 and 414 that are configured to at least partially coincide with the curvature of the outer surface of elongate member 152. A proximal section of the elongate member 152 also includes a frustoconical portion 160 and a reduced diameter portion 161 like that depicted in FIG. 15. In one implementation one or both of the proximal edges 415, 416 of formed portions 413, 414 are shaped to coincide with the outer profile of the elongate member 152 when the needle guard 400 is in the second axial position to protect the distal end of needle 130. In practice the inner surfaces of the formed portions 413 and 414 rest against the outer surface of the elongate member 152 when the needle guard 400 is in the second axial position to inhibit the distal sections 107 and 108 of arms 101 and 102 from being urged outward away from covering the distal end of the needle 130 in the event an improper force is applied to one or both of the arms 101, 102 as illustrated in FIG. 29. FIG. 30 is an isometric view of the needle guard assembly 400 situated on the needle 130 in the first axial position. FIG. 31 is an isometric view of the needle guard assembly 400 situated on the needle 130 in the second axial position.

According to some implementations, the first portion 410 and elongate member 152 of needle guard 400 are unitarily constructed.

Like the implementation described above in conjunction with FIG. 24, it is appreciated that the needle guard 400 may be modified so that arm 102 terminates at a location just distal to formed portion 414. In such an implementation the formed portion 414 is continually urged into contact with the outer surface of the elongate member 152 with the distal section 107 of arm 101 situated to singularly cover the distal end 156 of the elongate member when the needle guard is situated in the second axial position on the needle 130.

Figure 61:
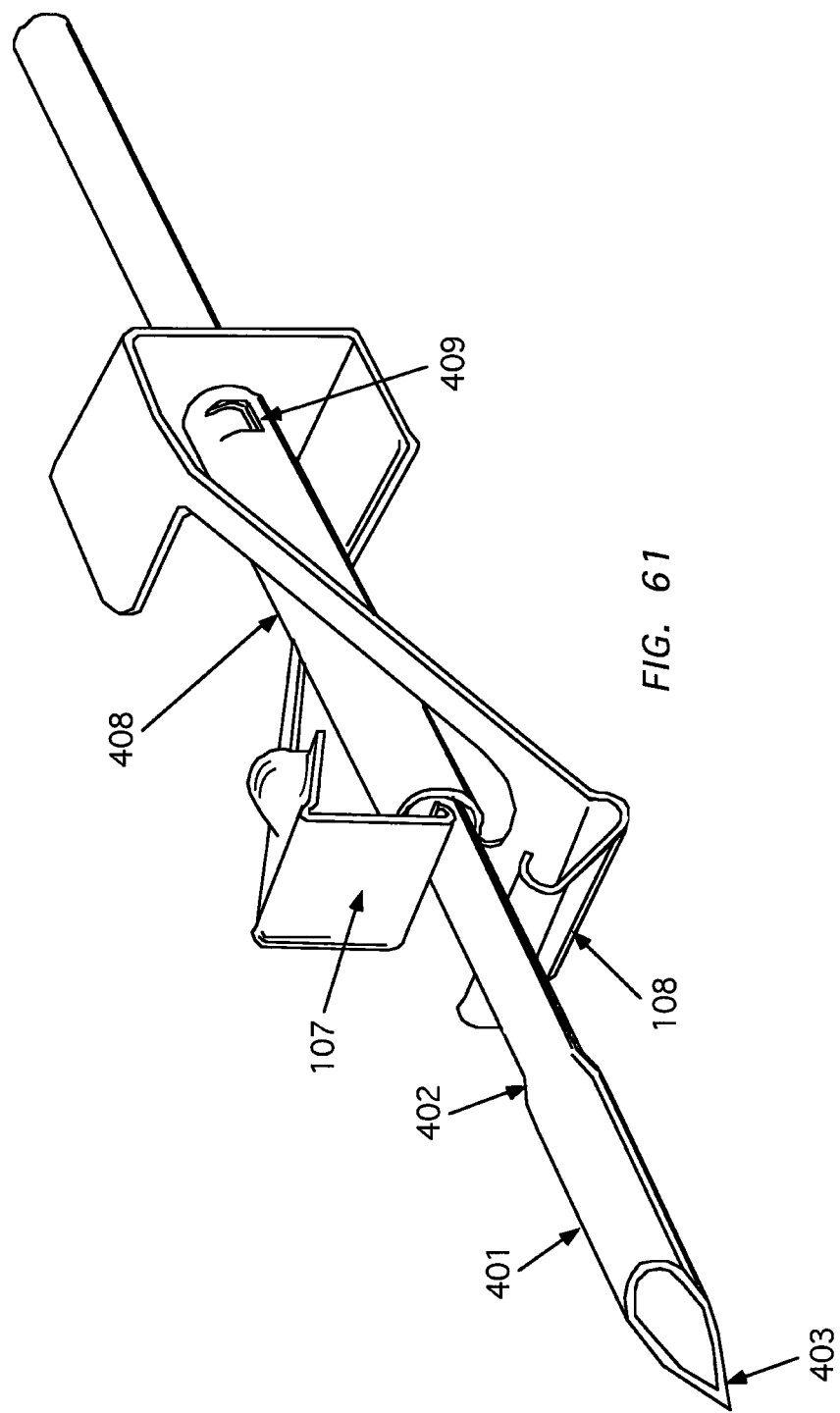
FIG. 61 illustrates a needle guard assembly according to another implementation.

FIG. 61 represents a needle guard assembly similar to that shown in FIG. 30, with there being several distinguishing features. A first distinguishing feature lies in the construction of the needle. In the assembly of FIG. 30 a discrete change in profile 132 is provided as a limiting means at a distal end section of the needle near its distal tip 134, whereas in the assembly of FIG. 61 the limiting means comprises proximal shoulder 402 of a diametrically enlarged elongate section 401 at the distal end of the needle. Another distinguishing feature lies in the construction of the elongate member. In the implementation of FIG. 30, the proximal section of the elongate member 152 includes a reduced diameter portion 161 that is configured to act upon the change in profile 132 on the needle to stop the needle guard on the needle when it has been activated to cover the needle's distal tip 134. In the implementation of FIG. 61 the elongate member 408 comprises a diametrically uniform construction with a tongue 409 cut into a proximal end section of the elongate member. Once formed, the tongue 409 is crimped or bent inward so that at least a portion of the tongue resides within the elongate member 408. The portion of the tongue 409 residing within the elongate member is configured to engage with the shoulder 402 on the needle to stop the needle guard on the needle when it has been activated to cover the needle's distal tip 403. In some implementations two or more tongues are provided.

It is important to note that many of the number of needle guard features disclosed herein (both above and below) are interchangeable among the numerous implementations disclosed and contemplated herein. For example, although some implementations disclose the use of features 113, 114 and other features 313, 314 and others 413, 414, it is appreciated that a combination of these features may be incorporated into a needle guard according to the inventions disclosed herein. Further, as an example, the variety of elongate members 152 and elongate features disclosed herein are interchangeable among the numerous implementations disclosed and contemplated herein.

Figure 32:
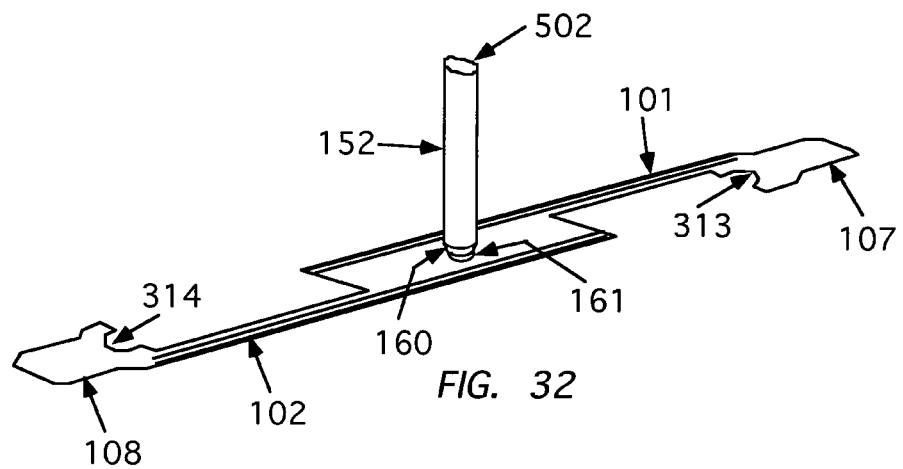
FIGS. 32 through 34 illustrate a needle guard assembly according to another implementation.
Figure 33:
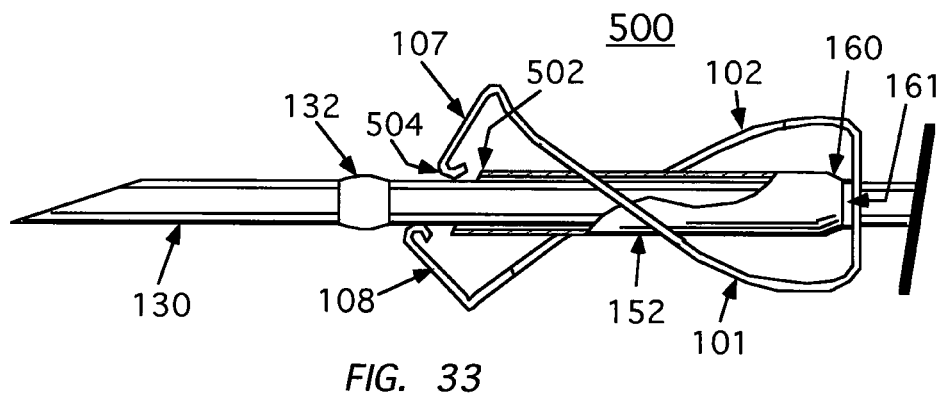
Figure 34:
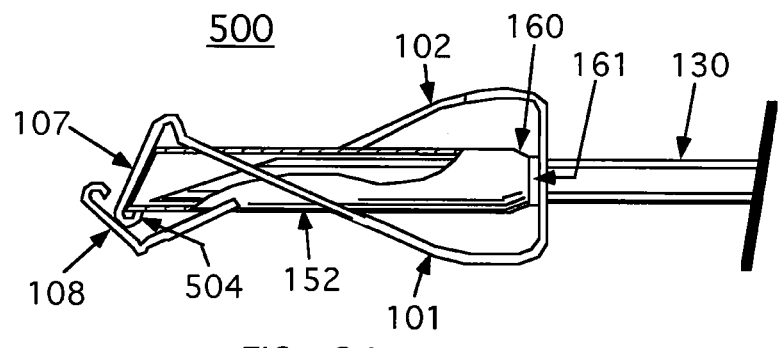

FIGS. 32 through 34 illustrate a needle guard assembly 500 similar to the needle guard assembly 300 described above except that the distal end 502 of the elongate member 152 comprises an oblique orientation with respect to the longitudinal axis of the elongate member and the distal section 107 of arm 101 is angularly oriented to assume the oblique orientation of the distal end 502 of the elongate member when the needle guard assembly 500 is in the second axial position as shown in FIG. 34. A proximal section of the elongate member 152 also includes a frustoconical portion 160 and a reduced diameter portion 161 like that depicted in FIG. 15. Distal section 107 is preferably configured to exert a force on the distal end 502 of the elongate member 152 when the needle guard is in the second axial position. The lip 504 located at the distal end of section 107 is also oriented in a downward facing position and is situated to traverse the beveled distal opening of the elongate member 152 to provide a mechanical stop that inhibits the distal arm section 107 from separating from the distal end 502 of the elongate member when a compressive force or "pinch" is applied to one or both of arms 101 and 102.

According to some implementations the first portion and elongate member 152 of needle guard 500 are unitarily constructed.

A downward facing lip may be provided at the distal end of the distal sections 107 in the various implementations disclosed herein to inhibit the distal arm section 107 from separating from the distal end of the elongate member 152 when a compressive force or "pinch" is applied to one or both of arms 101 and 102. In some implementations the distal end of the elongate member 152 is provided with an indentation or kerf to interlock with a lip provided at a distal end of section 107.

Figure 35:
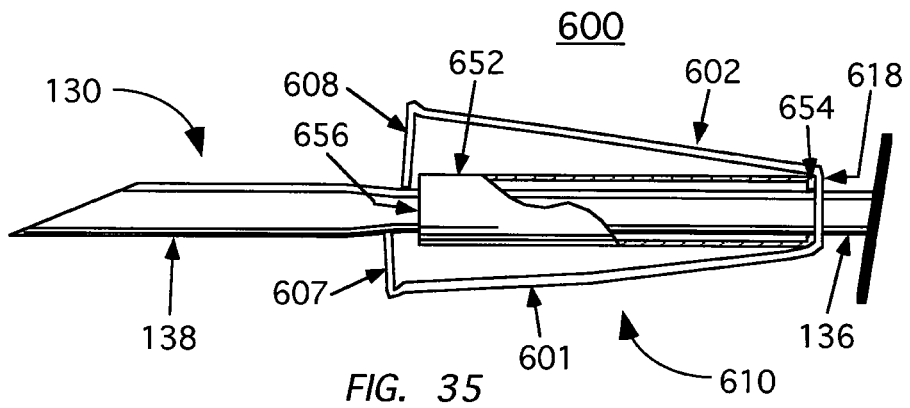
FIGS. 35 through 37 illustrate a needle guard assembly according to another implementation.
Figure 36:
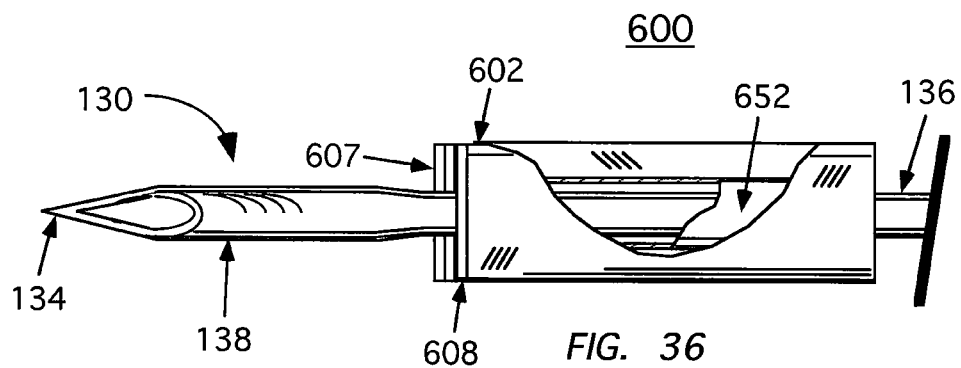
Figure 37:
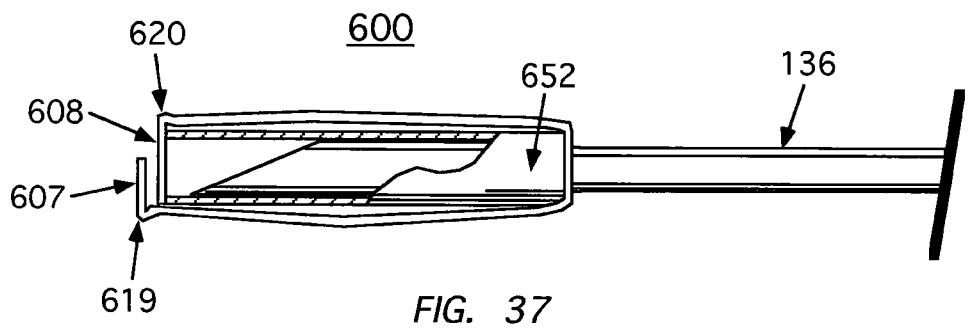

FIGS. 35 through 37 illustrate a needle guard 600 according to another implementation. The needle guard comprises a first portion 610 with an elongate member 652 integrated therein. In one implementation the first portion 610 includes first and second arms 601 and 602, respectively, that extend from opposite sides of a base 618. The first portion is preferably fabricated from a single piece of resilient material that is bent to form the base 618, arms 601, 602 and distal arm sections 607, 608. An aperture in the base 618 (not shown) is sized to receive a proximal portion 136 of the needle 130 and to guide the needle guard along the needle shaft as it transitions from a first axial position (as shown in FIGS. 35 and 36) to a second axial position to protect the distal end 134 of the needle (as shown in FIG. 37). The arms 601, 602 are hinged at the base 618 and are configured to assume an abutting relationship with the outer surface of the needle 130 when the needle guard 600 is situated in a first axial position with the distal end 134 of the needle is unprotected. An elongate member 652 having proximal and distal ends 654 and 656, respectively, is provided with an internal through passage 653 that extends between the two ends. The needle 130 comprises a proximal shaft portion 136 and a flared distal shaft portion 138 of increasing diameter. In use, the elongate member 652 is situated to reside in the first portion 610 between the base 618 and the distal arm section 608. In one implementation the aperture in base 618 is sized to engage with flared distal shaft portion 118 to stop the needle guard 600 in the second axial position as depicted in FIG. 37 with the entirety of the internal passage 653 of the elongate member 652 having a diameter sufficient to be advanced so that the distal end 656 of the elongate member extends to or past the distal tip of the needle. In another implementation the proximal end of the elongate member 652 is provided with a reduced internal diameter portion that acts to stop the needle guard in the second axial position. In another implementation a sleeve or bushing is situated at the proximal end 654 of the elongate member 652 and includes an internal bore with diameter sufficient to act as the second axial position stop.

As illustrated in FIG. 37, substantially coincident with the distal end 656 of the elongate member 652 situated to cover the entirety of the distal end 134 of the needle 130, arms 601 and 602 disengage from the needle shaft and are urged inward by stored energy to cover the distal end of the elongate member. According to one implementation, distal arm section 608 is hinged at location 620 to provide a downward/proximally acting force on the distal end 656 of elongate member 652. In one implementation arms 601 and 602 are provided with protrusions 619 and 620 that function to interact with one or more internal features of a catheter hub to releasably secure the needle guard 600 within the catheter hub in a manner similarly described with respect to FIG. 38.

According to some implementations the first portion and elongate member 652 of needle guard 600 are unitarily constructed.

As discussed above, FIG. 38 is a side view of a safety intravenous catheter assembly 700 in a ready to use operative position according to one implementation. Assembly 700 includes a needle 130 with a sharpened distal tip 134 with an internal lumen extending from a proximal end 140 to the tip 134. A change in profile 132 on the needle shaft functions to stop the needle guard 100 in the second axial position as previously described. A proximal end portion of the needle 130 is attached to a needle hub 704 having proximal protrusions 706 for attaching a male luer fitting. The proximal end 140 of the needle being situated in a flashback chamber 708 of the needle hub 704. As previously discussed, the needle guard 100 is releasably secured in the catheter hub 702 by the engagement of protrusions 117 and 116 with a feature or features 703 situated on the inner wall of the catheter hub. The proximal end of the catheter hub 702 is operatively engaged with the distal end of the needle hub 704. A tubular catheter 710 extends distally from the distal end of the catheter hub 702 in coaxial relationship with needle 130 and terminates proximal to the needle tip 134 so that the needle tip is exposed for puncturing a blood vessel and introducing the catheter 710. In use, upon the catheter 710 being properly introduced into the vessel of a patient, the needle hub 704 is pulled proximally to retract the needle tip 134 from the patient and into the needle tip guard 100. As the needle is withdrawn, the needle guard 100 is secured within the needle hub 702 by the outward force exerted by protrusions 117 and 116. The location of the change in profile 132 on the needle 130 in combination with the dimensional characteristics of the needle guard 100 result in the distal tip 134 being fully housed within the elongate member 152 substantially coincident with the change in profile 132 being stopped on the needle guard. Upon the distal tip 134 entering the distal end 156 of the elongate member 152, the distal arm segments 107 and 108 disengage the needle shaft and are urged inward to cover the distal end 156 of the elongate member by stored energy in the arms 101 and 102. At the same time protrusions 116 and 117 disengage with the catheter hub 702 to permit the needle guard 100 and needle 130 to be fully removed from the catheter hub 702.

Figure 39:
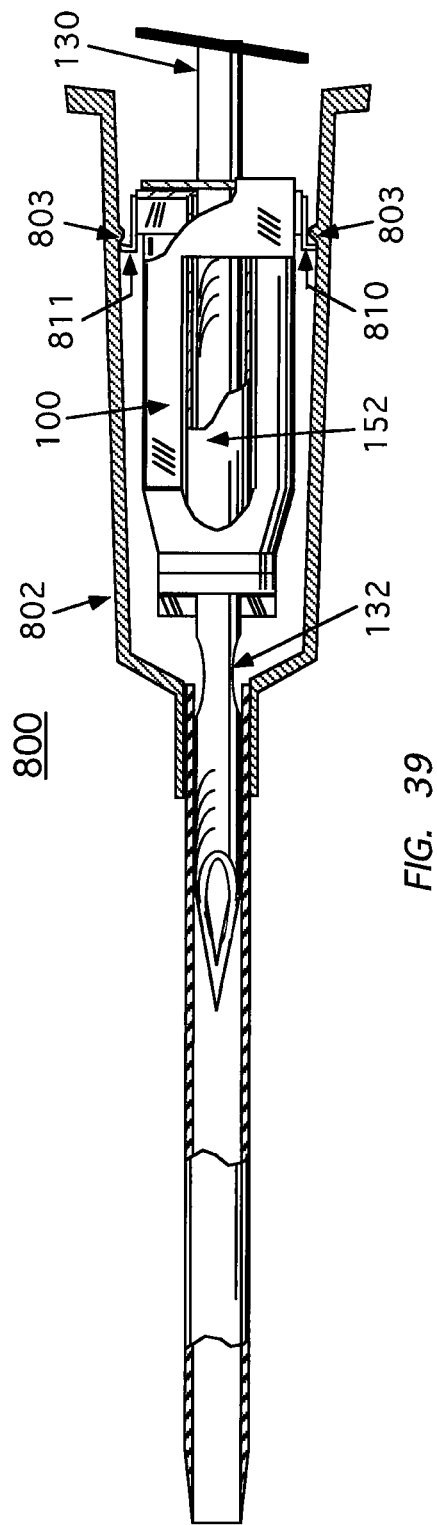
FIGS. 39 and 40 illustrate a safety intravenous catheter assembly according to another implementation.
Figure 40:
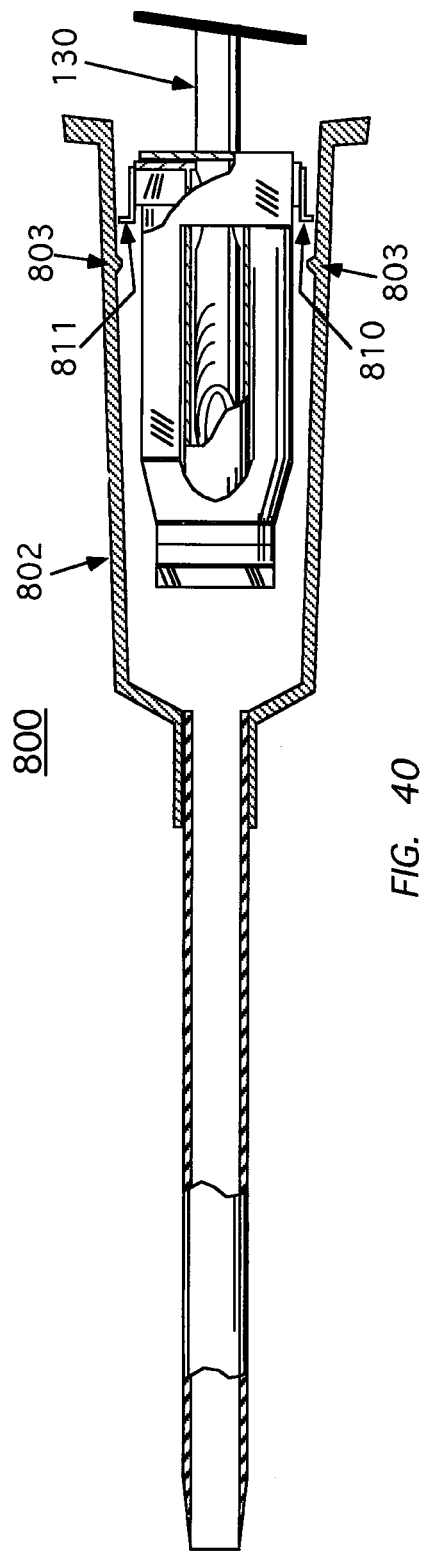
Figure 44A:
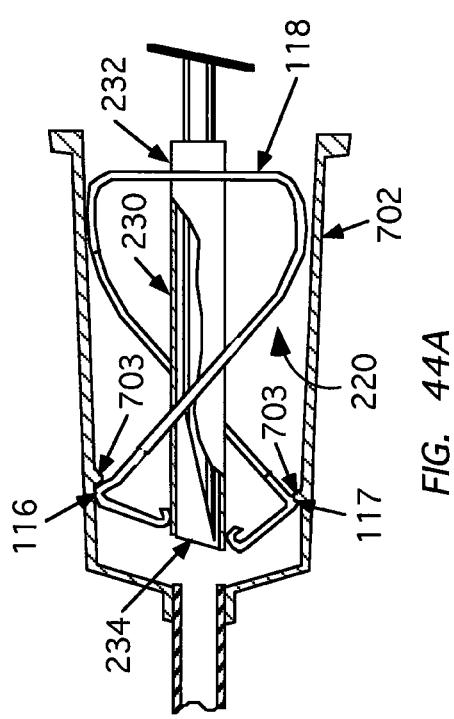
FIGS. 44A-44D illustrate a needle guard according to another implementation in use within an intravenous catheter assembly.
Figure 44B:
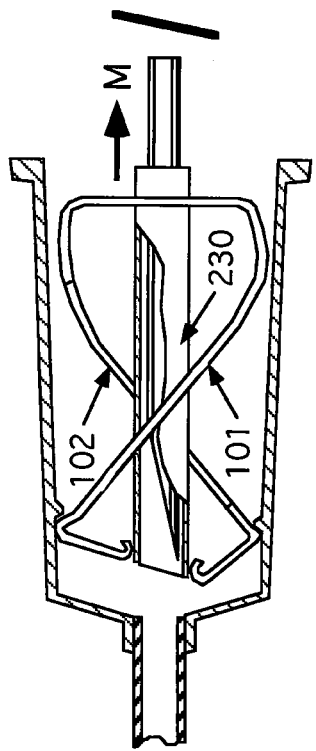
Figure 44C:
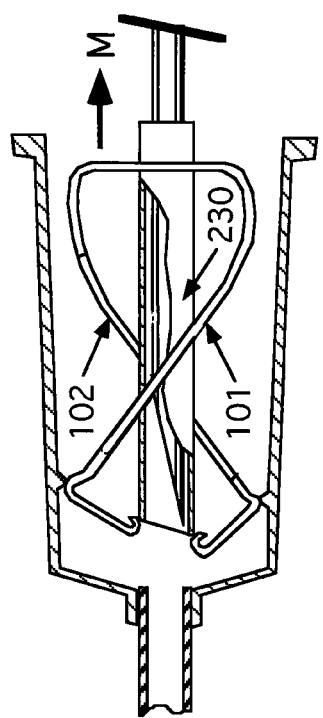
Figure 44D:
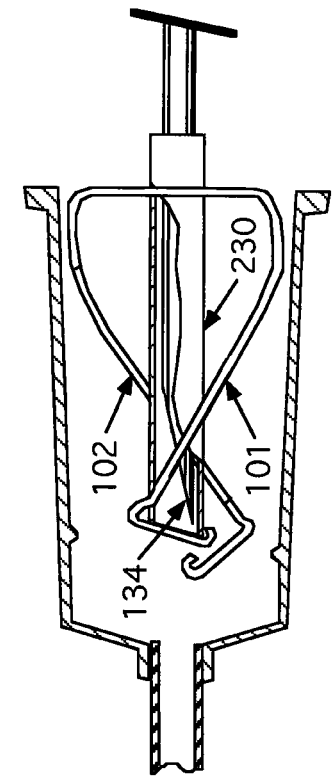
Figure 45B:
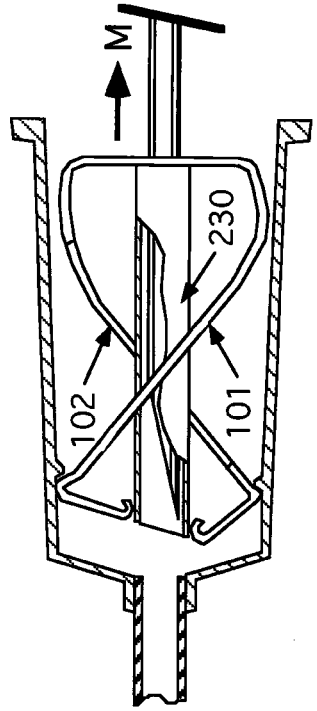
FIGS. 45A-45D illustrate a needle guard according to another implementation in use within an intravenous catheter assembly.
Figure 45D:
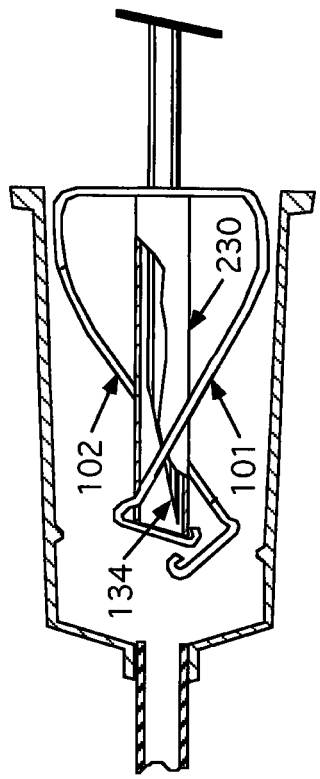
Figure 45A:
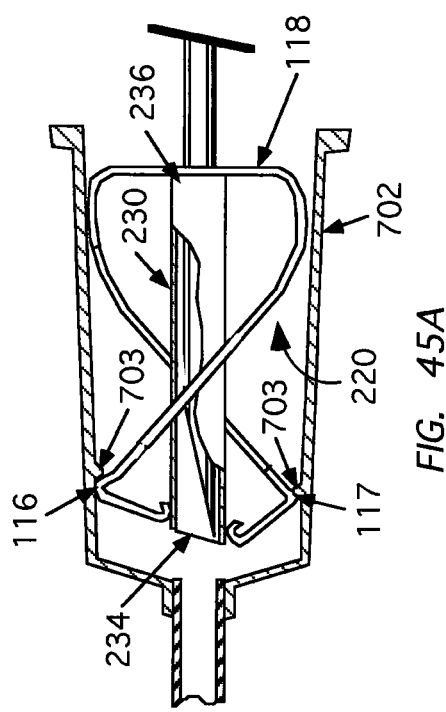
Figure 45C:
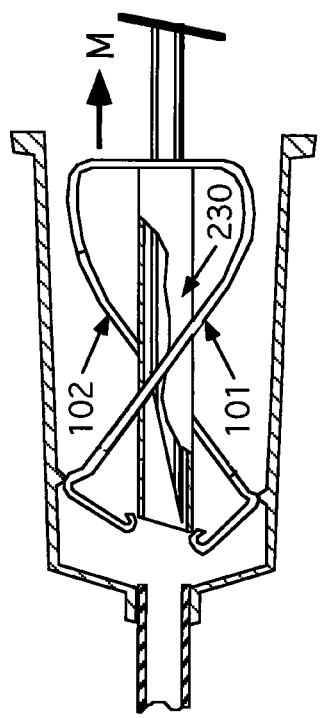

FIGS. 39 and 40 illustrate an intravenous catheter assembly 800 according to another implementation. Assembly 800 is similar to that of assembly 700 discussed above. A difference lies in the manner in which the needle guard 100 is releasably secured within the catheter hub 802. In the assembly 800, in lieu of the use of protrusion 117, 118 formed on arms 101, 102, resilient tabs 810 and 811 situated at or near the base of the needle guard 100 protrude outward to engage one or more features 803 of the inner wall of the catheter hub 802. The outer engaging surfaces of tabs 810 and 811 are preferably arcuate to coincide with the curvature of the inner wall of the catheter hub 802. The one or more features 803 may comprise a recess, undercut, void, groove, protruding feature, etc., configured either annularly or in segments about the inner wall. The resilient tabs 810 and 811 are configured to exert an outward force to cause the engaging surfaces to engage with the one or more features 803 when the assembly 800 is in the ready position or during the withdrawal of the needle 130 into the needle guard 100. The engagement force of tabs 810 and 811 is sufficiently low to permit the tabs to disengage from the one or more features 803 (see FIG. 40) when a proximal force is applied to the needle guard upon the change in profile 132 of the needle engaging needle guard stop.

FIG. 41 illustrates a needle guard assembly 900 situated in a protective position on a Huber needle, the Huber needle being characterized by a change in axis or bend near the distal end of the needle 190. The needle guard assembly 900 is in many respects similar to some of the implementations disclosed and described above except that the internal passage extending through the elongate member 952 is configured in such a way that permits the distal portion 958 of the elongate member to maneuver around the change in axis and to cant as the needle 190 is retracted into a protected position within the elongate member 952. In one implementation a proximal end section 960 of the elongate member 952 is provided with a reduced inner diameter segment of an appropriate length that stops the needle guard on the change in axis. In other implementations, a sleeve of sufficient length with a reduced inner diameter is attached to or otherwise coupled to the proximal end of elongate member 952. In other implementations a change in profile or enlargement is situated proximal to the change in axis to act as the stop.

FIGS. 42A-42D illustrate an intravenous catheter assembly 210 according to other implementations. The intravenous catheter assembly 210 differs from the intravenous catheter assembly 700 of FIG. 38 in that the distal sections 107, 108 of resilient arms 101, 102 are not biased against the needle shaft 131 when the needle guard 100 is in the ready position, but are instead biased against the elongate member 212 as shown in FIG. 42A. As shown in FIG. 42D, in one implementation elongate member 212 comprises a distal section 214 and a reduced diameter proximal section 216. The outer diameter of the proximal section 216 is sufficiently small to reside within the aperture 119 in the base 118 with the outer diameter of at least a portion of the distal section 214 nearest the proximal section 216 having a diameter that is greater than aperture 119. The outer diameter of at least a portion of the proximal section 216 is sufficient to permit the base 118 of the spring clip 220 to slide axially along a length of the proximal section 216 as will be described in more detail below.

As shown in FIGS. 42A and 42B, in the ready position, the base 118 of the spring clip 220 resides on the reduced diameter proximal section 216 of elongate member 212 at a location proximal to the distal section 214, with a distance D1 being provided to permit the base 118 to travel axially along the reduced diameter proximal section 216. In one implementation, when in the ready position, the axial position of the spring clip 220 on the elongate member 212 is releasably fixed by the engagement of the lip segments 111, 112 within one or more recesses 217, 218 located near the distal end of the elongate member 212. In other implementations other co-operable features are provided near the distal end of the elongate member 212 for engaging the lip segments 111 and 112 to assist in delimiting the axial and angular position of the spring clip 220 on the elongate member 212 when in the ready position. In some implementations the recesses 217, 218 impede or limit the spring clip's ability to rotate on the elongate member 212 so as to maintain the distal sections 106, 107 of resilient arms 101, 102 properly oriented with the distal end of the elongate member. In some implementations only a single recess (or other single limiting feature) is provided near the distal end of the elongate member 212 to delimit the spring clip's position on the elongate member.

Figure 52:
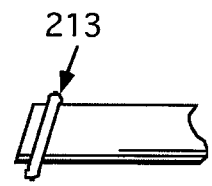
FIG. 52 shows an elongate member according to one implementation.
Figure 53:
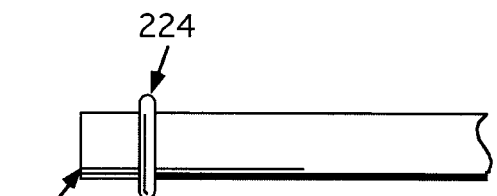
FIG. 53 shows an elongate member according to one implementation.

In some implementation, as shown in FIG. 52, the cooperating feature on the elongate member comprises an annular ring 213 with a proximal shoulder 222 on which the upper portions of the lip segments 111, 112 rest. In one implementation the plane intersected by the annular ring 213 is oblique to the longitudinal axis of the elongate member, as shown in FIG. 52. In other implementations, the elongate member comprises a distal end 223 that is substantially orthogonal to the longitudinal axis of the elongate member. In such an implementation the plane intersected by the annular ring 224 may also be arranged orthogonal to the longitudinal axis of the elongate member as shown in FIG. 53. In each of the implementations of FIGS. 52 and 53, the annular rings may be substituted with discrete first and second raised sections that are angularly and longitudinally situated on the surface of the elongate member to respectively engage lips 111 and 112. In other implementations not shown in the figures, raised features on the surface of the elongate member form pockets for receiving the lip segments 111, 112 to impede axial and rotational movement of the spring clip 220 on the elongate member when the spring clip is in the ready position.

Figure 54:
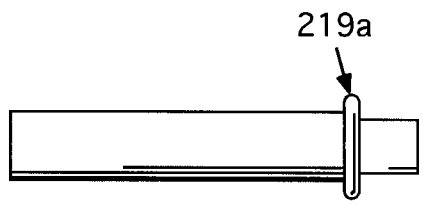
FIG. 54 shows an elongate member according to one implementation.

As previously discussed, the spring clip 220 is releasable secured in the catheter hub 702 by the engagement of protrusions 116 and 117 with a feature or features 703 situated on the inner wall of the catheter hub 702. The proximal end of the catheter hub 702 is operatively engaged with the distal end of the needle hub 704. A tubular catheter 710 extends distally from the distal end of the catheter hub 702 in coaxial relationship with needle 130 and terminates proximal to the needle tip 134 so that the needle tip is exposed for puncturing a blood vessel and introducing the catheter 710. In use, upon the catheter 710 being properly introduced into the vessel of a patient, the needle hub 704 is pulled proximally to retract the needle tip 134 from the patient and into the needle guard. As the needle is withdrawn, the needle guard is secured within the catheter hub 702 by the outward force exerted by protrusions 116 and 117, while at the same time the spring clip 220 is held axially on the elongate member 212 by an inward force exerted by lip segments 111 and 112 within recesses 217 and 218, respectively. When the change in profile 132 of needle 130 is stopped within the elongate member 212, a continued proximal pull on the needle hub 704 causes the base 118 of the spring clip 220 to advance distally on the reduced diameter proximal section 216 of elongate member 212 until the base 118 rests against a shoulder/ledge 219, or the like, located at a proximal end of the distal section 214 of elongate member 212. (In other implementations, as shown in FIG. 54, a stop 219a in the form of an annular ring extends radially from the exterior surface of the distal section 214 of the elongate member 212 to limit the axial advancement of the base 118 of the spring clip 220 on the elongate member 212.) At the same time, the force M applied by the proximal pull is sufficient to cause the lip segments 111 and 112 to slip out of their respective recesses 217 and 218 and advance distally so that the distal arm segments 107 and 108 of spring clip arms 101 and 102 advance over the distal end 221 of the elongate member 212. In one implementation, the full distal advancement of the base 118 on the proximal section 216 of elongate member 212 occurs substantially coincident with the distal tip 134 of the needle 130 entering the distal end 221 of the elongate member 212. At the same time, protrusions 116 and 117 disengage with the catheter hub 702 to permit the needle guard to be fully removed from the catheter hub 702.

FIG. 42C shows the assembly with the distal tip 134 of needle 130 safely secured within the elongate member 212 of the needle guard.

In one implementation, as illustrated in FIGS. 43A-43D, the spring clip 220 is adapted to elongate upon a proximal force M being applied to the needle hub 704 when the change in profile 132 of needle 130 is stopped within the elongate member 212. Initiation of the elongation may occur at a point in time when the base 118 of spring clip 220 engages the shoulder/ledge 219 of the elongate member 212, or before. As shown in FIG. 43B, the elongation occurs as a result of the resistance between the protrusions 116 and 117 of the spring clip 220 with the features or feature 703 situated on the inner wall of the catheter hub 702. The initial elongation is denoted in FIG. 43B by the annotation L1. In the implementation of FIG. 43, when the base of 118 of the spring clip 220 engages shoulder/ledge 219, the axial advancement of the spring clip on the reduced diameter proximal section 216 of the elongate member 212 is insufficient by itself to cause the lip segments 111 and 112 to advance over the distal end 221 of the elongate member. It is instead a combination of the axial advancement of the base 118 on the proximal end of the elongate member 212 and the elongation of the spring clip 220 (denoted by the annotation L2 in FIG. 43C) that cause the lip segments 111, 112 to advance over the distal end 221 of the elongate member. Upon the spring clip 220 being activated to cover the distal end 221 of the elongate member 212, by virtue of the elongation of the spring clip during the activation process, the distal end segment 117 of resilient arm 101 will exert an additional downward force on the distal end 221 of the elongate member as it resiliently attempts to assume a length shorter than L2. Such closure provides enhanced containment of the distal end 134 of needle 130 within elongate member 212.

In another implementation, as shown in FIGS. 44A-44D, the elongate member 230 is provided with no reduced diameter proximal section 216. Instead, in the ready position the base 118 of the spring clip 220 rests against the inside surface of base 118 or is secured at or near the proximal end of the elongate member 230. According to this implementation, the dimensional and material characteristics of the spring clip 220 along with the applied forces between the protrusions 116 and 117 and the wall features 703 of the catheter hub 702 are selected so that an elongation of the spring clip 220 by itself results in an advancement of the lip segments 111, 112 over the distal end 234 of the elongate member 230 to contain the needle tip 134 securely within the elongate member. FIGS. 44A-44D show the base 118 of the needle clip 220 attached to the elongate member 230 with a proximal portion 232 of the elongate member extending through the aperture 119 of the base. FIGS. 45A-45D show an alternative implementation wherein the elongate member 230 (of a shorter length) is positioned entirely distal to the base 118. In such implementations the end 236 of the elongate member 230 may be attached to the base 118 or may simply rest against it.

In implementations where the base 118 of the spring clip 220 moves along a proximal section of the elongate member to effectuate an actuation of the needle guard assembly, such as those described above in conjunction with FIGS. 42 and 43, alternative elongate member constructions are contemplated. For example, in the implementations of FIG. 42 the axial position of the spring clip 220 on the elongate member 212 is held in the ready position by an interaction between lip segments 111, 112 of the spring clip with recesses 217, 218 located near the distal end of the elongate member. In other implementations the spring clip 220 is entirely, or at least partially, held in the ready position by an interaction of the base 118 of the spring clip with a proximal section of the elongate member 212. In implementations where the spring clip 220 is entirely held in the ready position by an interaction of the base 118 with a proximal section of the elongate member, the use of recesses 217, 218, or other retaining features, on the distal section 214 of the elongate member are not necessary.

Figure 46:
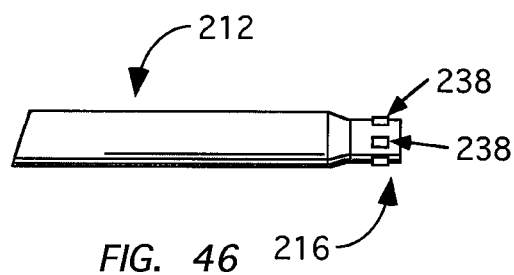
FIG. 46 shows an elongate member according to one implementation.

FIG. 46 illustrates an implementation wherein one or more raised portions 238 are circumferentially disposed about the reduced diameter proximal section 216 of elongate member 212. The one or more raised portions 238 are dimensioned to interact with the aperture 119 in the base 118 of the spring clip 220 to inhibit distal axial advancement of the base 118 on the proximal section 216 until a sufficient force is applied to overcome a resistance between the circumferential region of aperture 119 and the one or more raised portions 238. In some implementation the portion of the base 118 that circumscribes the aperture 119 is deformable upon the application of a force being applied thereto by the one or more raised portions 238 to facilitate an advancement of the aperture 119 over the one or more raised portions 238 when the elongate member is proximally pulled upon. In some implementations the one or more discrete raised portion 238 is substituted with a raised annular ring.

Figure 47:
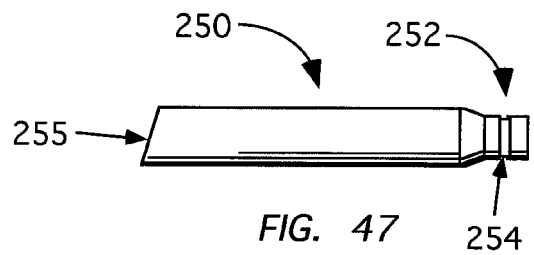
FIG. 47 shows an elongate member according to one implementation.

In other implementations the spring clip 220 is at least partially held on the elongate member in the ready position by use of an annular recess 254 situated on a proximal section of the elongate member. FIG. 47 illustrates an elongate member 250 having a distal section 251 and a reduced diameter proximal section 252. The reduced diameter proximal section 252 has a diameter that is generally greater than the diameter of the aperture 119 in the base 118 of spring clip 220. Situated within the reduced diameter proximal section 252 is an annular recess 254 that is dimensioned to receive a portion of the base 118 of spring clip 220 that circumscribes aperture 119. A portion of the base 118 that fully or partially circumscribes the aperture 119 is sufficiently resilient to permit the diameter of the aperture 119 to expand when the spring clip 220 is initially loaded onto the proximal section 252 of the elongate member 250. The portion of the base 118 that circumscribes the aperture 119 is also sufficiently resilient to permit the diameter of the aperture 119 to expand and to be moved out of the annular recess 254 and to be distally advanced along the reduced diameter proximal section 252 of the elongate member 250 upon a sufficient force being applied to the base 118. An advantage of this construction is that when the spring clip 220 is activated to cover the distal end 255 of the elongate member 250, the compression fit between the base 118 of the spring clip 220 and the proximal section 252 inhibits or minimizes axial and radial movement of the spring clip 220 on the elongate member 250.

Figure 48:
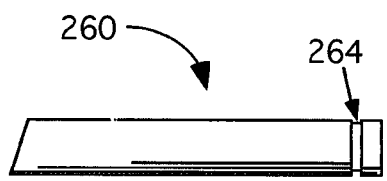
FIG. 48 shows an elongate member according to one implementation.

FIG. 48 illustrates an elongate member 260 similar to the elongate member 250 of FIG. 47 in that it possesses an annular recess 264 for receiving a portion of the base 118 that circumscribes the aperture 119. The difference elongate member 260 and elongate member 250 is that elongate member 260 has a generally uniform cross-sectional along its length.

Figure 49A:
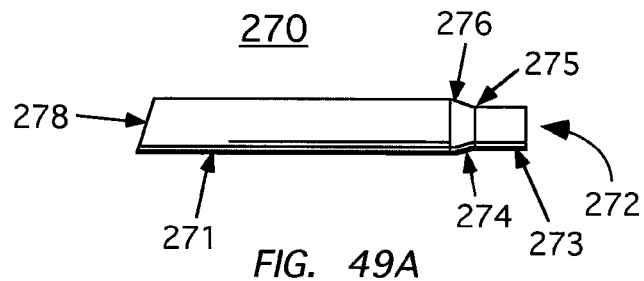
Figure 49B:
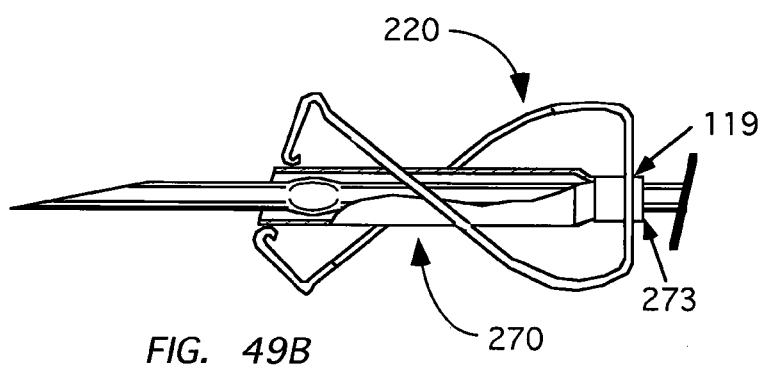

FIG. 49A illustrates an elongate member 270 according to another implementation. The elongate member 270 has a distal section 271 and a proximal section 272. The proximal section 272 comprises a reduced diameter proximal segment 273 and a frustoconical segment 274 whose diameter transitions from the reduced diameter dimension at its proximal end 275 to a larger diameter at its distal end 276. In one implementation the diameter at the distal end 276 is at least equal to the diameter of the distal section 271 of the elongate member 270. As shown in FIG. 49B, in one implementation the spring clip 220 is assembled onto the elongate member 270 so that the reduced diameter proximal segment 273 extends through the aperture 119 in base 118. In some implementations the aperture 119 has a diameter that is just slightly larger than the outer diameter of the proximal segment 273. In other implementations the diameter of the aperture 119 and the outer diameter of the proximal segment 273 are selected to produce a frictional fit between the periphery of the aperture 119 and the outer surface of the proximal segment 273 with the frictional fit permitting a sliding relationship between the two parts. In other implementations the diameter of the aperture 119 prior to the spring clip 220 being assembled with the elongate member 270 has a diameter less than the outer diameter of the proximal segment 273. In a manner similar to that discussed above, in such implementations at least a portion of the base 118 that fully or partially circumscribes that aperture 119 is deformable (plastically and/or elastically) to permit the diameter of the aperture 119 to conform to the outer diameter of the proximal segment 273. The material and dimensional characteristics of the base 118 and the proximal segment 273 permitting a sliding relationship between the two parts upon a minimum axial force being applied thereto.

In one implementation, in the ready position the base 118 of the spring clip 220 resides at the proximal end 275 of frustoconical segment 274, while in other implementations the base 118 resides on the proximal segment 273 as shown in FIG. 49C. In use, upon the catheter 710 being properly introduced into the vessel of a patient, the needle hub 704 is pulled proximally to retract the needle tip 134 from the patient and into the needle guard. As the needle is withdrawn, the needle guard is secured within the catheter hub 702 by the outward force exerted by protrusions 116 and 117, while at the same time the spring clip 220 is held axially on the elongate member 270 by an interaction of the base 118 with the proximal section 272 of the elongate member 270 as described above. When the change in profile 132 of needle 130 is stopped within the elongate member 270, a continued proximal force M applied to the needle hub 704 causes the base 118 of the spring clip 220 to advance distally onto frustoconical segment 274 by virtue of the deformable characteristic of at least a portion of the base 118 as described above. In one implementation distal advancement of the base 118 proceeds until it reaches the distal end 276 of the frustoconical segment 274 or a proximal end of distal section 271. Just prior to, or coincident with the base reaching its distal-most position on the proximal section 272 of the elongate member 270, the distal tip 134 of needle 130 fully enters the elongate member 270 and the lip segments 111 and 112 of the spring clip 220 advance over the distal end 278 of the elongate member as shown in FIG. 49D to safely secure the tip 134 within the elongate member. An advantage of this construction is that when the spring clip 220 is activated to cover the distal end 278 of the elongate member 270, the compression fit between the base 118 of the spring clip 220 and the distal end 276 of the frustoconical segment 274 inhibits or minimizes axial and radial movement of the spring clip 220 on the elongate member 270.

FIG. 50 illustrates an elongate member 280 having a similar construction to that of elongate member 270. A difference is the inclusion of a stop 284 positioned at or near the proximal end of distal section 271. The stop 284 may be in the form of an annular ring as shown in FIG. 50, or may comprise one or more raised segments disposed about the periphery of the elongate member 280. The diameter of the stop 284 is sufficiently large to positively prevent advancement of the spring clip base 118 beyond the stop.

Figure 51:
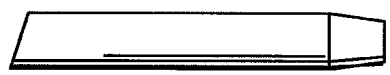
FIG. 51 shows an elongate member according to one implementation.

FIG. 51 illustrates an elongate member 290 similar to elongate member 270 except that the entirety of the proximal distal section 272 comprises a frustoconical configuration.

Figure 55A:
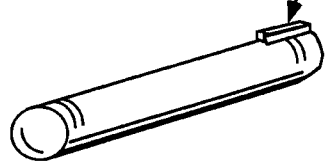
FIG. 55A illustrates an elongate member according to one implementation.
Figure 55B:
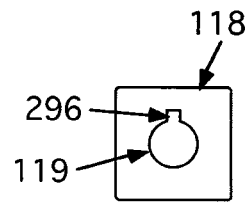
FIG. 55B illustrated a base of a spring clip according to implementation with a key hole provided for receiving the proximal end of the elongate member of FIG. 55A.

According to some implementations the proximal section of the elongate member is equipped with one or more elongate radially extending protrusions 295 as shown in FIG. 55A (only on protrusion shown in FIG. 55A). In such implementations the aperture 119 in the base 118 of spring clip 220 has a corresponding indentation or notch 296 for receiving the one or more radial protrusions 295 as shown in FIG. 55B. A host of configurations are possible. Keying the proximal section of the elongate member to the aperture 119 in the base 118 of the spring clip 220 provides several advantages. First, during operation it inhibits a rotation of the spring clip 220 on the elongate member as it is axially advanced thereon. Second, during the manufacturing/assembly process it makes it easier to properly orient the spring clip on the elongate member. Third, it can prevent an improper pairing of spring clips and elongate members during the assembly process. According to one implementation, length of the one or more radial protrusions 295 is selected so that the spring clip 220 is prevented from rotating on the elongate member at all times. That is, when the needle guard is in the ready state and the activated state. In other implementations the length of the one or more radial protrusions 295 is selected to be shorter so that rotational movement of the spring clip 220 on the elongate member is permitted upon the needle guard achieving the activated state, with rotational movement otherwise inhibited when the needle guard is in the ready state or transitioning from the ready state to the activated state.

FIGS. 56A and 56B illustrate another key form with FIG. 56A depicting an elongate member with a flat side 296 and FIG. 56B depicting the base 118 of the spring clip 220 with an aperture 119 that conforms with the cross-sectional shape of the elongate member.

As discussed above, according to some implementations a deformation of at least a portion of the base 118 of spring clip 220 occurs when acted upon by the distal section of the elongate member to cause a diametric expansion of aperture 119. In other implementations, as shown in FIG. 57A, the base 118 comprises a plurality of deformable projections 298 along the perimeter of opening 119. The material and dimensional characteristics of the projections 298 are selected so that a bending and/or compression of the projections results when a selected portion of the proximal section of the elongate member acts upon them as the elongate member is proximally pulled upon. For example, in the implementation of FIG. 49, the base 118 of FIG. 57A may be used to achieve similar results. As a starting point the projections 298 are dimensioned so that a circle that connects their apices has a diameter that permits the base 118 to slide along the proximal section 272 of the elongate member 270 until the base encounters the proximal end 275 of frustoconical segment 274. Preferably, but not necessarily, three or more projections 298 spaced equidistant about the perimeter of aperture 119 are provided to assist in maintaining an orthogonal relationship between the base 118 and the longitudinal axis of the elongate member 270 during the assembly of the device and also during its use. In other words, axial alignment of the base with respect to the elongate member is better maintained. During activation the proximal force M applied to the needle hub 704 causes the base 118 of the spring clip 220 to be urged distally on the frustoconical segment 274. The force applied causes the deformable projections 298 to deform (i.e., by compression and/or bending) to permit the base 118 to travel along the outer surface of the frustoconical segment 274 until it reaches its distal end 276 where it is stopped. The needle guard assembly otherwise activates in a manner similar to that described above in conjunction with FIGS. 49A-49D.

In other implementations the ability of the aperture 119 to expand, and in some instances to contract, is achieved by the inclusion of one or more slits 299 cut into the base 118 as shown in FIG. 57B. In addition to their suitability for use in the, for example, the implementation of FIGS. 49A-49D, the base 118/aperture 119 constructions of FIGS. 57A and 57B are particularly useful in conjunction with the elongate members depicted in FIGS. 46-48 by virtue of the aperture's 119 ability to adapt to diametric variations either by expansion and/or contraction.

FIGS. 58A-58C illustrate an elongate member 301 according to another implementation. For the sake of simplicity, the figures show the elongate member 301 without the spring clip. FIG. 58A is an isometric view of the elongate member 301 alone. FIG. 58B shows the elongate member 301 mounted on a needle shaft 131 in a ready position. FIG. 58B shows the elongate member 301 on the needle shaft 131 after the needle guard assembly has been activated with the distal tip 134 of the needle 130 residing entirely within the elongate member 301. A distinguishing feature of the elongate member 301 among those previously disclosed herein is the inclusion of a seal member 302 disposed at or near its distal end. The seal member 302 advantageously seals the distal tip 134 of the needle 130 within the elongate member 301 after the distal tip has been fully withdrawn into the elongate member. Such an arrangement facilitates the containment of bodily fluids that may flow from the needle tip 134 after its introduction within the elongate member 301.

The seal member 302 may comprise any of a variety of forms. In one implementation the seal member 302 comprises an elastomeric insert 303 disposed within the distal end of the elongate member as shown in the figures. In some implementations the elastomeric insert 303 has an outer diameter greater than the inner diameter of the distal end of the elongate member 301. In such implementations the elastomeric insert 303 is held within the elongate member 301 by compressive forces exerted by the elastomeric insert against the inner wall of the elongate member. In other implementations adhesive or heat bonding is used in lieu of or in conjunction with the aforementioned attachment method. In other implementations the seal member 302 comprises an elastomeric cap 305 that stretches over and resides on the outside of the elongate member 301 as shown in FIG. 59. In some implementations adhesive or heat bonding is used in lieu of or in conjunction with the aforementioned stretch attachment method.

In the implementations of FIGS. 58 and 59 a slit 304 that diametrically transverses the face of the seal member 302 facilitates a passage of the needle 130 through the seal member. Features other than a self-closing slit are also contemplated. As illustrated in FIGS. 58B and 58C, when the distal tip 134 of needle 130 assumes a position within the elongate member 301 the slit 304 closes. In some implementations the distal end of the elongate member 301 comprises an enlarged distal end section 306 for receiving or otherwise facilitating an attachment of the seal member 302 to the elongate member as shown in FIGS. 58 and 59. In the implementation of FIG. 59 the enlarged distal end section 306 provides a proximal annular shoulder 307 upon which the proximal portion of the elastomeric cap 302 may rest. An enveloping of the elastomeric cap 305 over the distal end section 306 provides enhanced securement of the elastomeric cap on the elongate member.

In the preceding description of FIGS. 42-59 needle guard assemblies comprising a spring clip portion and an elongate member portion have been described within the confines of intravenous catheters. It is appreciated, however, that the needle guard assemblies of FIGS. 42-59 may be integrated with a host of other types of needle products including, but not limited to, syringes, guidewire introducers, blood collection devices, etc. In some instances what will distinguish these other types of needle products from intravenous catheters and each other is the manner in which the needle guard assembly is advanced over the needle shaft. For example, in some instances mechanical propulsion to advance the guard assembly along the needle shaft is provided directly by a user's hand, a spring, pressurized air or other propulsion means. In the preceding description of FIGS. 42-59 the spring clips have been disclosed as comprising first and second resilient arms 101 and 102. It is important to note, however, that any of a variety of clip configurations is possible, such as, for example, single arm clips like those shown in FIGS. 18, 19 and 24. Moreover, as with the implementation of FIGS. 60A and 60B below, the arm of the clip may rely on other means, other than its own resiliency, to close itself over the distal end of the elongate member. It is also important to note that many of the features associated with the spring clips and elongate members disclosed herein (above and below) are interchangeable and/or combinable to formulate a wide variety of needle guard assemblies and safety needle products.

FIGS. 60A-60C illustrate a guidewire introducer 360 according to another implementation. The guidewire introducer 360 comprises a needle 361 whose proximal end is secured within a needle hub 364. The needle comprises a change in profile 362 on its distal end near the needle's distal tip 363. When in a ready position a needle guard assembly resides within a housing 367 that is attached at its proximal end to the needle hub 364. The needle guard assembly comprises a first part 370 and a second part 380. The first part 370 comprises a midsection that only partially circumscribes the shaft of the needle 361. Residing within the midsection is the second part 380 which is in the form of a cylindrical elongate member that fully surrounds the needle shaft. In one implementation, the proximal end of the elongate member 380 includes a raised annular ring 381 that fits within an annular recess 373 in the base of the first part 370 to secure the elongate member 380 to the first part 370. In one implementation the first part 370 comprises a molded plastic structure having an arm 371 that extends distally from a base where it is hinged. The arm 371 has a distal section 372 that is configured to rest against the shaft of the needle 361 when the guard assembly is in a ready position (see FIG. 60A) and to cover the distal end of the elongate member 380 when the guard assembly has been activated (see FIG. 60B). When in the ready position, the guard assembly 370 is held within the housing 367 by retaining means (not shown in the figures) against a force exerted by a coil spring 374, or other resilient structure, that is situated to propel the guard distally when it is released from the retaining means. In the example of FIGS. 60A and 60B, the proximal end of the spring 374 is attached to the base of the housing 367 and at least a portion of its distal end circumvents a portion of the molded plastic structure 370, including at least a portion of the arm 371. In use, when the needle guard is released from the retaining means, the compressed spring 374 expands distally to propel the needle guard forward until the distal tip 363 of the needle 361 resides entirely within the elongate member 380. In addition to propelling the needle guard forward along the needle 361, the spring 374 also compressively acts on the arm 371 to urge the arm 371 radially inward so that the distal section 372 of the arm covers the distal end of the elongate member 380.

In other implementations, the first part 370 and the second part 380 of the needle guard comprise spring clips and elongate members similar to or the same as those disclosed above and below. In such other implementations the spring 374 may be positioned beneath the base 118 of the spring clip so as to be situated to propel the spring clip distally along the needle shaft.

FIGS. 62A-62D illustrate a needle guard assembly similar to, for example, those depicted in FIGS. 6-10, 20-23 and 26-29. FIGS. 62A and 62B are top and side views of the needle guard, respectively, prior to a folding of the resilient arms 422 and 423 to form the spring clip 421. In FIGS. 62A and 62B the elongate member 430 is shown extending upwardly from the base 118. As described above, the elongate member 430 may comprise a part separate to the first part 420 whereby it is attached to the base 118 or simply rides between the base 118 and the distal end of the resilient arms 422, 423. The elongate member 430 may also be formed from the first part 420 by means of a drawing process as previously described. As with the guidewire introducer 360 disclosed above, in some instances it is desirable that the needle guard be propelled distally along the shaft of the needle in order for it to assume its active position. In the implementations depicted in FIGS. 60A-60C a coil spring 374, separate to the clip itself, provides such propulsion. In the needle guard assemblies of FIGS. 62A-62D, a spring means is not formed separately from the clip but is instead formed from the same stock material as the clip itself. That is, it is formed integrally with the clip. As shown in FIGS. 62A and 62B, an elongate protrusion 440 extends from a side of the base 118 and is provided with a plurality of longitudinally aligned elongate apertures 441. Like resilient arms 422 and 423, the protrusion 440 also comprises a resiliency that results in the formation of a spring 442 when the protrusion 440 is folded along lines 443 as shown in FIGS. 62C and 62D. An aperture 446 in a base 445 of the protrusion 440 is aligned with apertures 441 so that when the protrusion is folded the needle guard assembly may be loaded onto the needle shaft. In, for example, a guidewire introducer product like that depicted in FIG. 60, the base 445 of the protrusion 440 may be attached to the base of housing 367. When the needle guard is in the ready position the formed spring 442 assumes a compressed state within the housing 367 and acts upon the base 118 to urge the needle guard comprising spring clip 421 and elongate member 430 distally along the needle shaft toward the distal end of the needle. Upon the needle guard being released from the housing 367, spring 442 pushes the guard distally until the distal tip of the needle resides entirely within the elongate member 430 as shown in FIGS. 62C and 62D.

In other implementations the elongate protrusion 440 simply acts as a tether to limit distal advancement of the needle guard on the needle shaft. While in other implementations the protrusion is used to form the spring 442 and to also act as a limiting means to limit distal advancement of the needle guard on the needle shaft.

FIGS. 63A-63D illustrate a needle guard 510 according to another implementation. The needle guard may be manufactured from a substantially flat material having resilient characteristics and with a construction that resembles or is the same as those shown in FIGS. 6A, 6B, 20, 26 and 32. For descriptive purposes, like parts in FIGS. 63A-62D utilize the same reference numerals as those used in FIG. 6A. It is important to note, however, that the construction is not in any way limited to those illustrated in FIGS. 6A, 6B, 20, 26, 32 and 42.

Figure 63A:
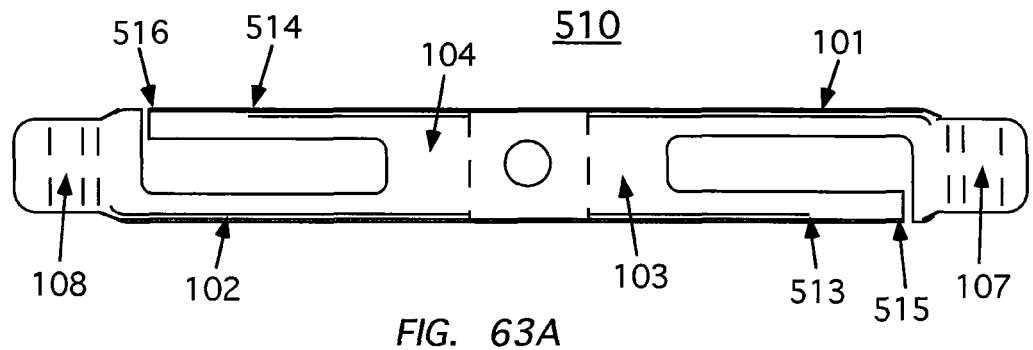
FIGS. 63A-63D illustrate a needle guard according to another implementation.

As shown in FIG. 63A, in the as-cut or stamped configuration, the needle guard is equipped with first and second elongate biasing members 513 and 514, respectively. In one implementation the first and second elongate biasing members 513 and 514 are generally situated opposite and substantially parallel to the first and second resilient arms 101 and 102, respectively. At least a distal end 515 of the first biasing member 513 is longitudinally aligned with at least a portion of the second resilient arm 102 so that when the needle guard 510 is formed and positioned on the needle 130, the distal end 515 abuts a part of the second resilient arm 102 (see FIG. 63B) to impart a biasing force that assists (along with the biasing force inherent to the second resilient arm 102) in urging the second resilient arm 102 against the shaft 131 of needle 130. In a like manner at least a portion of the distal end 516 of the second elongate biasing member 514 is longitudinally aligned with at least a portion of the first resilient arm 101 so that when the needle guard 510 is formed and positioned on the needle 130, the distal end 516 abuts a part of the first resilient arm 101 (see FIG. 63B) to impart a biasing force that assists (along with the biasing force inherent to the first resilient arm 101) in urging the second resilient arm 101 against the shaft 131 of needle 130.

Figure 63B:
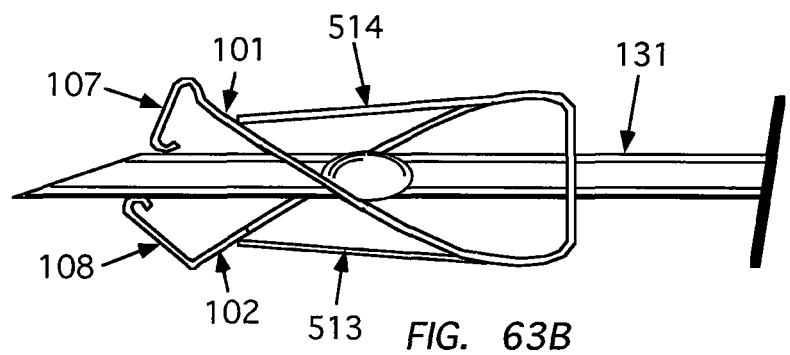
Figure 63D:
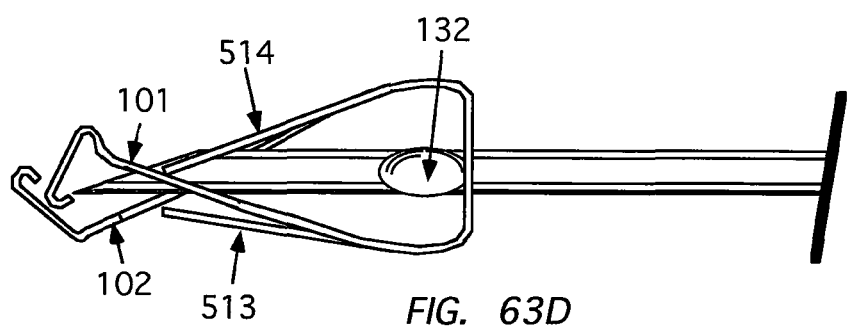
Figure 63C:
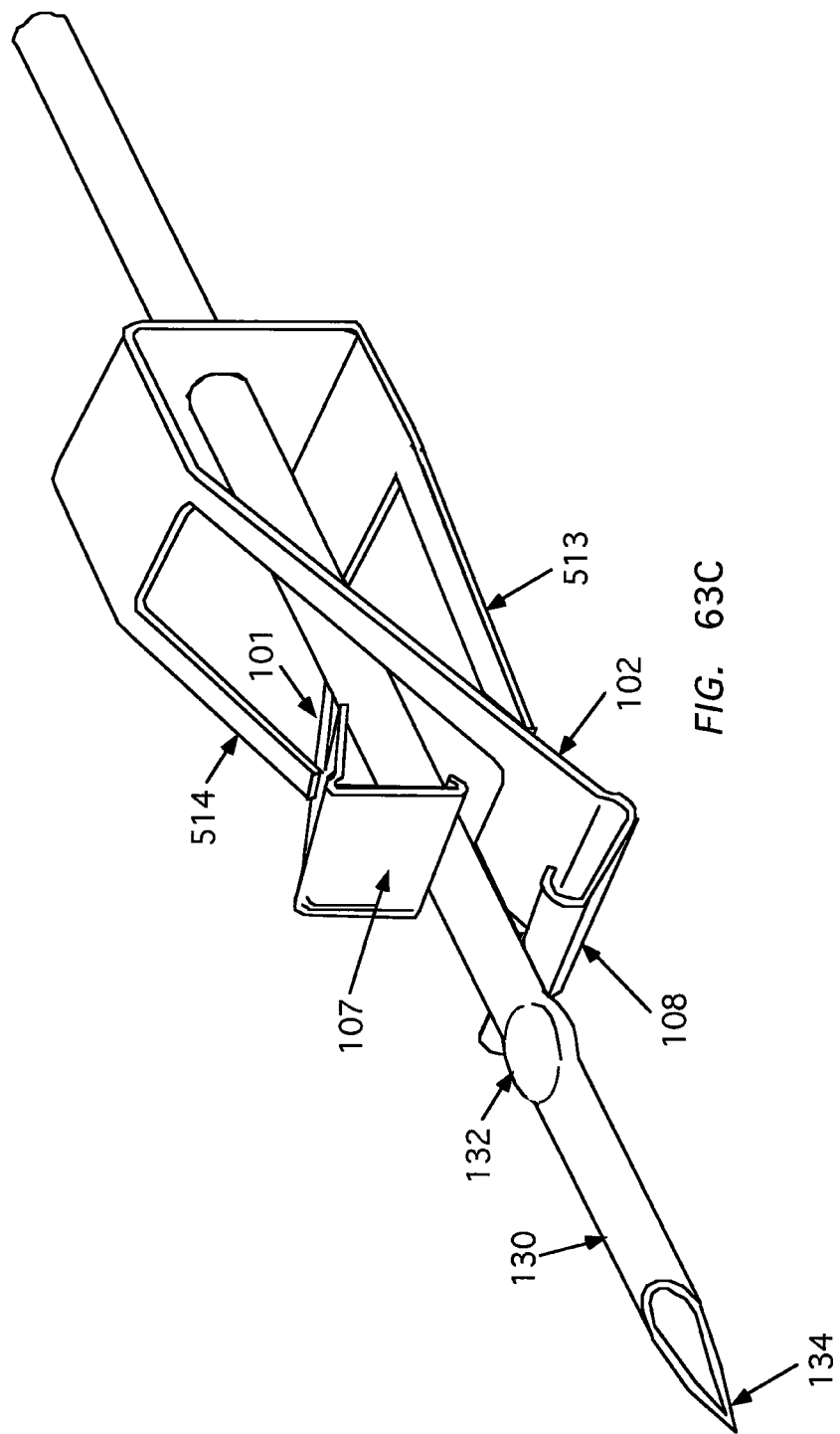

Whereas FIGS. 63B and 63C show the needle guard in a ready position prior to being activated to cover the distal tip 134 of the needle 130, FIG. 63D shows the needle guard in an activated state where it is stopped on a change in profile 132 on the needle shaft 131 and the distal ends 107, 108 of resilient arms 101, 102 are positioned over the distal tip 134. As shown in FIG. 63D, the distal ends 515, 516 of biasing members 513, 514 continue to engage the arms 101, 102 when the needle guard is in the activated state. Such engagement advantageously assists in maintaining the arms 101, 102 in their active positions and to resist outward forces that may be applied to the arms 101, 102 once the tip 134 has being properly covered.

Figure 64A:
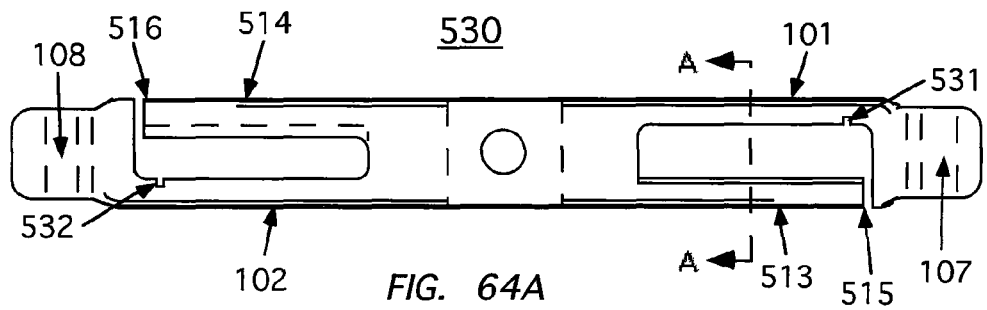
FIGS. 64A-64C illustrate a needle guard according to another implementation.
Figure 64C:
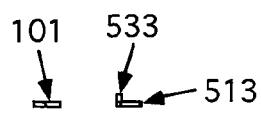
Figure 64B:
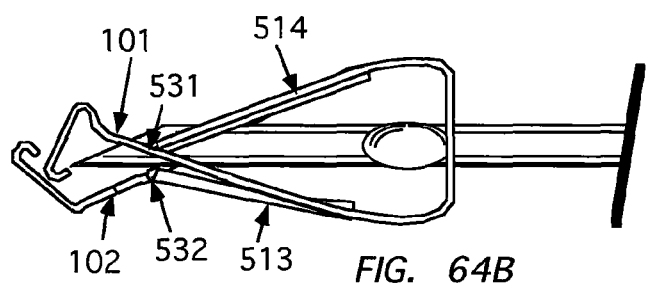
Figure 65:
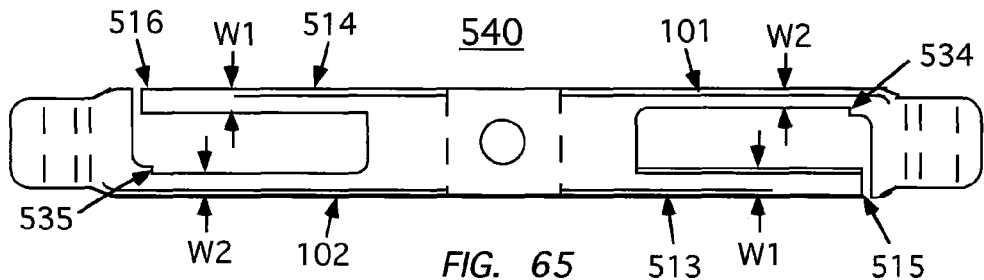
FIG. 65 illustrates a needle guard according to another implementation.
Figure 66A:
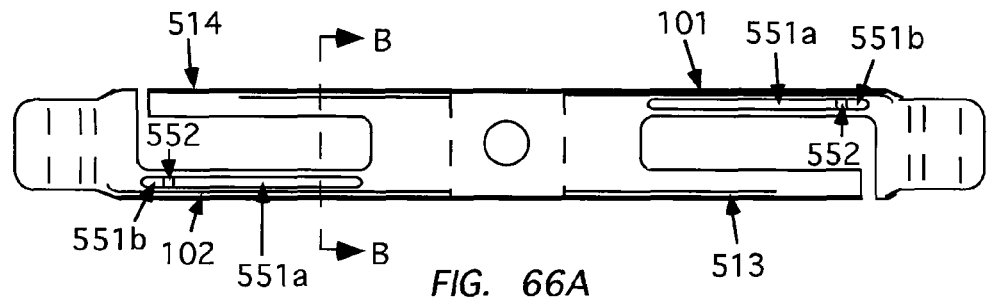
FIGS. 66A-66C illustrate a needle guard according to another implementation.
Figure 66B:
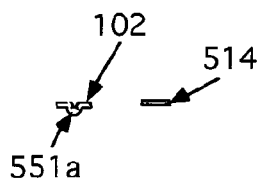
Figure 66C:
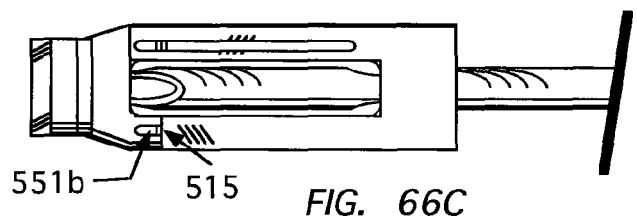
Figure 67A:
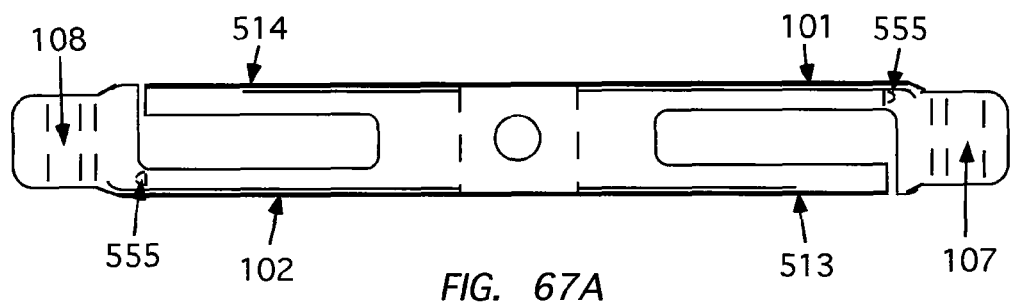
FIGS. 67A-67B illustrate a needle guard according to another implementation.
Figure 67B:
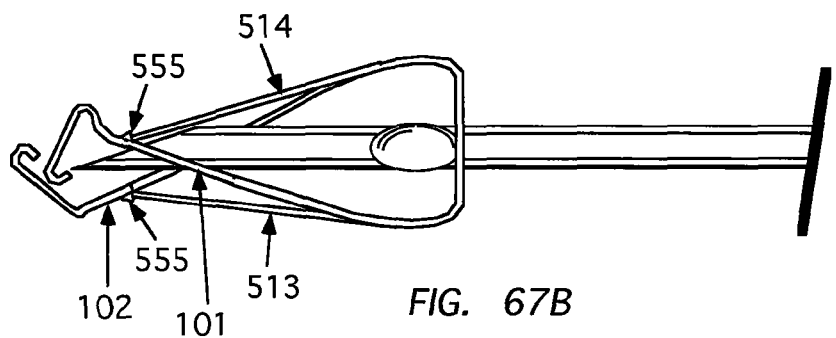
Figure 68A:
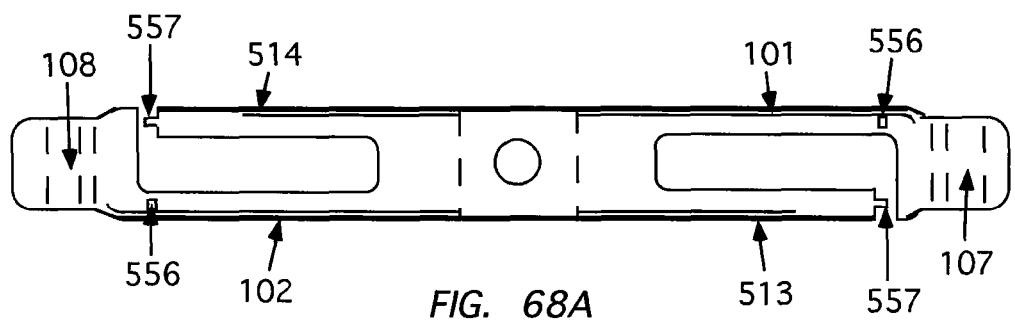
FIGS. 68A-68B illustrate a needle guard according to another implementation.
Figure 68B:
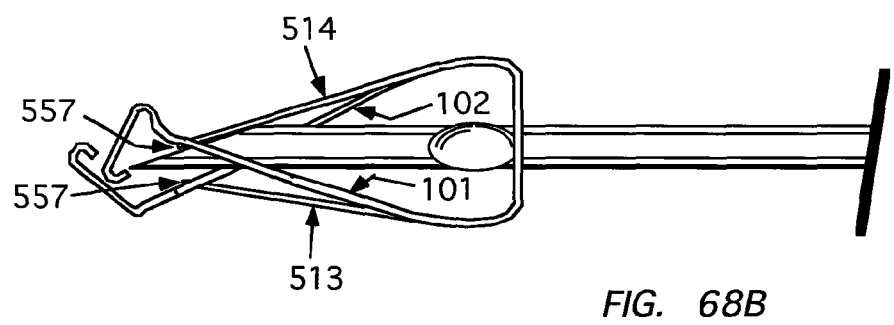

Stop and/or engagement features may be incorporated on or within the arms 101, 102 and/or biasing members 513, 514 to assist in maintaining the biasing members 513, 514 on the arms 101, 102 when the needle guard assumes its activated state. FIGS. 64-68 illustrate examples of such features. In some implementations, not shown in the figures, the distal ends 515, 516 of biasing members 513, 514 are guided on the arms 101, 102 by rails situated along at least a portion of the length of the arms. In the implementation of FIG. 64 cut-outs/notches 531 and 532 are provided on the inner perimeter of arms 101 and 102, respectively. In use, at least when the needle guard 530 is in the activated state, as shown in FIG. 64B, at least a portion of the distal ends 515 and 516 of the biasing members reside in notches 532 and 531, respectively, to assist in maintaining the arms 101 and 102 in a position to cover the distal tip 134 of the needle 130. In one implementation, as shown in FIG. 64C (a cross-sectional view along line A-A) an inner edge of arms 101 and/or 102 are bent to form strong backs 533 to provide the arms with additional stiffness. In the implementation of FIG. 65, ledges/shoulders 534 and 535 are respectively formed on an inner edge of arms 101 and 102 to which at least a portion of the distal ends 516 and 515 of biasing members 514 and 513 abut when the needle guard 540 is in an activated state. In one implementation, at least the distal ends 515 and 516 of biasing members 513 and 514 have a width dimension W1 that is greater than the width dimension W2 of arms 101 and 102. In the implementation of FIGS. 66A-66C each of arms 101 and 102 has along at least a portion of their length a pair of stamped indentations 551a, 551b that are longitudinally arranged so that a recess 552 exist between them. As shown in FIG. 66C, at least a portion of the distal ends 515, 516 of biasing members 513, 514 reside within a recess 552 at least when the needle guard is in the activated state. In the implementation of FIGS. 67A and 67B a raised feature 555 located on the outer side of each of arms 101 and 102 provides a surface on which at least a portion of the distal ends 515, 516 of biasing members 513, 514 rest when the needle guard is in the activated state as shown in FIG. 67B. In the implementation of FIGS. 68A and 68B each of arms 101, 102 are provided with apertures 556 that are adapted to receive tabs 557 formed on the distal ends 515, 516 of biasing members 513, 514. As shown in FIG. 68B, the tabs 557 reside within the apertures 556 at least when the needle guard is in the activated state.

Figure 69A:
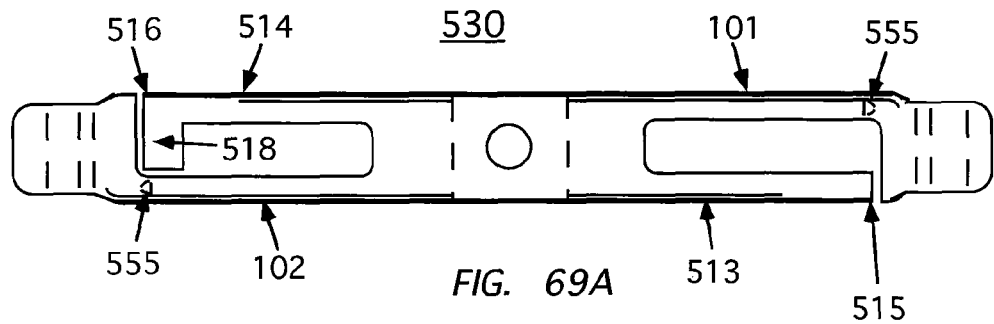
FIGS. 69A-69C illustrate a needle guard according to another implementation.
Figure 69B:
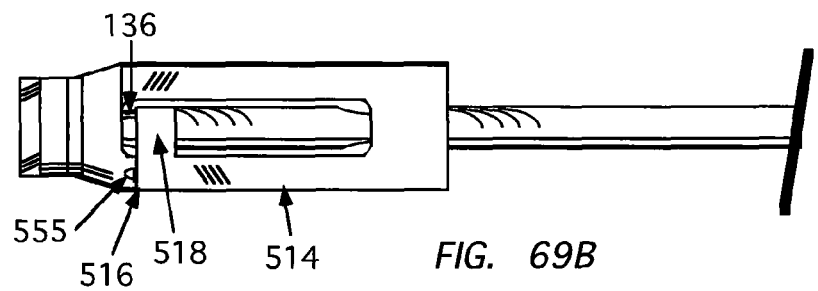
Figure 69C:
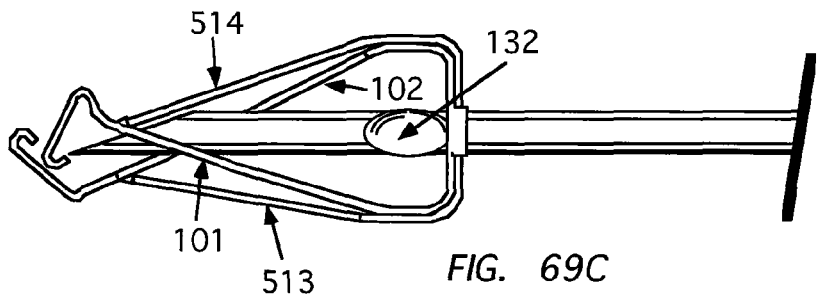

FIGS. 69A-69C show a needle guard similar to the needle guard depicted in FIGS. 67A and 67B. A difference lies in the construction of the distal end of biasing member 514. As shown in FIGS. 69A and 69B, a protrusion or tab 518 extends radially inward from the distal end 516 and is configured to at least partially cover the bevel 136 of the needle 130 when the needle guard assumes an activated state as shown in FIGS. 69B and 69C.

Figure 70A:
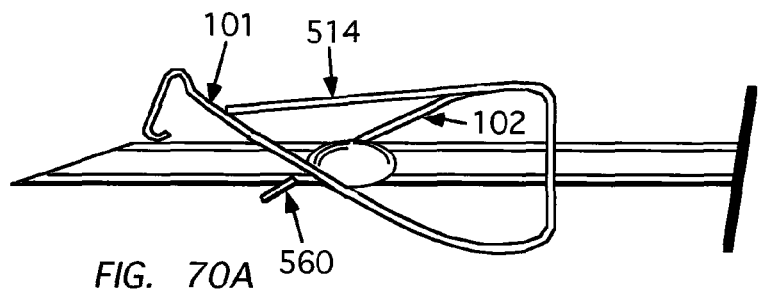
FIGS. 70A-70B illustrate a needle guard according to another implementation.
Figure 70B:
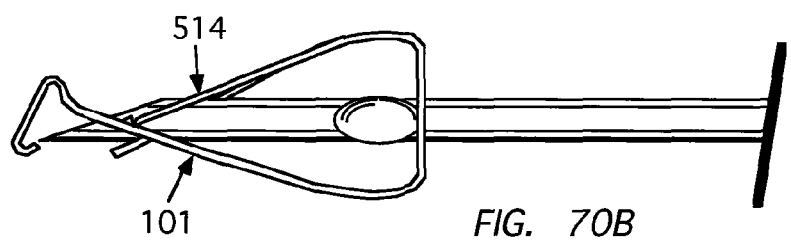

Like the implementation of FIG. 24, a needle guard incorporating the feature of a biasing member may also comprise only one arm 101 that is adapted to cover the distal tip of the needle. As shown in FIGS. 70A and 70B, in such an implementation arm 102 terminates at segment 560 and the guard is devoid of biasing member 513. Like the preceding implementations, biasing member 514 is provided to act upon an outer surface of arm 101.

Figure 71:
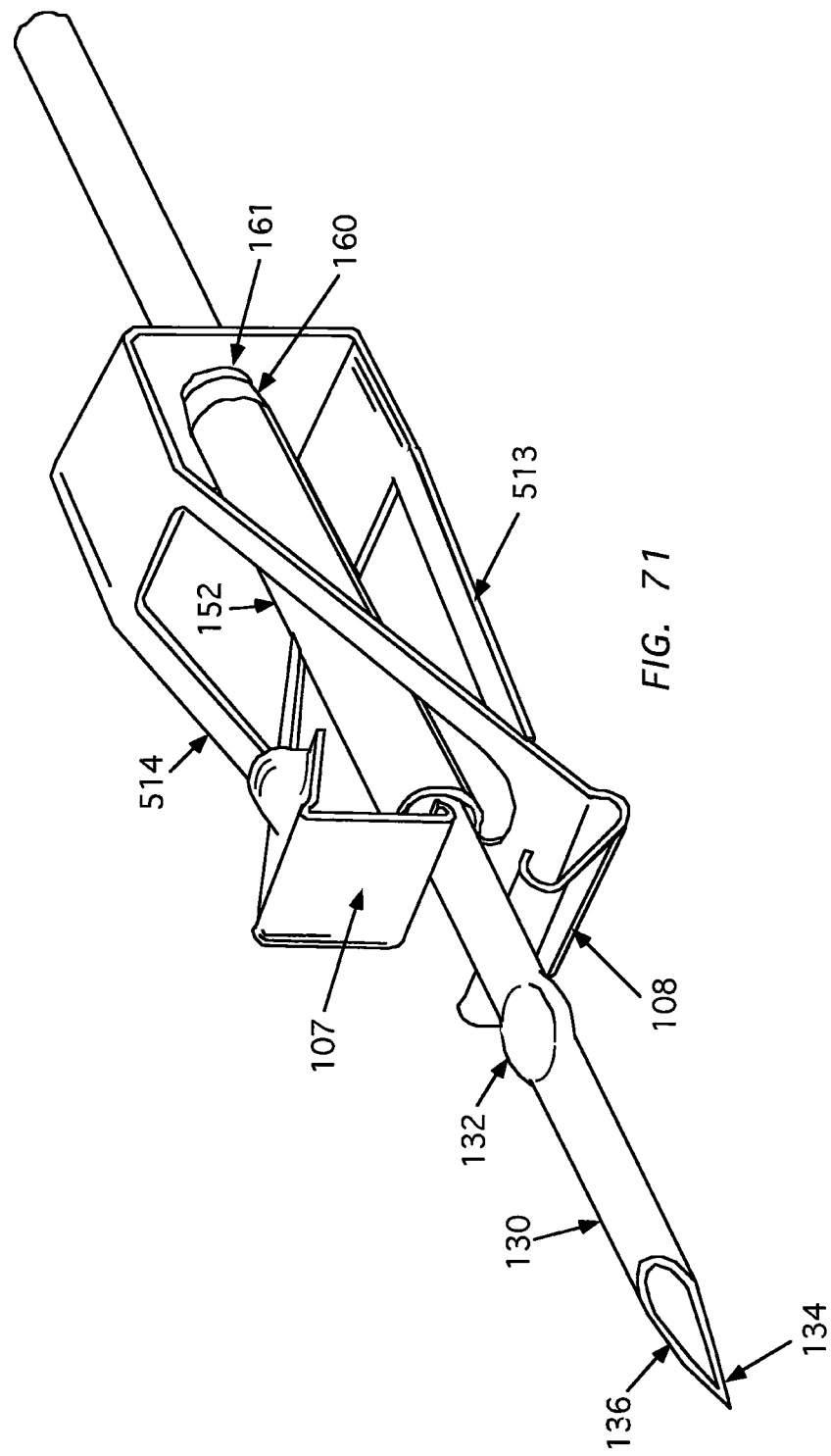
FIG. 71 illustrates a needle guard according to another implementation.

Biasing members may also be incorporated into needle guards comprising elongate members as shown in FIG. 71. The example of FIG. 71 shows a version of the needle guard 400 of FIG. 30 with biasing members 513 and 514.

Numerous exemplary implementations have been disclosed and described herein. It is to be appreciated however, that the present invention is in no way to be construed as to being limited to these examples.

What is claimed is:

1. A safety needle device comprising:
a needle having a needle shaft and a distal tip; and
a needle guard transitional between a ready state where the distal tip of the needle is in an unprotected state and an activated state where the distal tip of the needle is in a protected state, the needle guard comprising an arm and an elongate member slideable alongside the needle shaft as the needle guard is moved between the ready state and the activated state, the arm including a proximal section, a mid-section and a distal section, the proximal section having a first width and the distal section having a second width, the mid-section having a portion of a reduced width, the reduced width being less than one or both of the first and second widths so that an indentation is provided in a side of the arm, the arm intersecting the needle shaft along the reduced width portion of the mid-section of the arm located between the proximal and distal sections, when the needle is in the ready position and the retracted position the elongate member extends through the indentation in the mid-section of the arm, the elongate member having an open proximal end, a fixed open distal end and a through passage extending between the open proximal and distal ends, in the ready state the distal section of the arm resides on a distal section of the elongate member near the distal end of the elongate member where at least a portion of the distal section of the arm is urged against an outer side of the elongate member, the needle guard being configured such that as the needle guard transitions from the ready state to the activated state the distal section of the arm is able to move distally along the outer side of the distal section of the elongate member past the distal end of the elongate member and is able to move radially inward to at least partially lie over the fixed open distal end of the elongate member, the arm extends distally from a base having an aperture formed therein with the needle shaft passing through the aperture formed in the base, the elongate member comprises a proximal section that is disposed within the aperture of the base with the base being slideable on the proximal section of the elongate member between a first position when the needle guard is in the ready state and a second position distal to the first position when the needle guard is in the activated state.

2. A safety needle device according to claim 1, wherein the arm comprises a resilient material.

3. A safety needle device according to claim 2, wherein the elongate member extends distally from a position at or near the base when the needle guard is in the ready state.

4. A safety device according to claim 2, wherein the distal section of the arm comprises a wall segment having a distal end, the wall segment and mid-section of the arm disposed at different angular orientations with respect to the elongate member, the wall segment angled inwardly toward the elongate member, the distal end of the wall segment urged against the outer side of the elongate member when the needle guard is in the ready state, the distal end of the wall segment configured to disengage with the elongate member to at least partially lie over the distal end of the elongate member when the needle guard is in the activated state.

5. A safety device according to claim 4, wherein the distal end of the wall segment comprises a lip.

6. A safety device according to claim 5, wherein the elongate member comprises a feature at or near its distal end that is co-operable with the lip to secure the distal section of the arm to the distal end of the elongate member when the needle guard is in the activated state.

7. A safety needle device according to claim 1, wherein the needle shaft has a change in profile near the distal tip of the needle and an inner wall of the through passage located at or near the proximal end of the elongate member is configured to engage with the change in profile of the needle shaft to limit proximal movement of the needle with respect to the needle guard.

8. A safety needle device according to claim 7, wherein the elongate member has a length such that when the change in profile engages the inner wall of the through passage the entirety of the distal tip of the needle is positioned to reside within the through passage of the elongate member.

9. A safety needle device according to claim 1, wherein the needle guard is configured such that during a transition from the ready state to the activated state, upon a movement of the base from the first position to the second position, the distal section of the arm moves distally along the outer side of the elongate member.

10. A safety device according to claim 1, wherein the elongate member comprises an external shoulder that is configured to limit the distal movement of the base on the elongate member to the second position.

11. A safety device according to claim 1, wherein a radially extending member is positioned on the proximal section of the elongate member to limit the distal movement of the base on the elongate member to the second position.

12. A safety device according to claim 1, wherein the elongate member comprises a recess in the distal section near the distal end of the elongate member, at least a portion of the distal section of the arm residing in the recess when the needle guard is in the ready state.

13. A safety device according to claim 12, wherein the recess is adapted to receive at least a portion of the distal section of the arm in a manner that resists rotational movement of the arm on the elongate member when the needle guard is in the ready state.

14. A safety device according to claim 1, wherein a friction fit exists between a structure that defines the aperture and an outside surface of the proximal section of the elongate member, the friction fit sufficient to permit the base to be moved along the outside surface of the proximal section.

15. A safety device according to claim 1, further comprising a recess in an outer surface of the proximal section of the elongate member, a structure defining the aperture of the base resides in the recess when the needle guard is in the ready state.

16. A safety device according to claim 15, wherein the aperture is expandable upon a distally applied force being applied to the base to permit the base to be moved out of the recess and advanced distally to the second position.

17. A safety device according to claim 16, wherein radial expansion of the aperture is at least partially facilitated by one or more slits in the base, the one or more slits extending radially outward from an inner periphery of the aperture.

18. A safety device according to claim 1, wherein the proximal section of the elongate member comprises a frustoconical segment having a proximal end with a first diameter and a distal end with a second diameter, the second diameter greater than the first diameter, when the needle guard is in the ready state the first position of the base is at the proximal end of the frustoconical segment, the needle guard configured so that in the activated state the second position of the base is at the distal end of the frustoconical segment, in the ready state the aperture in the base has a diameter that is substantially equal to or slightly greater than the first diameter, the aperture adapted to expand to the second diameter when the base is moved distally along the frustoconical segment to the second end.

19. A safety device according to claim 18, wherein radial expansion of the aperture is at least partially facilitated by one or more slits in the base, the one or more slits extending radially outward from an inner periphery of the aperture.

20. A safety device according to claim 1, wherein at least a portion of the proximal section of the elongate member is keyed to a structure defining the aperture so as to inhibit rotational movement of the base and arm on the elongate member when the needle guard is in the ready state.

21. A safety device according to claim 1, wherein at least a portion of the proximal section of the elongate member is keyed to a structure defining the aperture so as to inhibit rotational movement of the base and arm on the elongate member when the needle guard is in the ready state and in the activated state.

22. A safety needle device comprising:
a needle having a needle shaft and a distal tip; and
a needle guard transitional between a ready state where the distal tip of the needle is in an unprotected state and an activated state where the distal tip of the needle is in a protected state, the needle guard comprising an arm and an elongate member slideable alongside the needle shaft as the needle guard is moved between the ready state and the activated state, the arm including a proximal section, a mid-section and a distal section, the proximal section having a first width and the distal section having a second width, the mid-section having a portion of a reduced width, the reduced width being less than one or both of the first and second widths so that an indentation is provided in a side of the arm, the arm intersecting the needle shaft along the reduced width portion of the mid-section of the arm located between the proximal and distal sections, when the needle is in the ready position and the retracted position the elongate member extends through the indentation in the mid-section of the arm, the elongate member having an open proximal end, a fixed open distal end and a through passage extending between the open proximal and distal ends, in the ready state the distal section of the arm resides on a distal section of the elongate member near the distal end of the elongate member where at least a portion of the distal section of the arm is urged against an outer side of the elongate member, the needle guard being configured such that as the needle guard transitions from the ready state to the activated state the distal section of the arm is able to move distally along the outer side of the distal section of the elongate member past the distal end of the elongate member, wherein the arm extends distally from a base having an aperture formed therein with the needle shaft passing through the aperture formed in the base, the arm comprises a resilient material with the mid-section being disposed between the proximal and distal sections, the distal section of the arm comprises a wall segment having a distal end, the wall segment and mid-section of the arm disposed at different angular orientations with respect to the elongate member, the wall segment angled inwardly toward the elongate member, the distal end of the wall segment urged against the outer side of the elongate member when the needle guard is in the ready state, the distal end of the wall segment configured to disengage with the elongate member to fully cover the distal end of the elongate member when the needle guard is in the activated state.

23. A safety device according to claim 22, wherein the wall segment and distal end of the elongate member co-operate to at least partially form a seal when the wall segment is positioned to fully cover the distal end of the elongate member.

24. A safety device according to claim 23, wherein one or both of the wall segment and the distal end of the elongate member is surface treated to enhance the formation of the seal.

25. A safety device according to claim 24, wherein one or both of the wall segment and the distal end of the elongate member is coated with a sealing agent.

26. A safety needle device comprising:
a needle having a needle shaft and a distal tip; and
a needle guard transitional between a ready state where the distal tip of the needle is in an unprotected state and an activated state where the distal tip of the needle is in a protected state, the needle guard comprising an arm having a distal section, the needle guard further comprising an elongate member slideable alongside the needle shaft as the needle guard is moved between the ready state and the activated state, the elongate member having an open proximal end, an open distal end and a through passage extending between the open proximal and distal ends, in the ready state the distal section of the arm resides on a distal section of the elongate member near the distal end of the elongate member where at least a portion of the distal section of the arm is urged against an outer side of the elongate member, the needle guard being configured such that as the needle guard transitions from the ready state to the activated state the distal section of the arm is able to move distally along the outer side of the distal section of the elongate member past the distal end of the elongate member and is able to move radially inward to at least partially lie over the open distal end of the elongate member, the elongate member comprising a proximal section and a recess in the distal section near the distal end of the elongate member, at least a portion of the distal section of the arm residing in the recess when the needle guard is in the ready state.

* * * * *